(12) United States Patent
Seme et al.

(10) Patent No.: US 10,342,581 B2
(45) Date of Patent: Jul. 9, 2019

(54) SYSTEM AND METHOD FOR SPINAL CORRECTION

(71) Applicant: K2M, Inc., Leesburg, VA (US)

(72) Inventors: Steven J. Seme, Savage, MN (US); Thomas J. Gisel, Chaska, MN (US); Matthew S. Stenulson, Eden Prairie, MN (US); John F. Otte, Minneapolis, MN (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/660,071

(22) Filed: Jul. 26, 2017

(65) Prior Publication Data

US 2017/0319237 A1 Nov. 9, 2017

Related U.S. Application Data

(60) Continuation of application No. 15/210,424, filed on Jul. 14, 2016, now Pat. No. 9,757,157, which is a
(Continued)

(51) Int. Cl.
*A61B 17/70* (2006.01)
*A61B 17/88* (2006.01)

(52) U.S. Cl.
CPC .......... *A61B 17/7001* (2013.01); *A61B 17/70* (2013.01); *A61B 17/701* (2013.01); *A61B 17/7002* (2013.01); *A61B 17/7004* (2013.01); *A61B 17/704* (2013.01); *A61B 17/705* (2013.01); *A61B 17/707* (2013.01); *A61B 17/7019* (2013.01); *A61B 17/7041* (2013.01); *A61B 17/7044* (2013.01); *A61B 17/7046* (2013.01); *A61B 17/7049* (2013.01); *A61B 17/7052* (2013.01); *A61B 17/7053* (2013.01); *A61B 17/8869* (2013.01)

(58) Field of Classification Search
CPC ............ A61B 17/7043; A61B 17/7049; A61B 17/705; A61B 17/7052; A61B 17/7046
See application file for complete search history.

(56) References Cited

U.S. PATENT DOCUMENTS 2,774,350 A 9/1952 Cleveland
3,242,922 A 3/1966 Thomas
(Continued)

FOREIGN PATENT DOCUMENTS

DE 2644735 A1 4/1977
DE 2845647 A1 5/1980
(Continued)

OTHER PUBLICATIONS

European Office Action dated Sep. 20, 2017, issued in EP 14 777 448.
(Continued)

*Primary Examiner* — Julianna N Harvey
(74) *Attorney, Agent, or Firm* — Lerner, David, Littenberg, Krumholz & Mentlik, LLP

(57) ABSTRACT

Methods of correcting a spinal deformity, including securing a first rod on a first side of a spine, securing an anchor on a second side of a spine, securing a lateral coupling between the rod and the anchor, translating and/or derotating the spine and securing a second rod on a second side of the spine to provide secondary stabilization to the spine.

18 Claims, 32 Drawing Sheets

Related U.S. Application Data division of application No. 14/456,454, filed on Aug. 11, 2014, now Pat. No. 9,451,987, which is a continuation-in-part of application No. 13/865,775, filed on Apr. 18, 2013, now Pat. No. 8,920,472, which is a continuation-in-part of application No. 13/297,841, filed on Nov. 16, 2011, now abandoned, said application No. 14/456,454 is a continuation-in-part of application No. 14/029,610, filed on Sep. 17, 2013, now Pat. No. 9,468,469.

(56) References Cited

U.S. PATENT DOCUMENTS

| | | |
|---|---|---|
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,720,746 A | 2/1998 | Soubeiran |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |

(56) References Cited

U.S. PATENT DOCUMENTS

| | | |
|---|---|---|
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,033,412 A | 3/2000 | Losken et al. |
| 6,039,738 A | 3/2000 | Sanders et al. |
| 6,050,997 A | 4/2000 | Mullane |
| 6,053,921 A | 4/2000 | Wagner et al. |
| 6,066,140 A | 5/2000 | Gertzbein et al. |
| 6,077,268 A | 6/2000 | Farris et al. |
| 6,080,156 A | 6/2000 | Asher et al. |
| 6,083,224 A | 7/2000 | Gertzbein et al. |
| 6,086,590 A | 7/2000 | Margulies et al. |
| 6,101,678 A | 8/2000 | Malloy et al. |
| 6,110,173 A | 8/2000 | Thomas, Jr. |
| 6,123,706 A | 9/2000 | Lange |
| 6,132,431 A | 10/2000 | Nilsson et al. |
| 6,132,464 A | 10/2000 | Martin |
| 6,136,000 A | 10/2000 | Louis et al. |
| 6,176,861 B1 | 1/2001 | Bernstein et al. |
| 6,231,575 B1 | 5/2001 | Krag |
| 6,248,106 B1 | 6/2001 | Ferree |
| 6,251,111 B1 | 6/2001 | Barker et al. |
| 6,254,603 B1 | 7/2001 | Gertzbein et al. |
| 6,261,288 B1 | 7/2001 | Jackson |
| 6,264,658 B1 | 7/2001 | Lee et al. |
| 6,273,914 B1 | 8/2001 | Papas |
| 6,277,120 B1 | 8/2001 | Lawson |
| 6,283,967 B1 | 9/2001 | Troxell et al. |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,379,357 B1 | 4/2002 | Bernstein et al. |
| 6,391,030 B1 | 5/2002 | Wagner et al. |
| 6,402,749 B1 | 6/2002 | Ashman |
| 6,402,752 B2 | 6/2002 | Schaffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,471,704 B2 | 10/2002 | Gertzbein et al. |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz-Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,585,738 B1 | 7/2003 | Mangione et al. |
| 6,589,243 B1 | 7/2003 | Viart et al. |
| 6,602,254 B2 | 8/2003 | Gertzbein et al. |
| 6,602,818 B2 | 8/2003 | Choi et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,736,817 B2 | 5/2004 | Troxell et al. |
| 6,749,612 B1 | 6/2004 | Conchy et al. |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,887,241 B1 | 5/2005 | McBride et al. |
| 6,902,580 B2 | 6/2005 | Fallin et al. |
| 6,946,000 B2 | 9/2005 | Senegas et al. |
| 6,966,910 B2 | 11/2005 | Ritland |
| 6,966,930 B2 | 11/2005 | Amin et al. |
| 6,974,478 B2 | 12/2005 | Reiley et al. |
| 6,986,771 B2 | 1/2006 | Paul et al. |
| 7,008,423 B2 | 3/2006 | Assaker et al. |
| 7,018,379 B2 | 3/2006 | Drewry et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,051,451 B2 | 5/2006 | Augostino et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,090,698 B2 | 8/2006 | Goble et al. |
| 7,104,992 B2 | 9/2006 | Bailey |
| RE39,325 E | 10/2006 | Bryan |
| 7,128,743 B2 | 10/2006 | Metz-Stavenhagen |
| 7,137,986 B2 | 11/2006 | Troxell et al. |
| 7,160,312 B2 | 1/2007 | Saadat |
| 7,220,262 B1 | 5/2007 | Hynes |
| 7,261,714 B2 | 8/2007 | Richelsoph |
| 7,270,665 B2 | 9/2007 | Morrison et al. |
| 7,290,347 B2 | 11/2007 | Augostino et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,406,775 B2 | 8/2008 | Funk et al. |
| 7,445,635 B2 | 11/2008 | Fallin et al. |
| 7,473,267 B2 | 1/2009 | Nguyen et al. |
| 7,473,269 B1 | 1/2009 | Hynes |
| 7,481,828 B2 | 1/2009 | Mazda et al. |
| 7,507,242 B2 | 3/2009 | Triplett et al. |
| 7,524,324 B2 | 4/2009 | Winslow et al. |
| 7,566,345 B1 | 7/2009 | Fallin et al. |
| 7,588,578 B2 | 9/2009 | Triplett et al. |
| 7,588,590 B2 | 9/2009 | Chervitz et al. |
| 7,591,836 B2 | 9/2009 | Dick et al. |
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,145 B2 | 4/2010 | Reiley et al. |
| 7,708,762 B2 | 5/2010 | McCarthy et al. |
| 7,717,939 B2 | 5/2010 | Ludwig et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,771,474 B2 | 8/2010 | Cordaro |
| 7,794,476 B2 | 9/2010 | Wisnewski |
| 7,794,478 B2 | 9/2010 | Nilsson |

(56) References Cited

U.S. PATENT DOCUMENTS

| | | |
|---|---|---|
| 7,799,054 B2 | 9/2010 | Kwak et al. |
| 7,819,902 B2 | 10/2010 | Abdelgany et al. |
| 7,833,252 B2 | 11/2010 | Justis et al. |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,057,472 B2 | 11/2011 | Walker et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Vallespir |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 8,828,058 B2 | 9/2014 | Elsebaie et al. |
| 9,113,959 B2 | 8/2015 | Seme et al. |
| 9,451,987 B2 | 9/2016 | Seme et al. |
| 9,757,157 B2 | 9/2017 | Seme et al. |
| 9,827,017 B2 | 11/2017 | Seme et al. |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2002/0169448 A1 | 11/2002 | Vanacker |
| 2003/0040746 A1 | 2/2003 | Mitchell et al. |
| 2003/0045878 A1 | 3/2003 | Petit et al. |
| 2003/0045879 A1 | 3/2003 | Minfelde et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036240 A1 | 2/2006 | Colleran et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0247628 A1 | 11/2006 | Rawlins et al. |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |

(56) References Cited

U.S. PATENT DOCUMENTS

| | | |
|---|---|---|
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0100339 A1 | 5/2007 | Clement et al. |
| 2007/0161987 A1 | 7/2007 | Capote et al. |
| 2007/0161993 A1 | 7/2007 | Lowery et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0173829 A1 | 7/2007 | Drewry et al. |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276367 A1 | 11/2007 | Puno |
| 2007/0276374 A1 | 11/2007 | Broman et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0065069 A1 | 3/2008 | Betz et al. |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0109039 A1 | 5/2008 | Michielli et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0195159 A1 | 8/2008 | Kloss |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262545 A1 | 10/2008 | Simonson |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Amin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0298882 A1 | 11/2010 | James |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2011/0270314 A1* | 11/2011 | Mueller ............... A61B 17/704 606/264 |
| 2012/0109197 A1 | 5/2012 | Carl et al. |
| 2012/0158064 A1 | 6/2012 | Kroll |
| 2012/0221057 A1 | 8/2012 | Zhang et al. |
| 2013/0123851 A1 | 5/2013 | Seme et al. |
| 2013/0123853 A1 | 5/2013 | Seme et al. |
| 2013/0184757 A1 | 7/2013 | Seme et al. |
| 2013/0211455 A1 | 8/2013 | Seme |
| 2013/0231703 A1 | 9/2013 | Seme et al. |
| 2014/0236234 A1 | 8/2014 | Kroll et al. |
| 2014/0379033 A1 | 12/2014 | Elsebaie et al. |
| 2015/0080953 A1 | 3/2015 | Otte et al. |
| 2015/0080954 A1 | 3/2015 | Otte et al. |

FOREIGN PATENT DOCUMENTS

| | | |
|---|---|---|
| EP | 0260044 A1 | 3/1988 |
| EP | 0322334 A1 | 6/1989 |

(56) References Cited

FOREIGN PATENT DOCUMENTS

| | | |
|---|---|---|
| EP | 0418387 A1 | 3/1991 |
| EP | 1281361 A1 | 2/2003 |
| EP | 1381361 A1 | 1/2004 |
| EP | 1600112 A1 | 11/2005 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2892617 A1 | 5/2007 |
| FR | 2900563 A1 | 11/2007 |
| GB | 0780652 A | 8/1957 |
| SU | 0888968 A1 | 12/1981 |
| WO | 9213496 A1 | 8/1992 |
| WO | 0217803 A2 | 3/2002 |
| WO | 2004017705 A2 | 3/2004 |
| WO | 2006010844 A1 | 2/2006 |
| WO | 2006017641 A2 | 2/2006 |
| WO | 2006136937 A2 | 12/2006 |
| WO | 2007051924 A1 | 5/2007 |
| WO | 2008086467 A2 | 7/2008 |
| WO | 2008154313 A1 | 12/2008 |
| WO | 2010053662 A1 | 5/2010 |
| WO | 2010056650 A1 | 5/2010 |
| WO | 2010111500 A2 | 9/2010 |
| WO | 2012167105 A1 | 12/2012 |
| WO | 2014062942 A1 | 4/2014 |
| WO | 2014172632 A2 | 10/2014 |

OTHER PUBLICATIONS

Berry, James L. et al., A Morphometric Study of Human Lumbar and Selected Thoracic Vertebrae, 12 Spine 362 (1987).
European Search Report issued in EP Application No. 12154799, completed Mar. 2, 2012, 9 pages.
Fujita, Masaru et al., A Biomechanical Analysis of Sublaminar and Subtransverse Process Fixation Using Metal Wires and Polyethylene Cables, 31 Spine 2202 (2006).
Girardi, Federico P. et al., Safety of Sublaminar Wires With Isola Instrumentation for the Treatment of Idiopathic Scoliosis, 25 Spine 691 (2000).
International Application No. PCT/US2008/065979, filed Jun. 5, 2008, entitled Medical Device and Method to Correct Deformity.
International Application No. PCT/US2009/063833, filed Nov. 10, 2009, entitled Growth Directed Vertebral Fixation System With Distractible Connector(s) and Apical Control.
International Application No. PCT/US2010/028684, filed Mar. 25, 2010, entitled Semi-Constrained Anchoring System.
International Search Report and Written Opinion issued in PCT/US2005/027692, dated May 19, 2008, 4 pages.
International Search Report and Written Opinion issued in PCT/US2008/065979, dated Oct. 2, 2008, 7 pages.
International Search Report and Written Opinion issued in PCT/US2009/063833, dated Mar. 15, 2010, 14 pages.
International Search Report and Written Opinion issued in PCT/US2010/028684, dated Sep. 28, 2010, 19 pages.
International Search Report and Written Opinion issued in PCT/US2010/036375, dated Sep. 10, 2010, 16 pages.
International Search Report and Written Opinion issued in PCT/US2010/047117, dated Dec. 2, 2010.
International Search Report and Written Opinion issued in PCT/US2011/049693, dated Nov. 15, 2011, 16 pages.
International Search Report and Written Opinion issued in PCT/US2012/040493, dated Aug. 21, 2012, 15 pages.
International Search Report and Written Opinion issued in PCT/US2012/065262, dated Feb. 5, 2013, 8 pages.
International Search Report and Written Opinion issued in PCT/US2013/065488, dated Feb. 18, 2014, 10 pages.
Invitation to Pay Additional Fees and Partial Search Report issued in PCT/US2010/028684, dated Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and in Vitro Determination of the Axial Rotational Axis of the Human Thoracic Spine, 31 Spine E984 (2006).
Rajasekaran S. et al., Eighteen-Level Analysis of Vertebal Rotation Following Harrington-Luque Instrumentaton in Idiopathic Scoliosis, 76 J Bone Joint Surg Am. 104 (1994).
U.S. Appl. No. 12/411,558, filed Mar. 26, 2009, entitled Alignment System With Longitudinal Support Features.
U.S. Appl. No. 12/411,562, filed Mar. 26, 2009, entitled Semi-Constrained Anchoring System.
U.S. Appl. No. 12/485,796, filed Jun. 16, 2009 entitled Deformity Alignment System With Reactive Force Balancing.
U.S. Appl. No. 12/560,199, filed Sep. 15, 2009, entitled Growth Modulation System.
Wenger, Dennis R. et al., Biomechanics of Scoliosis Correction by Segmental Spinal Instrumentation, 7 Spine 260 (1982).
White III, Augustus A. et al., Biomechancis of the Spine 28-29, Tbl. 1-5 (2d ed. 1990).
European Search Report dated Jan. 25, 2016, issued in EP 15180519.
European Communication dated Jan. 2, 2017, issued in European Application No. 14 777 448.
Australian Examination Report dated Apr. 20, 2018, in AU Appln. No. 2014321490.
Australian Examination Report dated Jan. 6, 2018, issued in AU Application No. 2014253786.
Eglin, D. et al., "Degradable Polymeric Materials for Osteosynthesis: tutorial", European Cells and Materials, vol. 16, Dec. 2008, pp. 80-91.
European Search Report dated Oct. 7, 2016, issued in EP Application No. 14784708.
International Search Report and Written Opinion issued in PCT/US2014/055926, dated Jan. 29, 2015, 12 pages.
International Search Report for Application No. PCT/US2014/034644 dated May 1, 2015, 4 pages.

* cited by examiner

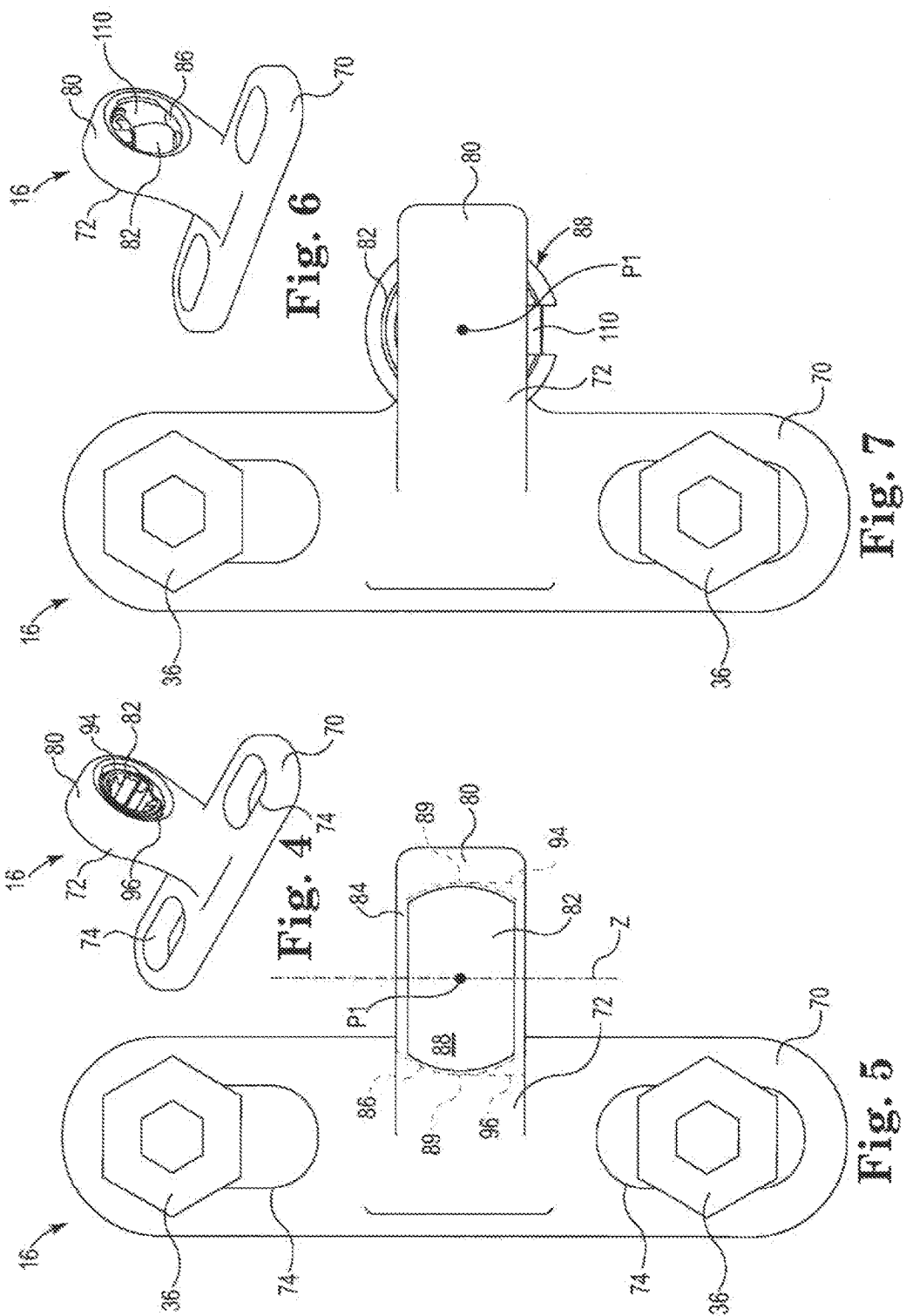

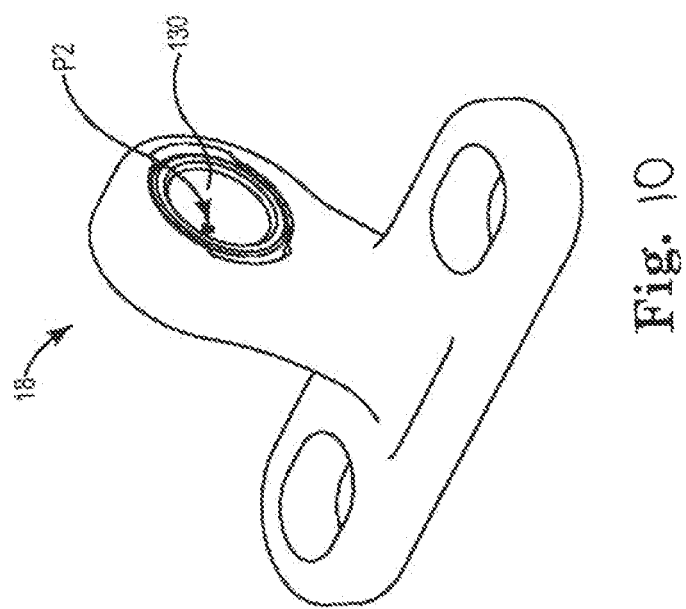

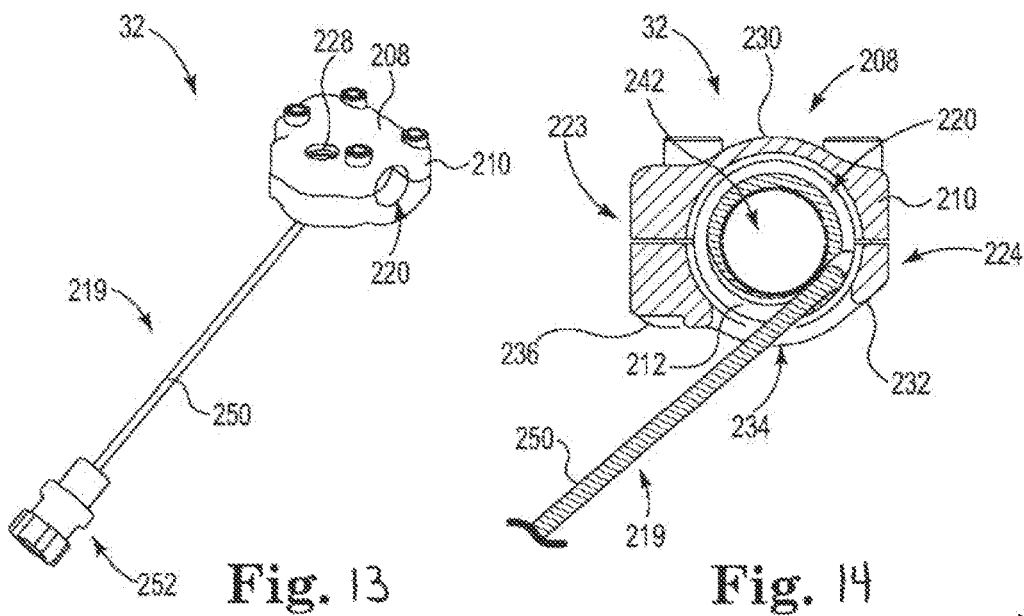
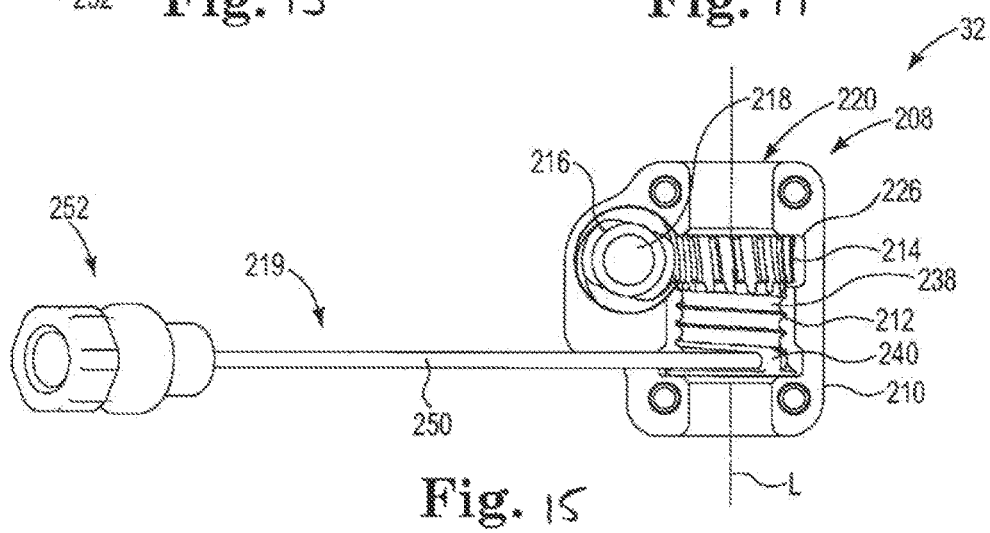
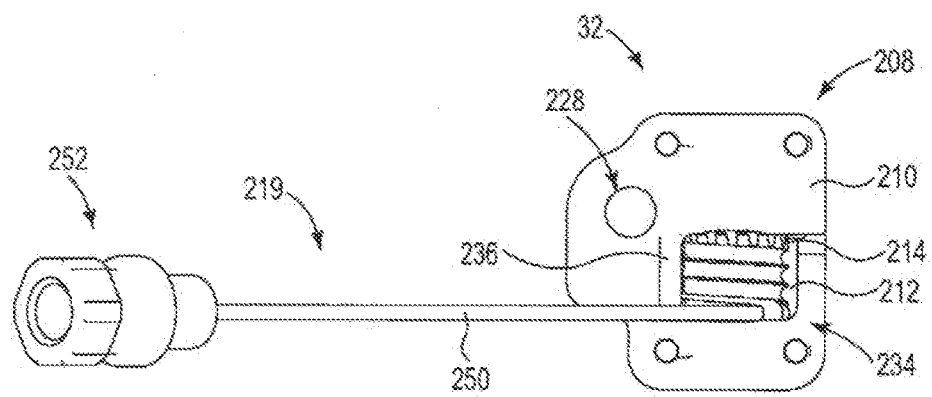

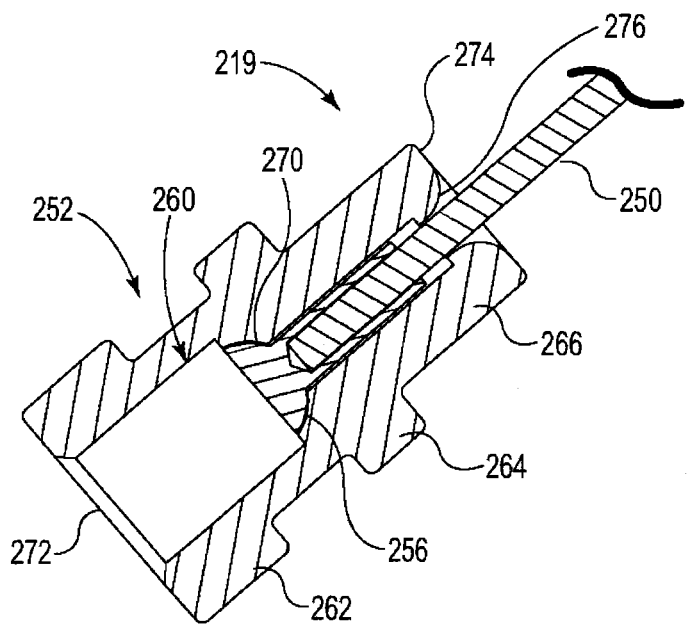
Fig. 17
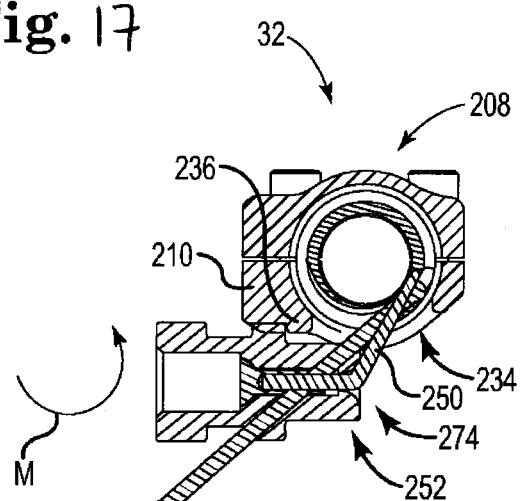
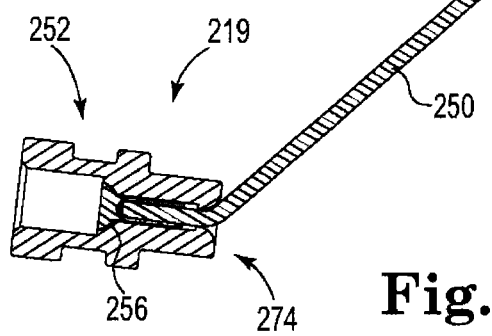
Fig. 18

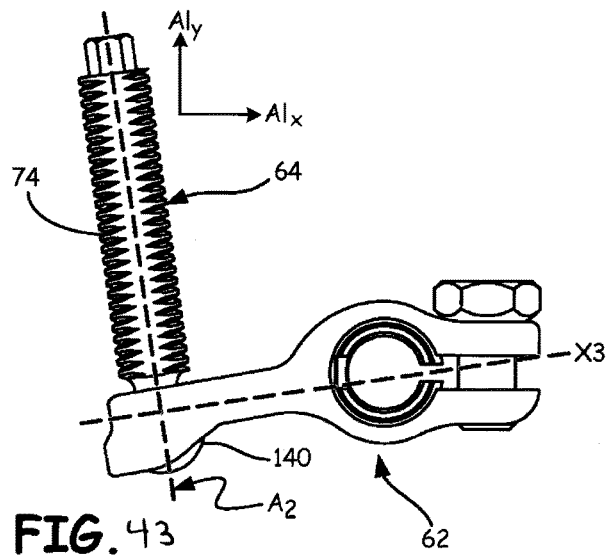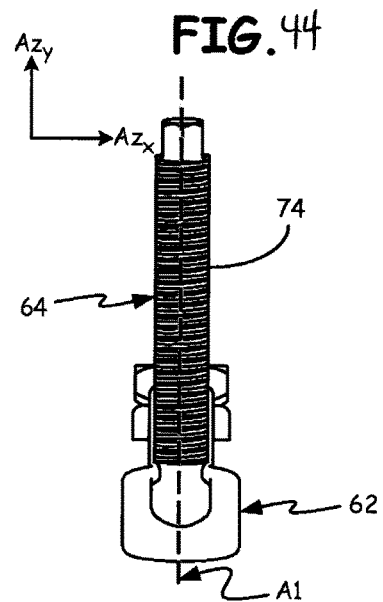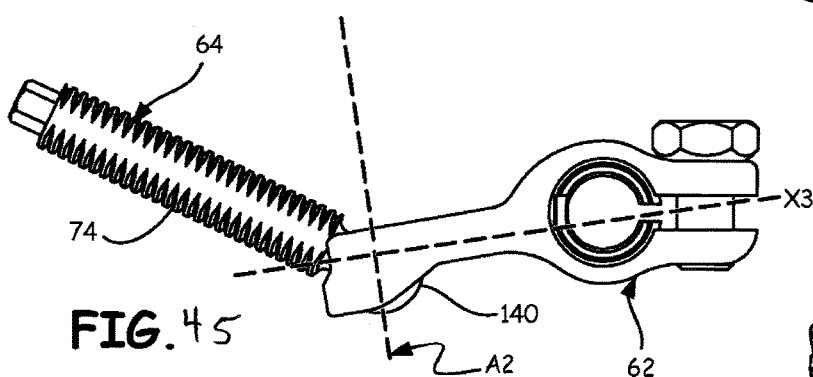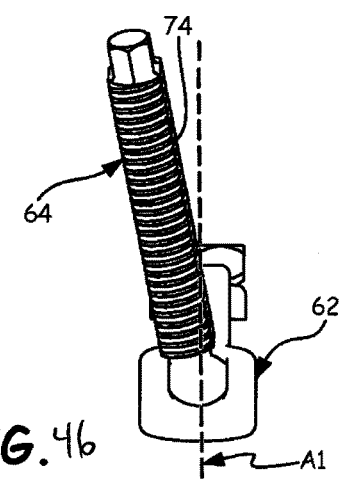
FIG. 43
FIG. 44
FIG. 45
FIG. 46

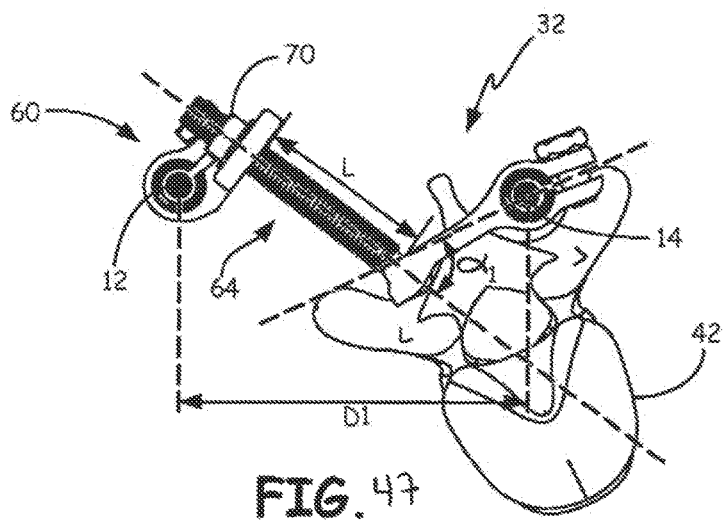
FIG. 47
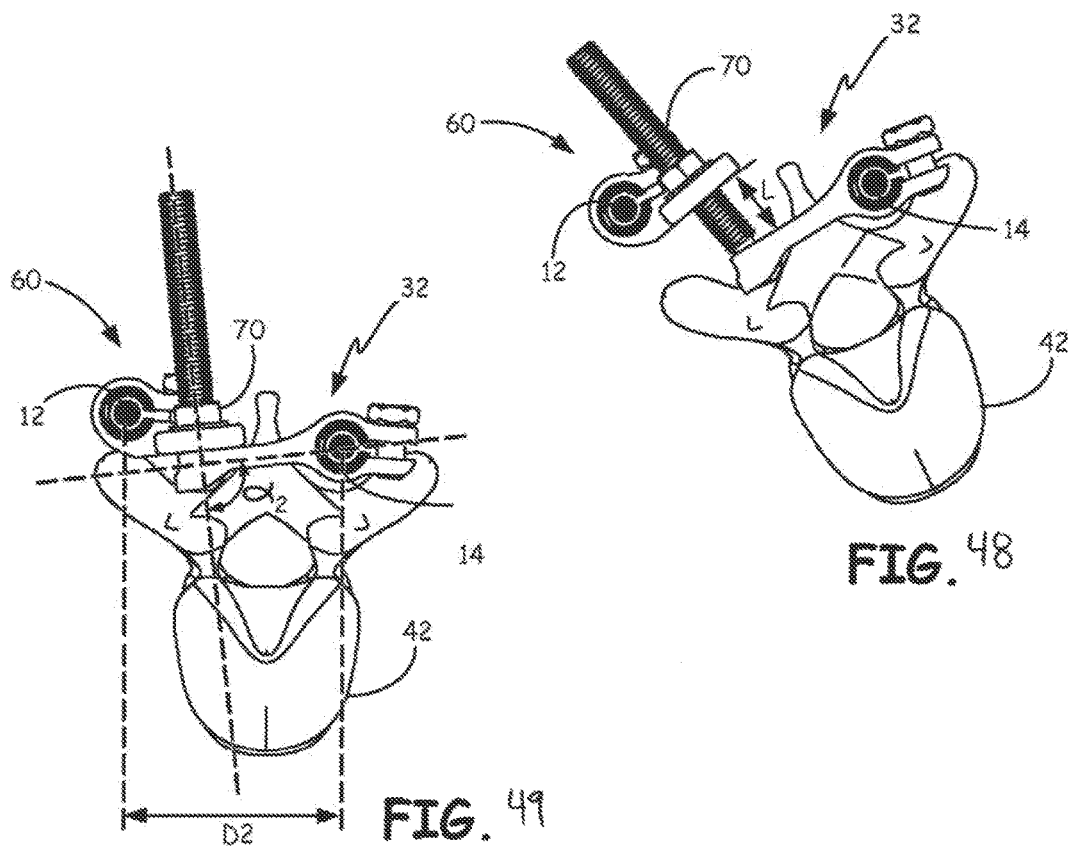
FIG. 48
FIG. 49

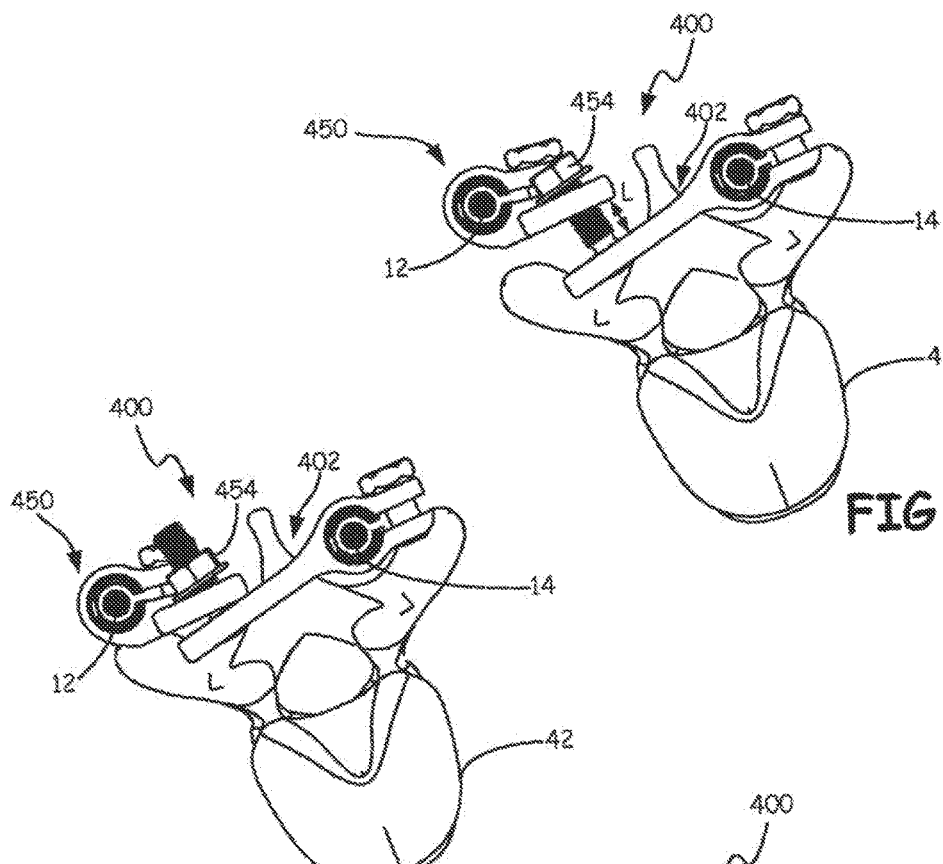
FIG. 57
FIG. 58
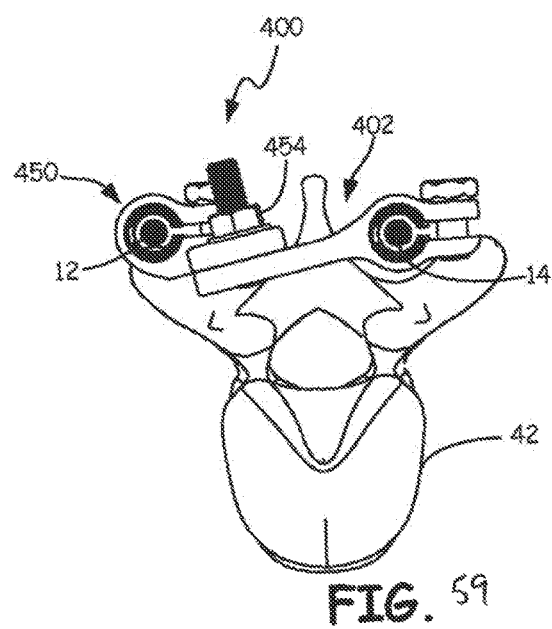
FIG. 59

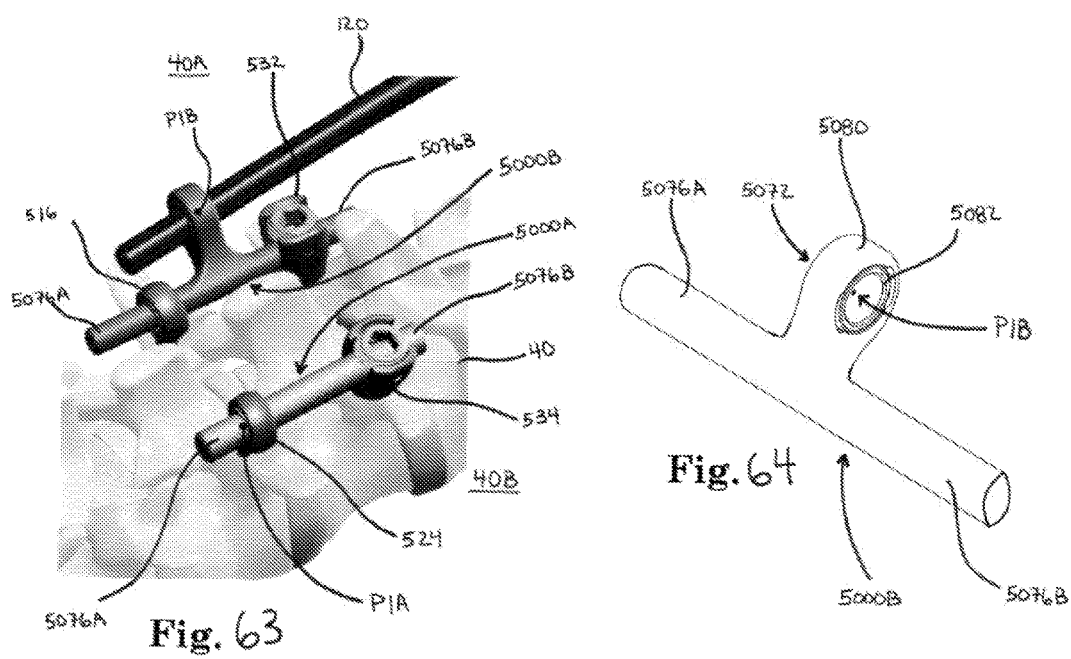

SYSTEM AND METHOD FOR SPINAL CORRECTION

CROSS-REFERENCE TO RELATED APPLICATIONS

This application is a continuation of U.S. patent application Ser. No. 15/210,424, filed Jul. 14, 2016, which is a division of U.S. patent application Ser. No. 14/456,454, filed Aug. 11, 2014, now U.S. Pat. No. 9,451,987, which is a continuation-in-part of U.S. patent application Ser. No. 14/029,610, filed Sep. 17, 2013, now U.S. Pat. No. 9,468,469, and a continuation-in-part of U.S. patent application Ser. No. 13/865,775, filed Apr. 18, 2013, now U.S. Pat. No. 8,920,472, which is a continuation-in-part of U.S. patent application Ser. No. 13/297,841, filed Nov. 16, 2011, now abandoned. The entire contents of each of the above disclosures are hereby incorporated by reference.

INCORPORATION BY REFERENCE OF ADDITIONAL DISCLOSURES

Additional examples of system components and corrective methodology in accordance with various embodiments of the present invention are set forth in U.S. App. Pub. 2010/0318129, filed Jun. 16, 2009 and entitled "Deformity Alignment System with Reactive Force Balancing"; U.S. App. Pub. 2010/0249837, filed Mar. 26, 2009 and entitled "Semi-Constrained Anchoring System"; U.S. App. Pub. 2011/0054536, filed Sep. 1, 2010 and entitled "Growth Directed Vertebral Fixation System with Distractible Connector(s) and Apical Control"; U.S. Pat. No. 7,658,753, issued Feb. 9, 2010 and entitled "Device and Method for Correcting a Spinal Deformity"; and U.S. App. Pub. 2009/0012565, filed on Jun. 5, 2008 and entitled "Medical Device and Method to Correct Deformity," the entire contents of each of which are incorporated herein by reference.

BACKGROUND

Various systems have been proposed for treating spinal deformities such as scoliosis, spondylolisthesis, and a variety of others. Primary surgical methods for correcting a spinal deformity utilize instrumentation to correct the deformity as much as possible and separate implantable hardware systems to rigidly stabilize and maintain the correction.

SUMMARY

Some aspects relate to a spinal correction system for correcting a spinal deformity of a patient's spinal column, the patient's spinal column including a first vertebra and a second vertebra and having a first side and a second side opposite to the first side, the spinal correction system comprising: a first rod adapted to extend longitudinally along the first side of the spine of the patient; a second rod adapted to extend longitudinally along the second side of the spine of the patient; a transverse coupler adapted to couple the first rod and the second rod such that the first rod and the second rod are constrained against substantial lateral translation relative to one another; a first rod anchor adapted to be fixed to the first vertebra of the spine at an inferior position relative to the transverse coupler, the first rod anchor coupled to the first rod such that the first rod is secured against substantial lateral translation relative to the first rod anchor while allowing the first rod to change alignment relative to the first rod anchor; a second rod anchor adapted to be fixed to the second vertebra of the spine at a superior position relative to the transverse coupler, the second rod anchor coupled to the first rod such that the first rod is secured against substantial lateral translation relative to the first rod anchor while allowing the first rod to change alignment relative to the second rod anchor; a third rod anchor adapted to be fixed to a second side inferior vertebra of the spine at an inferior position relative to the transverse coupler, the third rod anchor coupled to the second rod such that the second rod is secured against substantial lateral translation relative to the third rod anchor while allowing the second rod to change alignment relative to the third rod anchor; and a fourth rod anchor adapted to be fixed to a second side superior vertebra of the spine at a superior position relative to the transverse coupler, the fourth rod anchor coupled to the second rod such that the second rod is secured against substantial lateral translation relative to the fourth rod anchor while allowing the second rod change alignment relative to the fourth rod anchor.

Some aspects relate to a spinal correction system for correcting a spinal deformity of a patient's spinal column, the spinal deformity defining a deformity section and including an upper deformity level and a lower deformity level, the patient's spinal column including a plurality of vertebrae, the spinal correction system comprising: a first rod adapted to extend longitudinally along a first side of the spine of the patient, the first rod having a length such that the first rod extends from the upper level of the spinal deformity to the lower level of the spinal deformity; and a plurality of rod anchors, wherein for each rod anchor of the plurality of rod anchors, the rod anchor includes a pivot point and is: secured to a vertebra of the patient's spine that is different from any vertebra to which any other rod anchor of the plurality of rod anchors is secured; and coupled to the first rod such that the first rod is secured against substantial lateral translation relative to the pivot point of the rod anchor while allowing the first rod to change alignment relative to the pivot points of each of the other rod anchors of the plurality of rod anchors.

Some aspects relate to a spinal correction system comprising: a first rod configured to extend along a first side of a spine; a first rod anchor configured to be secured to a vertebra of the spine and to laterally constrain the first rod while allowing the first rod to slide axially and to change in pitch, yaw, and roll about a first pivot point; a second rod anchor configured to be secured to a vertebra of the spine and to laterally constrain the first rod while allowing the first rod to slide axially and to change in pitch, yaw, and roll about a second pivot point; a second rod configured to extend along a second side of the spine; a third rod anchor configured to be secured to a vertebra of the spine and to laterally constrain the second rod while allowing the second rod to slide axially and to change in pitch, yaw, and roll about a third pivot point; a fourth rod anchor configured to be secured to a vertebra of the spine and to laterally constrain the second rod while allowing the second rod to slide axially and to change in pitch, yaw, and roll about a fourth pivot point; and a transverse coupler extending laterally between the first and second rods, the transverse coupler laterally constraining the first and second rods and preventing the first and second rods from changing in pitch, yaw, and roll relative to the transverse coupler.

Some aspects relate to a spinal correction system comprising: a rod configured to extend along a first side of a spine; a rod anchor configured to be secured to a first vertebra of the spine and to laterally constrain the first rod while allowing the first rod to slide axially and to change in pitch, yaw, and roll about a first pivot point; and a second rod anchor configured to be secured to a second vertebra of the spine and to laterally constrain the first rod and prevent the first rod from changing in at least pitch, yaw, and roll relative to the second rod anchor.

Some aspects relate to a method of correcting a spinal deformity of a patient's spinal column, the method comprising: securing a first rod anchor to a first vertebra of the patient's spine; securing a second rod anchor to a second vertebra of the patient's spine; coupling a first rod to the first rod anchor and the second rod anchor such that: the first rod is laterally constrained relative to the first rod anchor while being free to slide axially and to change in at least pitch, yaw, and roll relative to the first rod anchor; and the first rod is laterally constrained relative to the second rod anchor and is prevented from changing in at least pitch, yaw, and roll relative to the second rod anchor; securing a third rod anchor to a third vertebra of the patient's spine; securing a fourth rod anchor to a fourth vertebra of the patient's spine; and coupling a second rod to the third rod anchor and the fourth rod anchor such that: the second rod is laterally constrained relative to the third rod anchor while being free to slide axially and to change in at least pitch, yaw, and roll relative to the third rod anchor; the second rod is laterally constrained relative to the fourth rod anchor and is prevented from changing in at least pitch, yaw, and roll relative to the fourth rod anchor.

This summary is not meant to be limiting in nature. While multiple embodiments are disclosed, still other embodiments will become apparent to those skilled in the art from the following detailed description, which shows and describes various illustrative embodiments. Accordingly, the drawings and detailed description are to be regarded as illustrative in nature and not restrictive.

BRIEF DESCRIPTION OF THE DRAWINGS

FIG. 4 is an isometric view of the stabilizing anchor of FIG. 3 with an insertion sleeve in a retention orientation, according to some embodiments.

FIG. 5 is a plan view of the stabilizing anchor of FIG. 3 with the insertion sleeve in the retention orientation, according to some embodiments.

FIG. 6 is an isometric view of the stabilizing anchor of FIG. 3 with the insertion sleeve in an insertion orientation, according to some embodiments.

FIG. 7 is a plan view of the stabilizing anchor of FIG. 3, with the insertion sleeve in the insertion orientation, according to some embodiments.

FIG. 10 is an isometric view of another stabilizing anchor of the system of FIG. 1, according to some embodiments.

FIG. 13 is an isometric view of an actuation assembly of the system of FIG. 1, according to some embodiments.

FIG. 14 is a cross-section view of a portion of the actuation assembly of FIG. 12, according to some embodiments.

FIG. 15 is a bottom view of the actuation assembly of FIG. 12 with a portion of a clamshell housing removed, according to some embodiments.

FIG. 16 is a bottom view of the actuation assembly of FIG. 12, according to some embodiments.

FIG. 17 is a cross-sectional view of a connector head and tether of the actuation assembly of FIG. 13, according to some embodiments.

FIG. 18 is a cross-sectional view of the actuation assembly of FIG. 13, showing the connector head and tether in an extended state and a retracted state, according to some embodiments.

FIGS. 43-46 are side and rear views of a force directing member of the transverse coupler of FIG. 32 and the adjustment arm of FIG. 39 at various angulations, according to some embodiments.

FIGS. 47-49 show the transverse coupler of FIG. 32 at various stages of realignment, according to some embodiments.

FIGS. 57-59 show the transverse coupler of FIG. 55 at various stages of realignment, according to some embodiments.

FIG. 63 is a schematic illustration of an isometric view of a stabilizing anchor system, according to some embodiments.

FIG. 64 is an isometric perspective view of a stabilizing member of FIG. 63, according to some embodiments.

Figure 1:
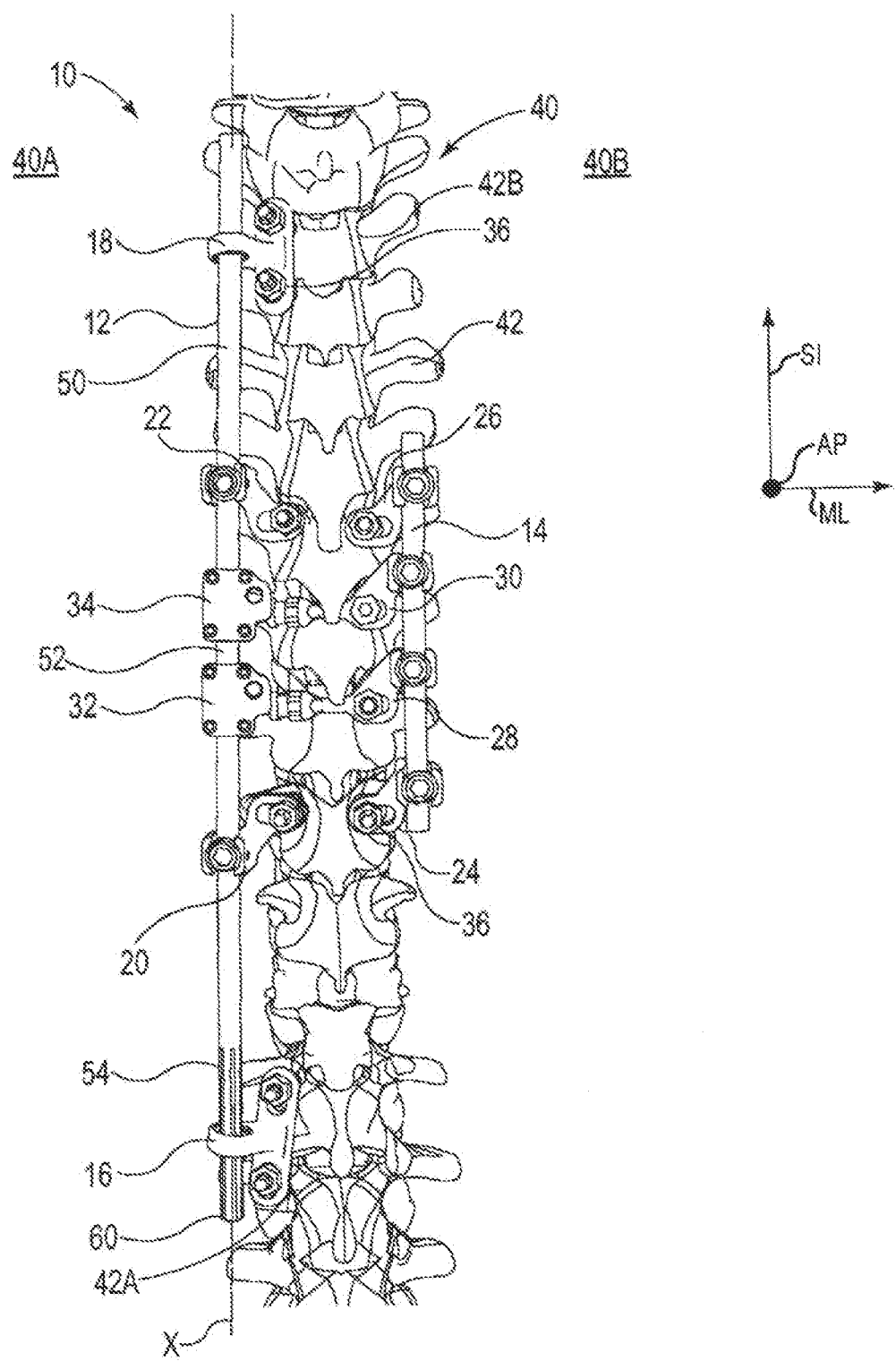
FIG. 1 is an isometric view of an implantable spinal correction and fusion system, according to some embodiments.

Various embodiments have been shown by way of example in the drawings and are described in detail below. As stated above, the intention, however, is not to limit the invention by providing such examples.

DETAILED DESCRIPTION

Some embodiments relate to a spinal correction and/or fusion system for implantation into a patient, as well as associated methods and devices. In general terms, the system provides for lateral translational corrective force(s) and/or derotational corrective force(s) on a spinal column. In some embodiments, the system includes instrumentation for facilitating vertebral fusion at a selected region of the spine; that is, fusing one or more vertebra of a spine to one or more other vertebra of the spine. In some other embodiments, the system provides for lateral translational corrective force(s) and/or derotational corrective force(s) on a spinal column without vertebral fusion; that is, without fusing any vertebra of a spine to any other vertebra of the spine. Some features of the system include implementation of a first, relatively longer rod for initial correction, and a second, shorter rod for secondary spinal stabilization. In some embodiments, the spine retains freedom of motion (in one or more degrees of freedom) above (superior to) and below (inferior to) the spinal segment corresponding to the shorter rod, with the first, relatively longer rod remaining implanted. In various embodiments, if desired, the secondary stabilization rod can be fastened such that the spinal segment corresponding to the shorter rod maintains freedom of motion (in one or more degrees of freedom) while still providing sufficient support and stabilization. In yet some other embodiments, if desired, the secondary stabilization rod can be fastened to promote a fusion process at one or more designated spinal segments, and thereby prohibit any freedom of motion at any of the one or more designated spinal segments. In yet some other embodiments, the system provides means for maintaining a correction to facilitate spinal remodeling in the absence of substantial vertebral fusion (e.g., without permanent vertebral fusion or without any vertebral fusion). In some embodiments the secondary stabilization rod extends along the same vertebral levels as the first, relatively longer rod (e.g., the second rod is substantially the same length as the first rod).

In some embodiments, the first, relatively longer rod is trimmed and/or removed following correction, remodeling and/or fusion of the spinal segment corresponding to the second, shorter rod. A variety of additional features and advantages of a spinal correction systems are contemplated and provided by the instant disclosure. As used herein, the phrase "as shown" is indicative of a feature or features shown in the accompanying drawings, although as noted it should be understood that additional or alternative features to those shown are contemplated.

FIG. 1 shows a spinal correction and fusion system 10, the system 10 including a first rod 12; a second rod 14; a plurality of anchors, including a first stabilizing anchor 16, a second stabilizing anchor 18, a first anchor 20, a second anchor 22, a third anchor 24, a fourth anchor 26; a first transverse anchor 28; a second transverse anchor 30; a first adjustment assembly 32; a second adjustment assembly 34; and a plurality of fasteners 36, such as bone screws, for securing components of the system 10 to a spine, or spinal column 40 having a first side 40A and a second side 40B. The system 10 is optionally used to bring the spine 40 to a more natural curvature (e.g., using a single adjustment). In other embodiments, an abnormal curvature in the spinal column 40 has been adjusted to a more natural curvature using other hardware, prior to or in conjunction with securing portions of the system 10 to the spinal column 40. In some embodiments, the system 10 is adapted to initially provide means for leveraged correction, with translation and/or derotation of the spine. If desired, the system 10 is adapted to provide means for selective fusion of the spine following correction. In other embodiments, the system 10 provides means for maintaining a correction to facilitate spine remodeling without vertebral fusion, or without permanent vertebral fusion.

Although the system 10 is shown with a select number of components, such as two stabilizing anchors 16, 18 two transverse anchors 28, 30, and two adjustment assemblies 32, 34, more or fewer are implemented as appropriate. For example, in some embodiments a single transverse anchor, such as the first transverse anchor 28, is secured to one or more of a plurality of vertebrae 42 at an apex A of a spinal deformation, with a corresponding adjustment assembly, such as the first adjustment assembly 32, coupled to the transverse anchor 28. Moreover, although four anchors 20, 22, 24, 26 are shown, in some embodiments there are more or less of the anchors. For example, in some embodiments the system 10 includes the first rod 12, the second rod 14, a single transverse anchor, such as the transverse anchor 28 and a single anchor, such as the third anchor 24, with the second rod 14 secured between the transverse anchor 28 and the third anchor 24. In still other embodiments, the system 10 does not include any of the anchors 20, 22, 24, 26, but instead the second rod 14 is secured between the first and second transverse anchors 28, 30 (see, e.g., FIG. 25). A variety of other configurations are also contemplated.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawing between a center and side of the body. The terms pitch, roll, and yaw are also used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane.

In various embodiments, changes in pitch, yaw, and/or roll occur concurrently or separately as desired. Additionally, in various embodiments, while pitch, yaw, and/or roll may occur, the system may be configured to permit any combination of pitch, yaw, and/or roll movement, or may alternatively permit only one of pitch, yaw, or roll, or may alternatively permit each of pitch, yaw, and roll. Accordingly, the various embodiments, discussed herein should not be considered limiting. Moreover, as used herein, "lateral translation" is not limited to translation in the medial-lateral direction unless specified as such.

As shown in FIG. 1, in some embodiments the first rod 12, also described as an elongate member, is secured to the spinal column 40 at a pre-selected offset from a longitudinal axis of the spinal column 40. For example, the first rod 12 is optionally secured at an offset along a medial-lateral axis ML, or right-left axis, and anterior-posterior axis AP, or back-front axis. In some embodiments, the first rod 12 is secured on the left side of the spinal column 40 as shown. As subsequently described, the offset is optionally selected to cause at least a relative lateral translation (e.g., central or medial movement and/or anterior posterior movement) and/or derotational shift (e.g., about a central axis of the spine) of selected vertebrae 42 of the spinal column 40 such that the spinal column 40 exhibits a more natural position.

Figure 21:
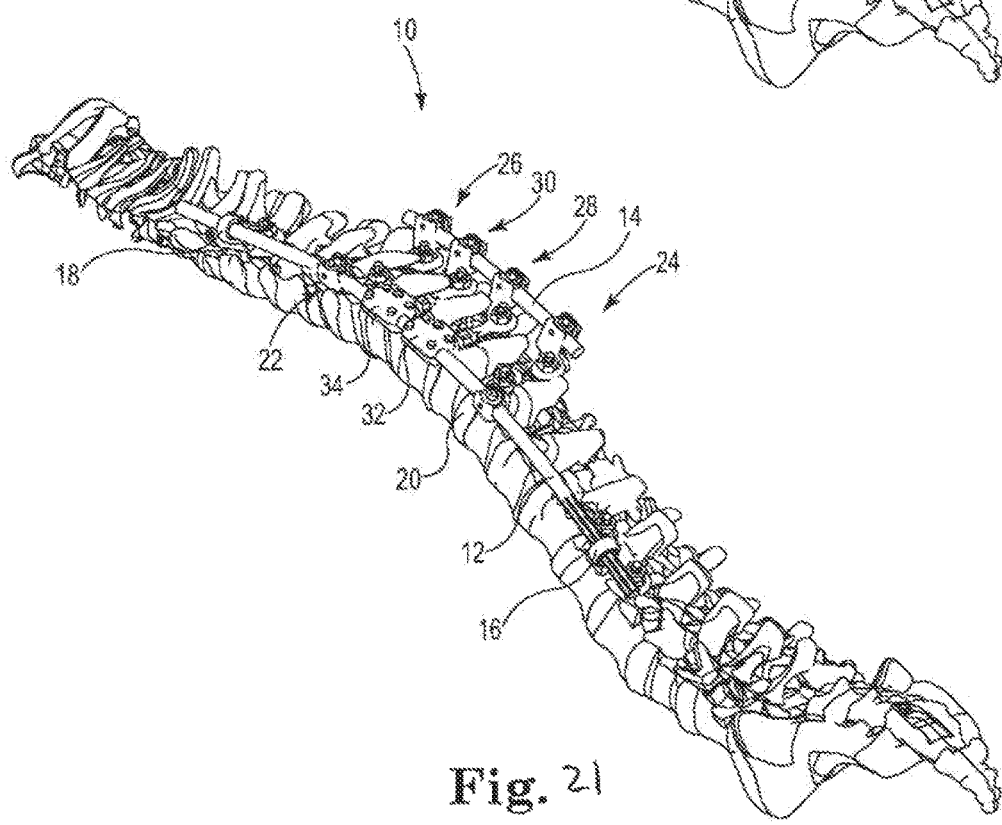

The first rod 12 is elongate and cylindrical and includes a superior portion 50, an intermediate portion 52, and an inferior portion 54. However, it should be appreciated that the cross-section of the rod (including any rod disclosed herein) may take on any suitable shape (including, but not limited to, a triangle, square, oval, rectangle, etc.) and is not therefore limited to a circular cross-section. In some embodiments, the first rod 12 is adapted, or otherwise structured, to extend along the spinal column 40. The first rod 12 is optionally contoured to complement a desired spinal curvature (e.g., generally following the curvature of a corrected, or natural spine, as shown in FIG. 21). In some embodiments, the first rod 12 is substantially rigid, defining a substantially round cross-section with a mean diameter of about 6 mm and being formed of a suitable biocompatible material, such as titanium alloy ASTM F136, or cobalt chromium alloy ASTM F1537 or any other suitable implantable material. If desired, the first rod 12 incorporates some flex, or springiness while substantially rigidly retaining its shape. Though some material examples have been provided, the first rod 12 is optionally formed of a variety of materials, including stainless steel or suitable polymeric materials as well as a variety of cross-sectional shapes.

As shown in FIG. 1, the first rod 12 has a longitudinal axis X—where the rod 12 is substantially straight, the longitudinal axis X is substantially straight and, where the rod 12 is substantially curved or angled, the longitudinal axis X is similarly curved or angled. The sections 50, 52, 54 of the first rod 12 are optionally continuously formed or are formed as separate, connected parts as desired. In still other embodiments, expandable rod designs are also contemplated.

As shown in FIG. 1, the first stabilizing anchor 16 and the first anchor 24 are adapted, or otherwise structured, to be mounted, or fixed to one or more vertebrae, such as vertebrae 41 and 42 located at or near inferior and apical regions, respectively, along the spine 40. Additional examples of stabilizing anchors and anchors in accordance with some embodiments of the system 10 are set forth in U.S. application Ser. No. 13/301,514, filed on Nov. 21, 2011 and entitled TRANSVERSE CONNECTOR FOR SPINAL STABILIZATION SYSTEM, and U.S. application Ser. No. 12/411,562, filed on Mar. 26, 2009 and entitled SEMI-CONSTRAINED ANCHORING SYSTEM, the entire contents of which are hereby incorporated by reference.

Figure 2:
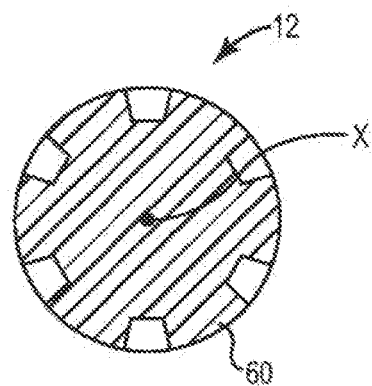
FIG. 2 is a cross-sectional view of a spinal rod of the system of FIG. 1, according to some embodiments.

FIG. 2 is a cross-sectional view of the first rod 12 in the inferior portion 54 of the first rod 12. As shown, the cross-sectional shape of the first rod 12, including various portions thereof, is not limited to circular cross-sections. For example, the inferior portion 54 optionally includes a plurality of splines 60 for mating with the first stabilizing anchor 16. As shown in FIG. 2, the splines 60 are trapezoidal (e.g., similarly to the teeth of a gear) with rounded bases, although a variety of shapes, such as involute shapes, are contemplated.

As shown in FIG. 1, the second rod 14 is substantially shorter than the first rod 12. For example, the second rod 14 is optionally configured (e.g., having a corresponding length and/or longitudinal contour) to extend along an apical region A of the spine 40 and/or between a desired number of anchors, such as the third and fourth anchors 24, 26. The second rod 14 is optionally formed of similar materials and with similar cross-section(s) to that of the first rod 12, as desired.

FIGS. 3 to 8 show the first stabilizing anchor 16 (also described as a rod anchor) of the system 10, according to some embodiments. As shown in FIG. 1, the first stabilizing anchor 16 is adapted, or otherwise structured, to be mounted, or fixed to one or more of the vertebrae 42, such as a first vertebra 42A (FIG. 1) located at an inferior position, or other position, along the spine 40.

Figure 3:
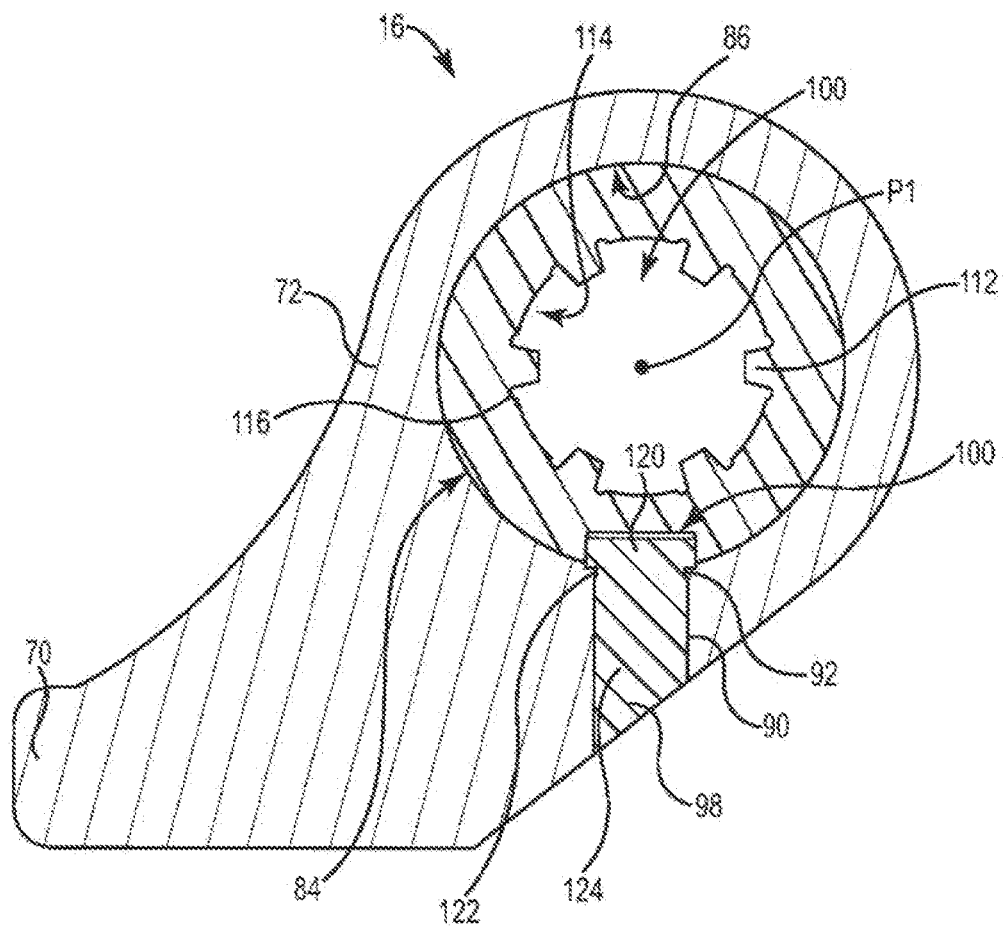
FIG. 3 is a cross-sectional view of a stabilizing anchor of the system of FIG. 1, according to some embodiments.

As shown in FIG. 3, the first stabilizing anchor 16 is adapted to receive, and includes means for receiving, the first rod 12 such that the first rod 12 is secured laterally, against lateral translation relative to the first stabilizing anchor 16. In some embodiments, the first rod 12 is substantially prevented from translating in a direction substantially perpendicular to the longitudinal axis X at a first pivot point P1. In turn, the first rod 12 is able to slide axially, or translate axially, along the longitudinal axis X of the first rod 12, relative to the first stabilizing anchor 16 through the first pivot point P1. In some embodiments, the rod 12 is also able to change in pitch and/or yaw about the first pivot point P1. In yet other embodiments, the first stabilizing anchor 16 is additionally/alternatively adapted, or otherwise structured, to limit rotation, or roll, of the first rod 12 about the longitudinal axis X of the first rod 12. In some embodiments, the first stabilizing anchor 16 provides means for allowing the rod 12 to angulate without substantial lateral translation relative to the first stabilizing anchor 16 and without substantial rotation about the longitudinal axis X.

FIG. 4 is an isometric view of the first stabilizing anchor 16, according to some embodiments. As shown, the first stabilizing anchor 16 is optionally formed of biocompatible materials and includes a mounting portion 70 and a housing portion 72. The mounting portion 70 is adapted to secure the first stabilizing anchor 16 to one or more vertebrae 42, such as the first vertebra 42A and an additional vertebra 42 above (superior to) or below (inferior to) the first vertebra 42A. In other embodiments, the mounting portion 70 is secured to a single vertebra, such as the first vertebra 42A (e.g., laterally across the first vertebra 70B at the pedicles, or at a single point—such as a single pedicle—on the first vertebra 26A. In some embodiments, the mounting portion 70, also described as a plate, is adapted to be secured at two or more points, for example spanning between two vertebrae 42 (e.g., the L3-L4 vertebrae) or spanning across a portion of a single vertebra 42 (e.g., pedicle-to-pedicle on a single vertebra).

In some embodiments, the mounting portion 70 includes a pedestal with first and second anchor locations, each of the anchor locations defining a surface suitable for mounting the first stabilizing anchor 16 to one or more vertebrae 42. The first and second anchor locations each optionally include through holes 74 for receiving one of the fasteners 36, such as a pedicle screw or similar device to secure the mounting portion 70 to one or more vertebrae 42, such as the first vertebra 42A.

In some embodiments, the housing portion 72 is of a multi-piece design (FIGS. 2 to 9). In some other embodiments, the housing portion 72 is formed from a single piece and includes a passage having a revolute, convex surface (FIGS. 10a and 10b). In a multi-piece housing design, as shown in FIG. 4, the housing portion 72 of the first stabilizing anchor 16 includes a body 80 and a sleeve insert 82. In some embodiments, the sleeve insert 82 is substantially spherical in shape and the body 80 forms a substantially spherical mating race for receiving the sleeve insert 82. The body 80 has a sleeve aperture 84 (FIG. 5) extending front-to-back through the body 80, the sleeve aperture 84 defining a revolute, substantially concave articulation surface 86 (FIG. 5). The sleeve insert 82, in turn, forms a complementary revolute, substantially convex articulation surface 88. As shown in FIG. 3, the body 80 also has a pin chase 90 (e.g., a cylindrical through hole) that defines a terminal seat 92 having a larger diameter than a remainder of the pin chase 90.

Figure 8:
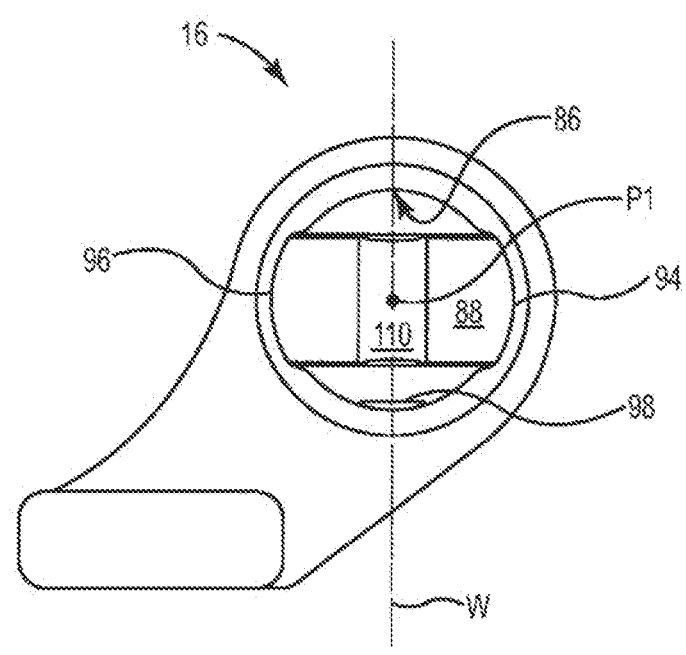
FIG. 8 is a front view of the stabilizing anchor of FIG. 3, with the insertion sleeve in the insertion orientation, according to some embodiments.

FIG. 5 is a plan view of the first stabilizing anchor 16, showing the sleeve insert 82 as it would be received within the body 80 (though normally hidden from view). As shown, the concave articulation surface 86 of the aperture 84 defines opposed apices 89 on each side of the articulation surface 86. The articulation surfaces 86, 88 are adapted, or otherwise structured, to form a substantially complementary fit with one another, such that the sleeve insert 82 is able to be captured by the body 80 within the aperture 94 and have relative angular movement with respect to the body 80. To facilitate assembly of the sleeve insert 82 into the body 80, the aperture 84 includes first and second channels 94, 96 formed into the articulation surface 86 at the apices 89 such that the minimum effective internal diameter D of the aperture 84 is increased between the channels 94, 96. The channels 94, 96 extend front to back through the body 80 and are positioned on opposite sides of the body 80. While two channels are shown, in other embodiments a single channel is included. FIG. 8 is a front view of the stabilizing anchor 16. As shown in FIGS. 5 and 8, the channels 94, 96 have arcuate profiles and extend into the aperture 84 to the apices 89 on each side of the articulation surface 86. The profiles of the channels 94, 96 are optionally complementary in shape to a portion of the profile—the lateral edges, or sides—of the sleeve insert 82 such that the sleeve insert 82 is able to be received through the channels 94, 96 into the aperture 84 when the sleeve insert 82 is oriented perpendicular, or edgewise relative to the body 80. The body 80 also includes a protrusion 98 (FIG. 3) (e.g., a pin) or protrusions (not shown) that extends inwardly into the aperture 84 from the articulation surface 86.

As shown in FIG. 3, the sleeve insert 82 has a passage 100 defining the pivot point P1 through which the splined, or inferior portion 54 of the first rod 12 is able to be slidably received. The sleeve insert 82 also has a groove 110 extending parallel to the center line of the sleeve insert into the convex articulation surface 88. The groove 110 is adapted to receive the protrusion 98 for limiting roll of the sleeve insert 82 within the body 80. The pivot point P1 is defined in the passage 100, where upon assembly the first rod 12 passes through the first pivot point P1 such that the longitudinal axis of the rod at the first pivot point P1 is generally concentric with the center of the passage 100.

As shown, the passage 100 has a non-circular cross-section (e.g., a splined cross-section corresponding to the inferior portion 54 of the first rod 12). Upon mating the non-circular cross-sections of the first rod 12 and the passage 100, rotation of the first rod 12 relative to the sleeve insert 82 is substantially inhibited or prevented. In some embodiments, the passage 100 defines a plurality (e.g., six) of inward splines 112 and a plurality of recessed pockets 114 (e.g., six) between the splines 112. The splines 112 are optionally trapezoidal (e.g., like the teeth of a gear) in shape overall. A variety of shapes are contemplated for the splines 112, including involute shapes, for example. The pockets 114 optionally include corner recesses 116 that are rounded in shape (e.g., to help prevent binding between the passage 100 and the first rod 112 during sliding of the first rod 112 in the passage 100). In some embodiments, the splines 60, 112 are designed to help maximize efficiency of torque transfer between the first rod 12 and the sleeve insert 82 while reducing contact pressure angle(s) between the components.

The protrusion 98 is optionally a pin with a head 120, a neck 122, and a body 124, the neck 122 being located between the head 120 and the body 124. The head 120, the neck 122, and the body 124 are optionally substantially cylindrical with the head 120 having a greater diameter than the body 124 and the body 124 having a greater diameter than the neck 122. The protrusion 98 is received in the pin chase 90 with the head 120 received in the seat 92 such that the head projects into the aperture 84. In some embodiments the protrusion 98 is press fit into the pin chase 90 and/or welded, adhered, or otherwise secured within the pin chase 90. In other embodiments the protrusion is temporary and is removable, providing temporary prevention of roll of the sleeve insert 82 within the body 80 so that the first stabilizing anchor 16 is able to be adjusted so that the rod 12 is free to rotate.

FIGS. 6, 7, and 8 show the sleeve insert 82 being assembled into the body 80 by positioning the sleeve insert 82 perpendicular, or edgewise, relative to the aperture 84 (FIG. 5) and sliding the sleeve insert 82 into the channels 94, 96. In other embodiments, the sleeve insert 82 is able to be inserted at another angle (45 degrees, for example). In this position, the diametric plane of the sleeve insert 82 is generally parallel to the centerline Z of the aperture 84. In alternate terms, the centerline W of the sleeve insert 82 is generally parallel to the diametric plane of the aperture 84. Once received in the aperture 84 via the channels 94, 96, the sleeve insert 82 is rotated such that the protrusion 98 (FIG. 3) is received in the groove 110 (e.g., as shown in FIGS. 3, 4, and 5). With the protrusion 98 slidably received in the groove 110, the pitch and yaw of the first rod 12 are still able to change while roll is substantially limited. The first rod 12 also remains free to slide axially within the sleeve insert 82, according to some embodiments.

As relative rotation between the sleeve insert 82 and the body 80 is also substantially inhibited, relative rotation between the first rod 12 and the first stabilizing anchor 16 is substantially inhibited or limited, allowing the first rod 12 to be maintained at a pre-selected rotational position relative to the first stabilizing anchor 16. It also should be understood that other cross-sectional shapes for each of the passage 100 (FIG. 3) and first rod 12 can be selected to allow some degree of rotation about the longitudinal axis X within a predefined range.

Figure 9A:
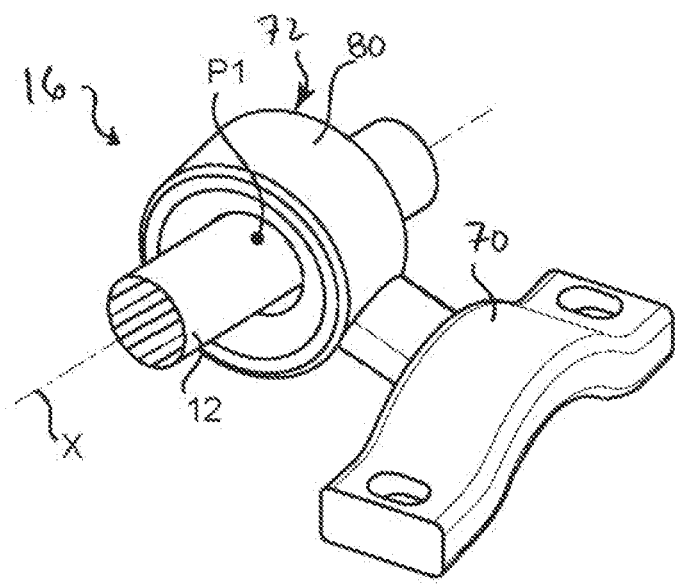
FIGS. 9A and 9B show features of another anchor of the system of FIG. 1, according to some embodiments.
Figure 9B:
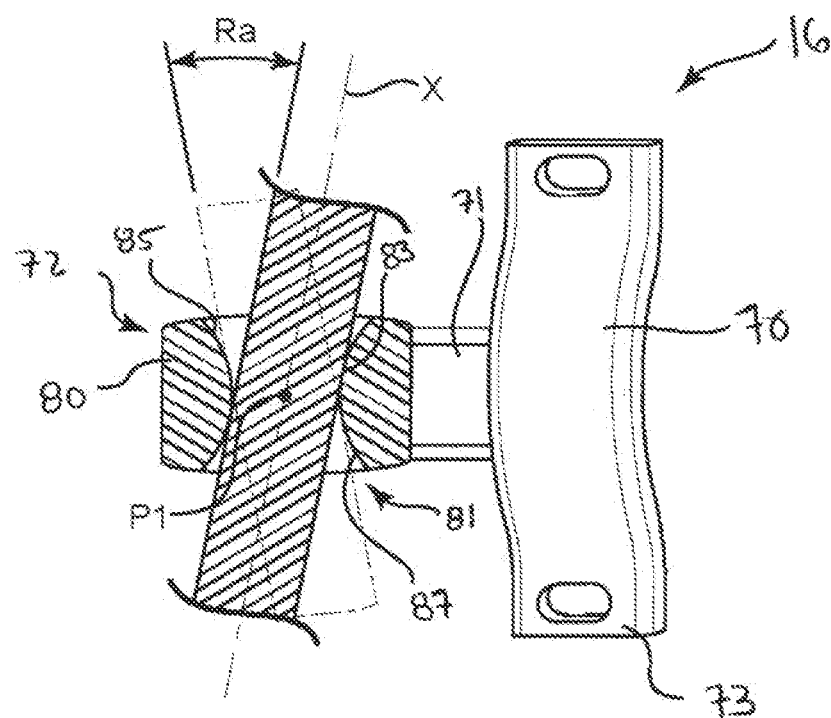

As discussed above, in some embodiments, the housing portion 72 is formed from a single piece. For example, as shown in FIGS. 9a and 9b, the housing 72 includes a body 80. According to some embodiments, the body 80 is generally ring shaped and forms a passage 81 having a revolute, convex surface 83. Specifically, as shown in FIG. 9b, convex surface 83 includes an upper curve 85 and a lower curve 87. The body 80 is adapted to allow the rod 12 to pass through the passage 81 at the first pivot point P1, where the passage 81 defines a minimum effective diameter (e.g., providing appropriate clearance between the rod 12 and body 80) that allows the rod 12 to slide through passage 81. The passage 81 also allows the rod 12 to rotate and angulate about the longitudinal axis X at the first pivot point P1 while minimizing lateral translation or inhibiting substantial lateral translation. In at least this manner, the rod 12 is able to rotate and angulate about the longitudinal axis X at the first pivot point while lateral translation of the rod 12 with respect to the body 80 is substantially limited in all planes. In alternate terms, the rod 12 is able to slide within the passage 81 and change in yaw, pitch, and roll at the first pivot point P1, while being constrained from side-to-side movement within the passage 81 at the first pivot point P1.

In some embodiments, the second stabilizing anchor 18 is substantially similar to the first stabilizing anchor 16, including any desired combination of previously-described features. As shown in FIG. 10, the second stabilizing anchor 18 is substantially similar to the first stabilizing anchor 16, with the exception that the second stabilizing anchor 18 has a smooth bore 130 for receiving the first rod 12. The second stabilizing anchor 18 is adapted to be fixed, and provides means for fixation to a second vertebra, such as a second vertebra 42B (FIG. 1). The second stabilizing anchor 18 is further adapted to receive, and provides means for receiving the first rod 12 (FIG. 1) such that the second stabilizing anchor 18 limits translational movement of the first rod 12 except along the longitudinal axis X (i.e., the second stabilizing anchor 18 allows sliding movement of the first rod 12) and allows the first rod 12 to change in at least pitch and yaw about a second pivot point P2. Moreover, as shown the second stabilizing anchor 18 allows the first rod 12 to change in roll about the second pivot point P2.

Figure 11:
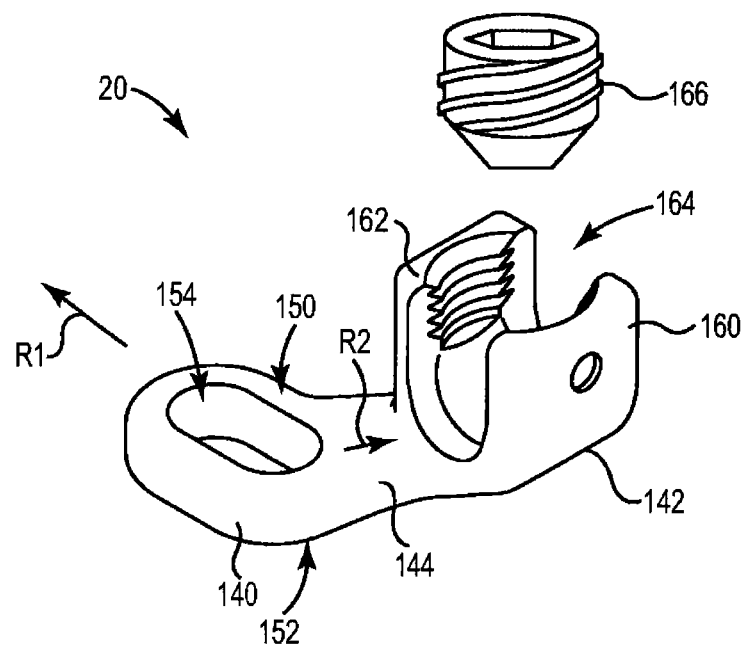
FIG. 11 is an isometric view of an anchor of the system of FIG. 1, according to some embodiments.

The first anchor 20 is shown in greater detail in FIG. 11, according to some embodiments. The first, second, third, and fourth anchors 20, 22, 24, 26 (FIG. 1) are optionally substantially similar, and thus various features of the anchors are described in association with the first anchor 20, where when referenced, features of the first anchor 20 are designated with reference numbers and similar features of the second, third, and fourth anchors 22, 24, 26 are designated with the same reference numbers followed by a "B," "C," and "D," respectively.

As shown, the first anchor 20 includes a mounting portion 140, a head portion 142, and a connection portion 144. The mounting portion 140 has a top surface 150, a bottom surface 152, and a slot 154 for receiving one of the fasteners 36, such as a pedicle screw or other bone screw. The slot 154, also described as an aperture, is elongate and extends longitudinally in a first direction R1.

The head portion 142 is substantially U-shaped, including a first prong 160 and a second prong 162 defining a pocket 164 for receiving one of the first and second rods 12, 14. As shown, the prongs 160, 162 are threaded for receiving a clamping screw 166 adapted to engage and secure one of the first and second rods 12, 14 immobilized within the pocket 164.

The connection portion 144 extends in a second direction R2 that is offset from the first direct R1. The connection portion 144 extends between the mounting portion 140 and the head portion 142 at an angle of about 45 degrees, for example, relative to the first direction R1.

The first and second transverse anchors 28, 30 are optionally substantially similar, and thus various features of both the first and second transverse anchors are described in association with the first transverse anchor 28, where when referenced, features of the first transverse anchor 28 are designated with reference numbers and similar features of the second transverse anchor 30 are designated with the same reference numbers followed by a "B."

Figure 12:
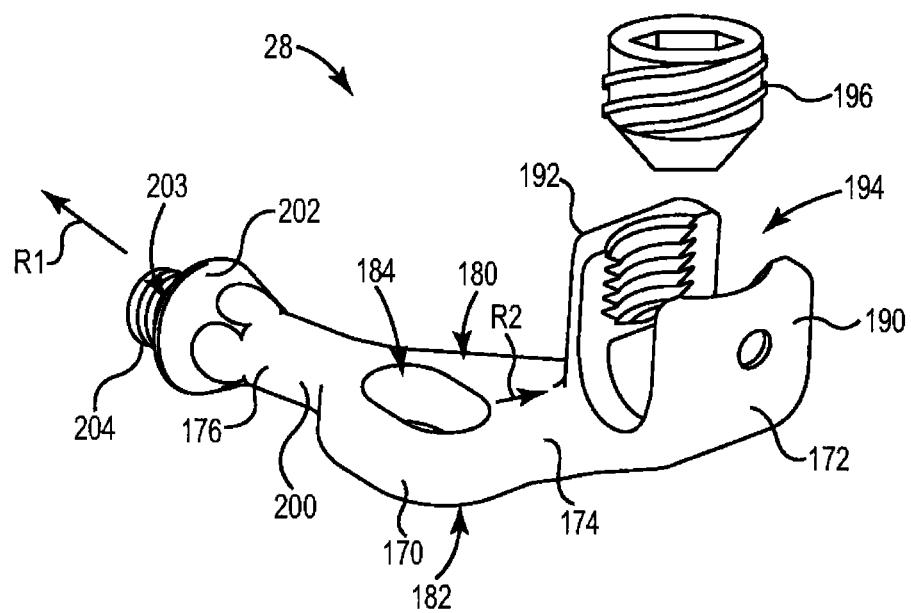
FIG. 12 is an isometric view of a transverse anchor of the system of FIG. 1, according to some embodiments.

The first transverse anchor 28 is shown in greater detail in FIG. 12, according to some embodiments. As shown, the first transverse anchor 28 includes a mounting portion 170, a head portion 172, a connection portion 174, and an arm portion 176. The mounting portion 170 has a top surface 180, a bottom surface 182, and a slot 184 for receiving one of the fasteners 36, such as a pedicle screw. The slot 184 is elongate and extends longitudinally in a first direction R1. In some embodiments, the arm portion 176 generally extends away from the mounting portion 170 for purpose of coupling to the first rod 12 and the head portion serves to couple the first transverse anchor 28 to the second rod 14.

The head portion 172 is substantially U-shaped, including a first prong 190 and a second prong 192 defining a pocket 194 for receiving the second rod 14. As shown, the prongs 190, 192 are threaded for receiving a clamping screw 196 adapted to engage and secure the second rod 14 immobilized within the pocket 194.

The connection portion 174 extends in a second direction R2 that is offset from the first direct R1. The connection portion 174 extends between the mounting portion 170 and the head portion 172 at an angle of about 45 degrees, for example, relative to the first direction R1. In other embodiments, the connection portion 174 extends between the mounting portion and head portion 170, 172 at another angle, such as from about 30 to about 60 degrees, or at no angle (i.e., the portions 170, 172, 174 are generally in-line with one another).

The arm portion 176 includes a neck section 200 that is substantially elongate and cylindrical, a shoulder section 202 that is flared and defines an abutment face 203, and a terminal section 204 that is threaded. The arm portion 176 extends longitudinally in the first direction R1. The arm portion 176 is adapted to extend across a portion of one of the vertebrae 42 for example, from one side of the spinal column 40 to an opposite side of the spinal column 40. For example, the first transverse anchor 28 is secured to one of the vertebrae 42 such that the arm portion 176 extends laterally across the vertebra 42.

FIG. 13 shows the first adjustment assembly 32 from an isometric view, FIG. 14 shows the adjustment 32 assembly from a cross-sectional view, FIG. 15 shows the adjustment assembly 32 from a plan view with a portion of the housing removed, and FIG. 16 shows the adjustment assembly 32 from a plan view with the housing intact, according to some embodiments.

The first adjustment assembly 32 is adapted to adjust, and provides means for adjusting tension and/or a distance between the first rod 12 and the first transverse anchor 28. The first and second adjustment assemblies 32, 34 are optionally substantially similar. Thus, various features of both the first and second adjustment assemblies 32, 34 are described in association with the first adjustment assembly 32, where features of the first adjustment assembly 32 are designated with reference numbers and similar features of the second adjustment assembly 34 are designated with the same reference numbers followed by a "B."

As shown, the first adjustment assembly 32 includes a tensioner 208, the tensioner 208 including a housing 210, a reel 212, a circumferential gear 214 surrounding the reel 212, a drive gear 216 in contact with the circumferential gear 214, and an actuation head 218. The first adjustment assembly 32 also includes an elongate connector 219 adapted to be wound about the reel 212.

The reel 212, as well as the circumferential gear 214 and drive gear 216 are maintained at least partially within the housing 210. In turn, the housing 210 is adapted to be secured to the first rod 12. For example, the housing 210 optionally forms a central lumen 220 through which the rod first 12 is receivable. Upon inserting the first rod 12 through the central lumen 220, the housing 210 is adapted to be clamped onto the first rod 12.

In some embodiments, the housing 210 defines a first side 223 and a second side 224 and incorporates a clamshell design (e.g., a first portion adjustably secured to a second portion) adapted to be tightened onto the first rod 12 (e.g., using one or more fasteners). Thus, in some embodiments, the first adjustment assembly 32 is substantially fixed with respect to the first rod 12. Other designs, such as monolithic housing designs and others are contemplated. Moreover, in some embodiments, the first adjustment assembly 32 is movable with respect to the first rod 12, for example being able to slide and/or rotate about the first rod 12.

The central lumen 220 of the housing 210 defines a longitudinal axis L and forms a pocket 226 for receiving the reel 212 and the circumferential gear 214 such that the reel 212 and the circumferential gear 214 are able to rotate within the housing 210. The housing 210 also defines a pair of opposed apertures 228 for receiving ends of the drive gear 216 to retain the drive gear 216 while allowing the drive gear 216 to rotate. As shown, the housing 210 also defines a top 230 and a bottom 232, where the bottom 232 forms a lower opening 234 and a raised abutment 236 adjacent to the lower opening 234, toward the first side 223 of the housing 210.

As shown, the reel 212 includes a helical groove 238 for receiving the elongate connector 219 and a raised anchor block 240 for securing the elongate connector 219 to the reel 212. For example, the anchor block 240 optionally includes an aperture for receiving the elongate connector 219 and is welded or otherwise fastened in the aperture. The reel 212, as well as the circumferential gear 214, form a lumen 242 for coaxially receiving the first rod 12. In some embodiments, by receiving the first rod 12 through the reel 212 and circumferential gear 214, an overall size, or profile, of the tensioner 208 is able to be reduced.

As shown, the circumferential gear 214 is connected to, and coaxially aligned with the reel 212. The circumferential gear 214 is engaged with the drive gear 216 such that rotation of the drive gear 216 causes the circumferential gear 214, and thus, the reel 212, to turn (e.g., in a worm or crossed-spur gear configuration).

The elongate connector 219 includes a flexible tether 250 and a connector head 252. In some embodiments, the flexible tether 250 is substantially flexible and able to be pivoted in a multiple directions and/or be spooled or wound, for example. Suitable flexible materials include wire and stranded cables, monofilament polymer materials, multifilament polymer materials, multifilament carbon or ceramic fibers, and others. In some embodiments, the flexible tether 250 is formed of cobalt chromium alloy or titanium alloy wire or cable, although a variety of materials are contemplated. The flexible tether 250 includes a terminal cap 256 (FIG. 17) adapted to be secured in the connector head 252. The terminal cap 256 has a rounded (e.g., semi-circular) head and is optionally swaged onto the flexible tether 250. In other embodiments, rather than a swage a loop or other feature is implemented to connect to the connector head 252.

FIG. 17 is a cross-sectional view of the connector head 252, according to some embodiments. As shown, the connector head 252 defines an internal bore 260 and forms a collar 262, a raised shoulder 264, and a neck 266. The internal bore 260 has a rounded seat 270 (e.g., a substantially concave seat). The connector head 252 also has a first end 272 and a second end 274, the second end 274 having a rounded inner profile 276 (like the horn of a trumpet). The flexible tether 250 is secured to the connector head 252 by receiving the terminal cap 256 in the rounded seat 270 in a complementary fit.

The elongate connector 219, also described as a connector or cable, is adapted to be secured to the first transverse anchor 28 and the first adjustment assembly 32. So secured, the elongate connector 219 defines an effective length between the first transverse anchor 28 and tensioner 208 and, and thus the first rod 12 (although, in some embodiments, the elongate connector 219 is secured directly to the rod 12). As described, in some embodiments, the tensioner 208 is adapted to modify, and provides means for modifying, the effective length of the tether 250 of the elongate connector 219 (e.g., by spooling the tether 250 on and off of the reel 212).

The elongate connector 219 is attached or secured to the reel 212 and passes out of the housing 210 through the lower opening 234 in the housing 210. Although a lower opening is shown, in other embodiments the opening is in the side or top, for example. Actuation of the drive gear 216 via the actuation head 218 turns the circumferential gear 214, which turns the reel 212, thus winding (or unwinding, depending on the direction in which the reel 212 is turned) the elongate connector 219 about the reel 212. Rotation of the reel 212 in the appropriate direction draws the tether 250 in toward the tensioner 208 (FIG. 18), pulling the first transverse anchor 28 toward the tensioner 208, according to some methods of correcting a spinal defect.

FIG. 18 shows the first actuation assembly 32 as it would appear in a first, extended state attached to the uncorrected spinal column 40 (e.g., FIG. 19) and as it would appear in a second, retracted state as attached to the corrected spinal column (e.g., FIG. 20), according to some embodiments. As shown, the connector head 252 engages the raised abutment 236 and the housing 210 as the tether 250 is drawn into the housing 210. This engagement and/or the orientation of the lower opening 234 (i.e., with the tether 250 exiting the housing 210 through the bottom) helps generate a moment M on the first transverse anchor 28 (not shown in FIG. 18) thereby helping to derotate the third vertebra 42C to which the first transverse anchor 28 is attached. The ability of the tether 250 to flex and bend at the second end 274 of the connector head 252 helps generate a polyaxial connection at the second end 274 and facilitates generation of the moment M as described.

Figure 19:
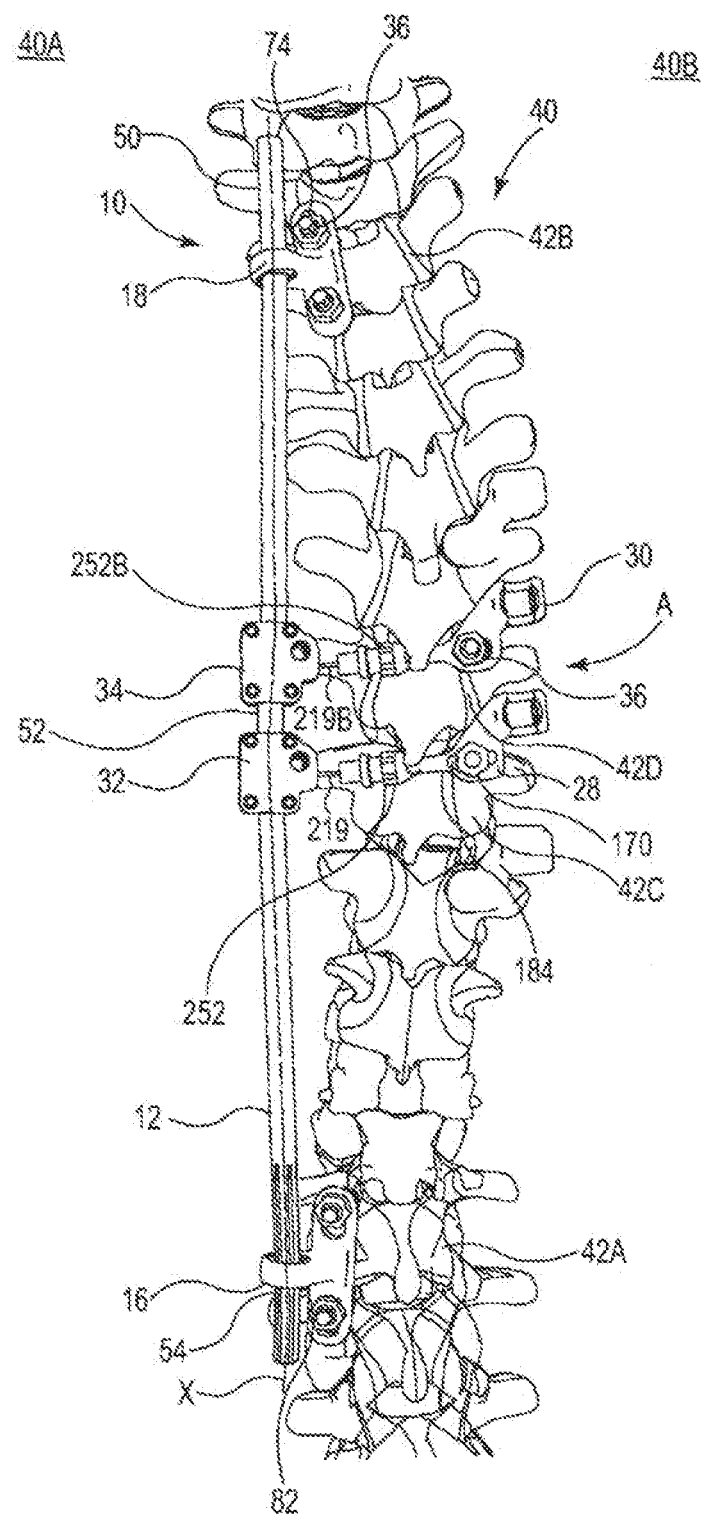
FIG. 19 is an isometric view of the system of FIG. 1 during a correction procedure, according to some embodiments.

FIG. 19 shows the assembled system 10. In some embodiments, assembly of the system 10 and associated methods of correcting the spine 40 include securing the stabilizing anchors 16, 18 to inferior and superior portions of the spine 40. For example, the first stabilizing anchor 16 is optionally secured to the spine 40 by driving one of the plurality of fasteners 36 through each of the through holes 74 and into one or more of the vertebrae 42. For example, as shown in FIG. 1, the first stabilizing anchor 16 is secured with one of the fasteners 36 driven into a pedicle of the first vertebra 42A and another of the fasteners 26 driven into a pedicle of another vertebra that is adjacent to the first vertebra 42A. The second stabilizing anchor 18 is similarly secured to the second vertebra 42B and a vertebra adjacent the second vertebra 42B. As shown, each of the first and second stabilizing anchors is secured on the first side 40A of the spine.

The first and second actuation assemblies 32, 34 are slid onto or otherwise coupled to the first rod 12 and then secured (e.g., clamped) at a desired location along the rod 12. The first rod 12 is received in the first and second stabilizing anchors 16, 18, with the splined, or inferior portion 54 of the first rod 12 slidably received in the sleeve insert 82 of the first stabilizing anchor 16 and the superior portion 50 of the rod 12 slidably received in the second stabilizing anchor 18. Thus, in some embodiments the first rod 12 extends along the first side 40A of the spine 40 and is secured against lateral movement relative to a portion of the spine 40.

In some embodiments, the first rod 12 is attached by the stabilizing anchors 16, 18 to pedicles and/or transverse processes on the first side 40A of the spinal column 40 and is able to slide axially relative to the first and/or second stabilizing anchors 16, 18. In other embodiments, the rod 12 is attached by the stabilizing anchors 16, 18 to the second side 40B of the spinal column 40, on different sides of the spinal column 40 (e.g., the first stabilizing anchor 16 on the left side and the second stabilizing anchor 18 on the right side), or along the mid-line of the spinal column 40. In other embodiments, the first rod 12 is adjustable length to compensate for changes in length of the spinal column 40.

By limiting rotation, or roll, of the first rod 12 relative to the first stabilizing anchor 16, the bend in the first rod 12 is oriented and maintained in a desired rotational position. Maintaining the rotational orientation at one end (i.e., at the first stabilizing anchor 16) is useful, for example, to help ensure that the bend or shape of the rod 12 consistently follows or otherwise appropriately tracks a desired curvature of a spinal column 40. Freedom of rotation at the other end of the first rod 12 (i.e., at the second stabilizing anchor 18), however, still permits the spinal column 40 to have more natural movement while the corrective forces are being applied.

Though not shown, the system 10 optionally includes one or more stop features for limiting axial sliding, or translation of the first rod 12 relative to one of the stabilizing anchors to a desired range. Generally, sliding of the first rod 12 in a particular axial direction is substantially limited, or arrested, when a stop feature engages, or abuts an adjacent stabilizing anchor 16, though other stop mechanisms are contemplated.

The first and second transverse anchors 28, 30 are secured to one or more of the vertebrae 42, such as a third vertebra 42C in an apical region A of the spine 40 and a fourth vertebra 42D in an apical region A of the spine 40. The first transverse anchor 28 is secured to the third vertebra 42C by driving one of the fasteners 36 through the slot 184 in the mounting portion 170 of the first transverse anchor 28. For example, the first transverse anchor 28 is optionally secured into a pedicle and/or transverse processes of the third vertebra 42C on the second side 40B of the spine 40. The second transverse anchor 30 is optionally similarly secured on the second side of the spine 42B to a pedicle of the fourth vertebra 42D. As shown, the arm portions 176, 176B (FIG. 12) of the first and second transverse anchors 28, 30 extend from the second side 40B of the spine 40 to the first side 40A of the spine 40.

The first and second actuation assemblies 32, 34 are secured to the first and second transverse anchors 28, 30 by attaching (e.g., screwing) the connector heads 252, 252B of the elongate connectors 219, 219B to the threaded terminal sections of the transverse anchors 28, 30. Some methods include adjusting a curvature of the spine 40 to a desired curvature using the actuation assemblies 32, 34. For example, the tensioners 208, 208B of the first and second actuation assemblies 32, 34 are actuated (independently or simultaneously) in order to draw the elongate connectors 219, 219B into the respective tensioners 208, 208B, thereby drawing the third and fourth vertebrae 42C, 42D and surrounding portions of the spine 40 toward the first rod 12 and to a more desirable spinal curvature.

Figure 20:
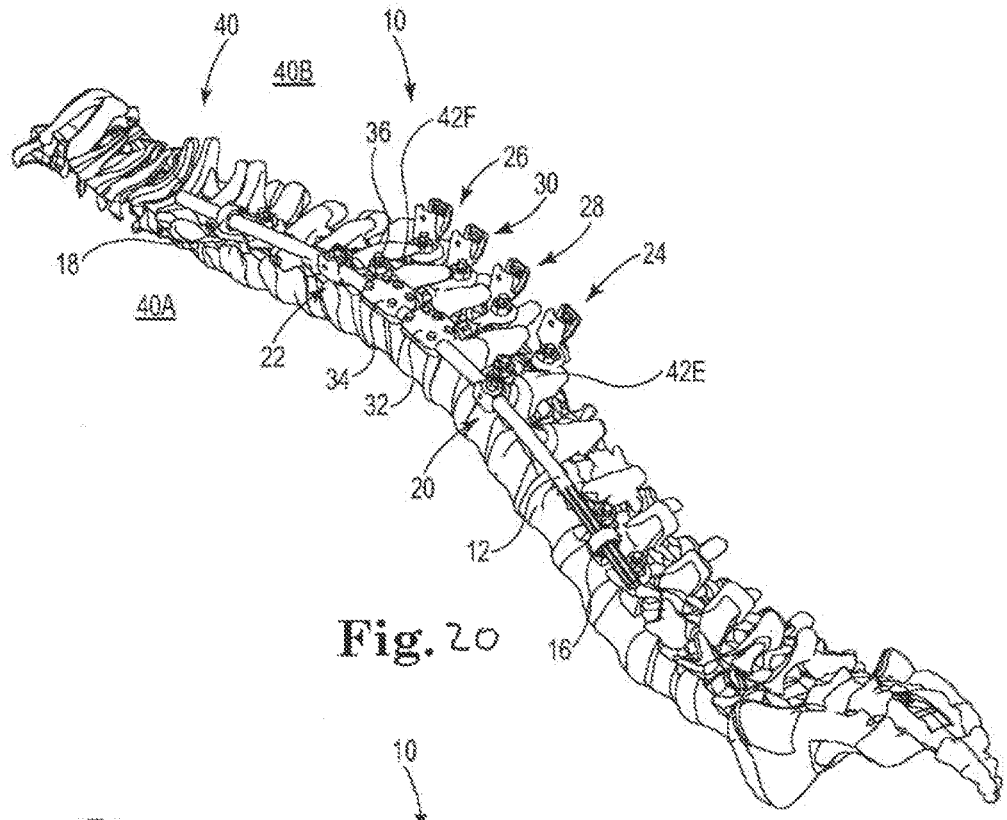
FIGS. 20 and 21 are isometric views of the system of FIG. 1 before and after assembly of a second rod into the system, according to some embodiments.

As shown in FIG. 20, the first and third anchors 20, 24 are secured to a fifth vertebra 42E and the second and fourth anchors 22, 26 are secured to a sixth vertebrae 42E, 42F of the spine 40, thought each of the connectors is optionally secured to a different vertebra. The first anchor 20 is secured along the spine 40 at a location between the first stabilizing anchor 16 and the first actuation assembly 32 and the second stabilizing anchor 18 is secured at a location between the second stabilizing anchor 18 and the second actuation assembly 34. The first and second anchors 20, 22 are secured on the first side 40A of the spine 40 whereas the third and fourth anchors 24, 26 are secured on the second side 40B of the spine 40 opposite the first and second anchors 20, 22, for example. The first anchor 20 is secured to a pedicle of the fifth vertebra 42E by driving one of the fasteners 36 into the pedicle through the slot 154 in the mounting portion 140 of the first anchor 20. The second, third, and fourth anchors 22, 24, 26 are optionally similarly secured to the spine 40.

If desired, the first rod 12 is received in the first and second anchors 20, 22 (e.g., prior to securing the first and second anchors 20, 22 to the spine 40) and the first rod 12 is secured in the pocket 164 of the first anchor 20 using the clamping screw 166 (FIG. 11). The first rod 12 is similarly secured in the second anchor 22, thereby immobilizing the first rod 12 between the first and second anchors 20, 22.

As shown in FIG. 21, the second rod 14 is received in the transverse anchors 28, 30, and optionally in the third and fourth anchors 24, 26 (e.g., prior to securing the third and fourth anchors 24, 26 to the spine 40) in order to provide secondary stabilization to the corresponding region of the spine 40. For example, the second rod 12 is secured in the pocket of the third anchor 24 using the clamping screw and in the pocket 194 of the first transverse anchor 28 using the clamping screw 196 (FIG. 12). The second rod 14 is similarly secured in the second transverse anchor 30 and the fourth anchor 26, thereby immobilizing the second rod 14 between the third and fourth anchors 24, 26. As shown, the first and second rods 12, 14 are on opposite sides of the spine 40, immobilizing a desired region of the spine 40 (e.g., as part of a spinal fusion process), such as an apical region A of the spine 40. As appropriate, bone cement, fillers, or other materials are optionally employed with one or more vertebrae 42 to facilitate intervertebral fusion. In other embodiments, the system 10 is configured to avoid fusion of the spine 40. For example, the first and/or second rods 12, 14 are optionally substantially flexible such that the system 10 allows sufficient movement of the spine 40 to help avoid intervertebral fusion while still providing structural support during growth and remodeling of the spine 40.

Figures 22, 23, 24:
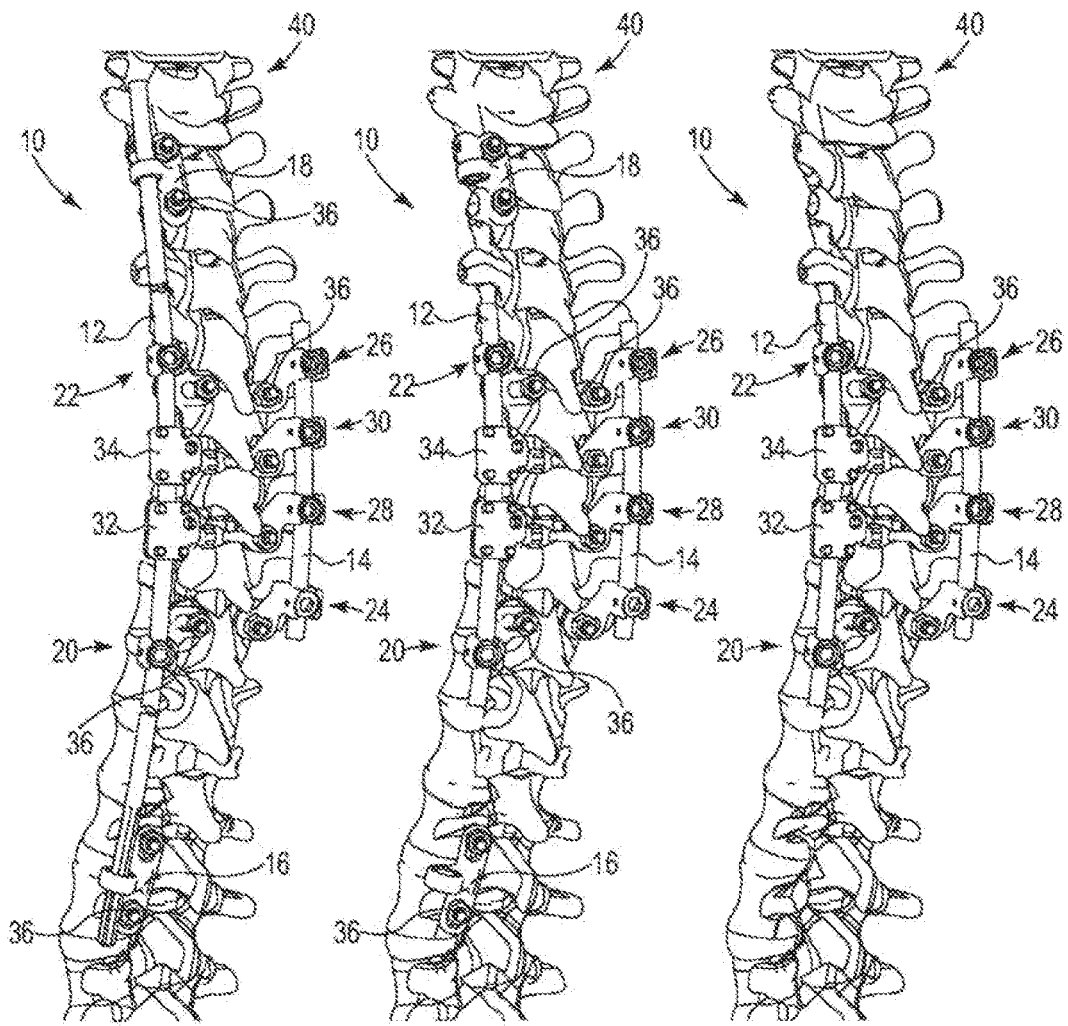
FIGS. 22 to 24 are isometric views of the system of FIG. 1 showing a process of separating and removing portions of the first rod and stabilizing anchors, according to some embodiments.

As shown in FIG. 22, if desired (e.g., once the spine 40 is stabilized), the first rod 12 is clipped, cut, broken, or otherwise portioned between the first anchor 20 and the first stabilizing anchor 16 and between the second anchor 22 and the second stabilizing anchor 18. As shown in FIG. 23, the superior and inferior portions of the first rod 12 are optionally removed from the first and second stabilizing anchors 16, 18 and the first and second stabilizing anchors 16, 18 are removed from the spine 40. As another alternative, the first rod 12 is not portioned and is left free to move in the stabilizing anchors 16, 18, for example. Moreover, if desired, the entire system 10 is optionally removed after a desired amount of fusion of the spine has been achieved and/or after sufficient growth and remodeling of the spinal curvature has been achieved. For example, once a diseased area of the spine has sufficiently healed (e.g., after being fused and stabilized) the stability provided by the system 10 may no longer be required.

Thus, according to various embodiments, the spinal column 40 (and thus, the person) is able to twist, bend side-to-side, and bend forward-and-backward in a more natural manner while corrective forces are being applied to the spinal column 40 and/or to achieve a desired correction of the spine 40. In some embodiments, the effective lengths of the actuation assemblies 34, 36, and specifically the elongate connectors 219, 219B are adjusted (e.g., periodically or all at one time), bringing the spinal column into natural alignment, while the system 10 facilitates a more natural movement of the spinal column 40 (e.g., twisting and bending forward-and-backward and side-to-side) due to the freedom of movement afforded by the system 10. During a secondary fusion procedure, the second rod 14 is secured to the corrected spine 40 opposite first rod 12 to rigidly secure a region of the spine for fusion as shown in FIG. 24. If desired, this includes immobilizing an apical region A of the spine 40 and leaving a superior region of the spine 40 adjacent to the apical region A and an inferior region of the spine 40 adjacent to the apical region A free to move in at least one degree of freedom. The at least one degree of freedom optionally includes elongation, or growth, compression, twisting, and/or flexing. In some embodiments, the freedom of movement of the first rod 12 provided by the stabilizing anchors 16, 18 helps facilitate this motion. In other embodiments, removal of one or more portions of the system 10 (e.g., clipping and removing portions of the rod 12) facilitates this motion.

In some embodiments, by linking the convex and concave sides of the spine 40 together, stress on the spine 40 is distributed at the anchor-vertebral interfaces as well as stiffening the apical region A of the spine, helping to stabilize the deformity. Thus, in addition to the connection between the apical region A and the first rod 12, the lateral connection between the rods 12, 14 optionally helps resist vertebral rotation and lateral translation).

As previously indicated, in some embodiments, the spine 40 is optionally corrected, or tensioned toward the first rod 12 prior to securing the second rod 14 to the spine 40. In other embodiments, the corrective method includes securing the second rod 14 to the spine 40 (e.g., to partially or fully correct spinal curvature the apical region A) and then tensioning the second rod 14 toward the first rod 12 in order to correct the spine 40 or portions thereof (e.g., a curvature of the spine 40 superior and/or inferior to the apical region A).

Figure 25:
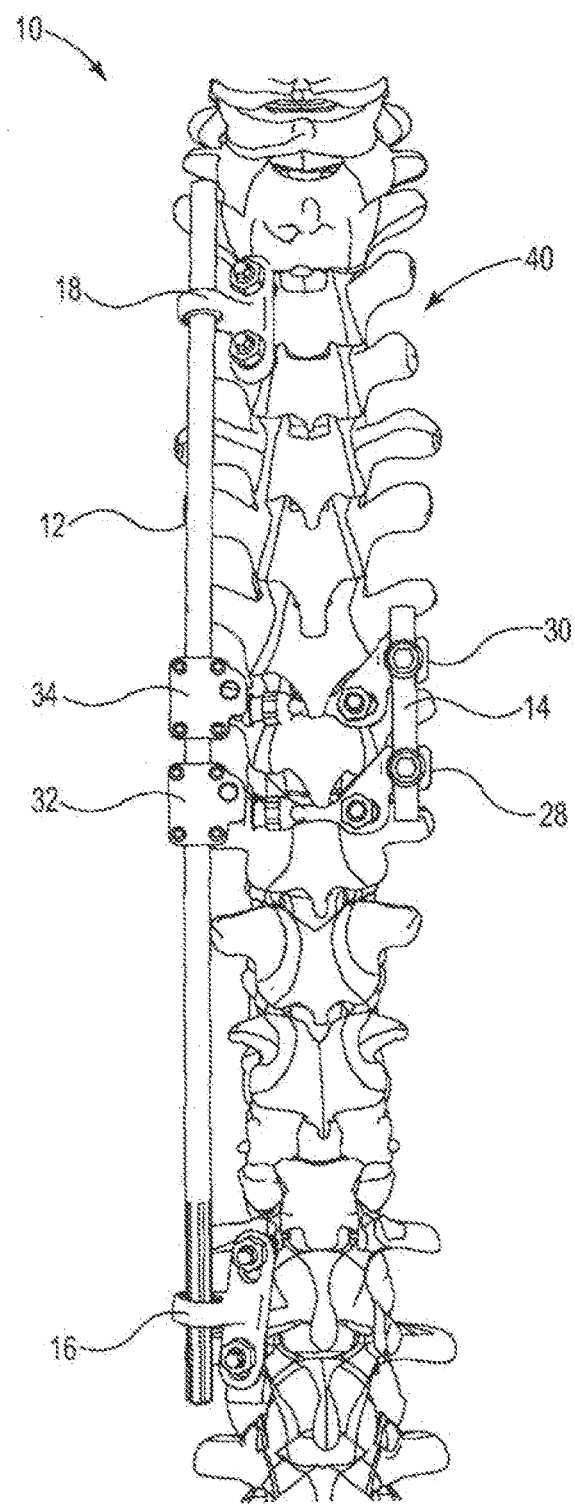
FIG. 25 is an isometric view of a system of another configuration, according to some embodiments.

As previously indicated, the system 10 may include greater or fewer components according to various embodiments. FIG. 25 is an example of the system 10, which includes correction and secondary stabilization features, the system 10 including fewer components. With reference to FIG. 19, the system 10 is optionally used to correct a spinal deformity (including a total or partial correction) and then the second rod 14 is received in, and secured in, the pockets 194, 194B of the first and second transverse anchors 28, 30. The secondary stabilization provided by the second rod 14 is optionally used to facilitate fusion of the spine 40, including use of growth promoters or other materials for encouraging intervertebral fusion.

Figure 26:
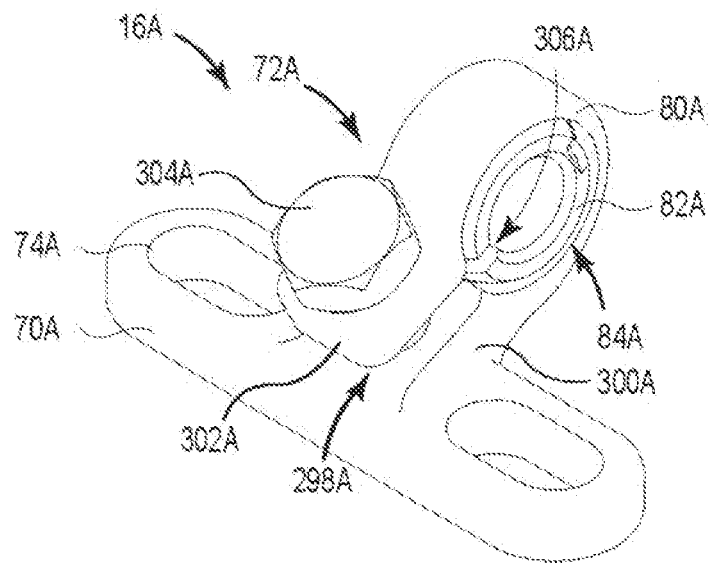
FIG. 26 is an isometric view of another anchor of an implantable spinal correction and fusion system, according to some embodiments.

FIG. 26 shows another stabilizing anchor 16A (also described as a rod anchor) of the system 10, according to some embodiments. The first stabilizing anchor 16A is adapted, or otherwise structured, to be mounted, or fixed to one or more of the vertebrae 42, such as a first vertebra 42A (FIG. 1) located at an inferior position, or other position, along the spine 40.

As shown, the first stabilizing anchor 16A is substantially similar to the first stabilizing anchor 16. The first stabilizing anchor 16A includes a mounting portion 70A and a housing portion 72A. The mounting portion 70A optionally includes through holes 74A for receiving one of the fasteners 36, such as a pedicle screw or similar device to secure the mounting portion 70A to one or more vertebrae 42, such as the first vertebra 42A.

The housing portion 72A of the first stabilizing anchor 16A includes a body 80A and a sleeve insert 82A. The body 80A is substantially similar to the body 80 of the first stabilizing anchor 16 with an optional difference being that the body 80A is split by a gap 298A dividing the body 80A into a lower portion 300A and an upper portion 302A that can be clamped together with adjustment member 304A (e.g., a bolt) secured across the gap 298A. The sleeve insert 82A, in turn, is substantially similar to the sleeve insert 82 with the addition of a gap 306A that facilitates clamping of the sleeve insert 82A onto the rod 12. For example, upon sufficiently tightening the adjustment member 304A, the sleeve insert 82A is clamped onto rod 12 to arrest sliding and rolling motion of the rod 12 through the sleeve insert 82A. Additionally, the clamping action of the body 80A on the sleeve 82A arrests changes in pitch and yaw. In different terms, the rod 12 is able to be selectively locked relative to the stabilizing anchor 16A.

Figure 27:
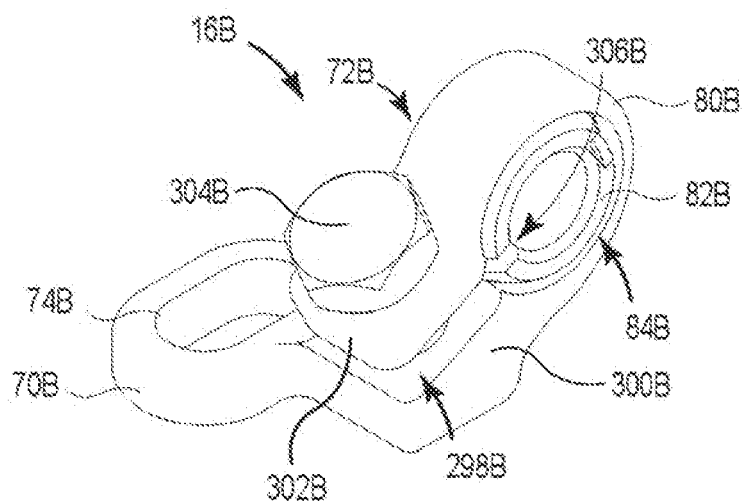
FIG. 27 is an isometric view of another anchor of an implantable spinal correction and fusion system, according to some embodiments.

FIG. 27 shows another stabilizing anchor 16B (also described as a rod anchor) of the system 10, according to some embodiments. The first stabilizing anchor 16B is adapted, or otherwise structured, to be mounted, or fixed to one or more of the vertebrae 42, such as a first vertebra 42A (FIG. 1) located at an inferior position, or other position, along the spine 40.

As shown, the first stabilizing anchor 16B is substantially similar to the first stabilizing anchors 16, 16A and includes a clamping mechanism similar to first stabilizing anchor 16A. The first stabilizing anchor 16B includes a mounting portion 70B and a housing portion 72B. The mounting portion 70B differs from the mounting portion 70A of the first stabilizing anchor 16A in that the mounting 70B portion includes a single through hole 74A for receiving one of the fasteners 36, such as a pedicle screw or similar device to secure the mounting portion 70B to one or more vertebrae 42, such as the first vertebra 42A. In some embodiments, the first stabilizing anchor 16B is adapted to be secured to a single vertebra, as compared to being secured across multiple vertebrae.

Figures 28, 29:
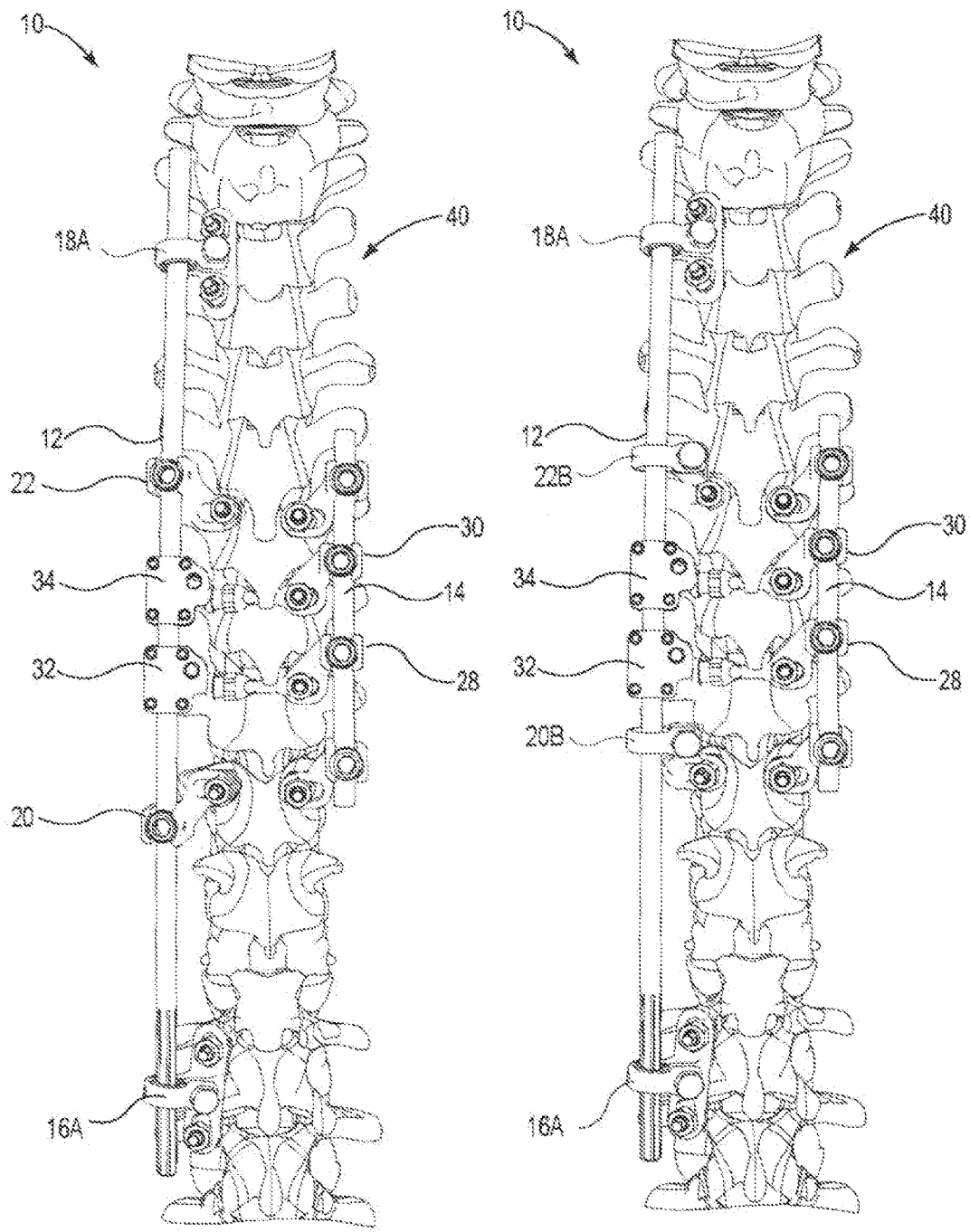
FIG. 28 shows another configuration for an implantable spinal correction and fusion system, according to some embodiments.
FIG. 29 shows another configuration for an implantable spinal correction and fusion system, according to some embodiments.

FIG. 28 shows the system 10 employing the first stabilizing anchor 16A and a second stabilizing anchor 18A that is substantially the same as the first stabilizing anchor 16A, according to some embodiments. As shown in FIG. 28, the rod 12 of the system 10 is able to slide and change in pitch, yaw, and roll at both of the anchors 16A, 18A and is also able to be selectively locked against sliding, pitch, yaw, and roll at each of the first and second stabilizing anchors 16A, 18A. Selective locking at one or both anchors 16A, 18A is optionally employed for a variety of reasons, including for performing partial or total fusion, to facilitate a correction, or adjustment process using the tensioners 32, 34, or to facilitate assembly of the system 10 prior to a correction operation.

FIG. 29 shows the system 10 employing the first and second stabilizing anchors 16A, 18A similarly to FIG. 28, according to some embodiments. In addition, the first anchor 20 and the second anchor 22 shown in FIG. 28 are replaced by first and second anchors 20B, 22B, which are each substantially the same as the first stabilizing anchor 16B (FIG. 27). As shown in FIG. 29, the rod 12 of the system 10 is able to slide and change pitch, yaw and roll at the anchors 16A, 18A, 20B, 22B and is also able to be selectively locked against sliding, pitch, yaw, and roll at each of the anchors 16A, 18A, 20B, 22B as desired. Once again, selective locking at any of the anchors 16A, 18A, 20B, 22B is optionally employed for a variety of reasons, including for performing partial or total fusion, to facilitate a correction, or adjustment process using the tensioners 32, 34, or to facilitate assembly of the system 10 prior to a correction operation.

Figure 30:
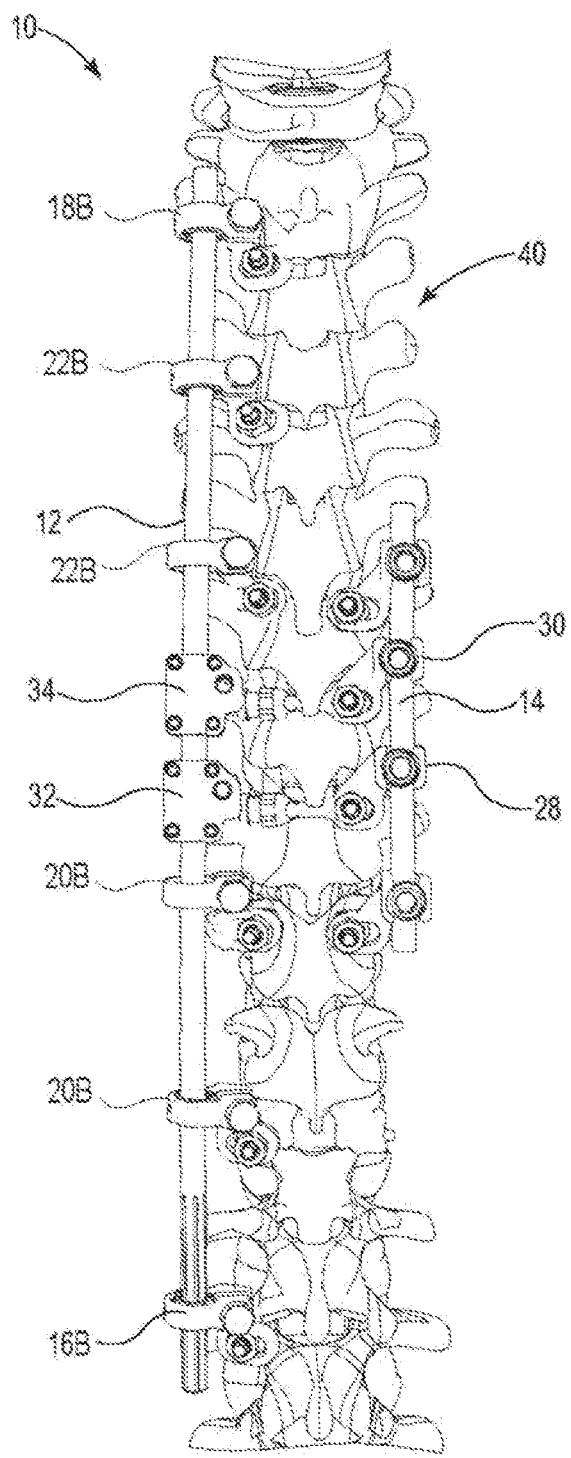
FIG. 30 shows another configuration for an implantable spinal correction and fusion system, according to some embodiments.

FIG. 30 shows the system 10 employing a plurality of anchors, each of which is substantially similar to the first stabilizing anchor 16B (FIG. 27). As shown in FIG. 30, the rod 12 of the system 10 is able to slide and change in pitch, yaw and roll at the anchors 16B, 18B, 20B, 22B. The first anchor 16B optionally employs a chase feature similar to those previously described to limit roll. Alternatively, the first anchor 16B freely permits roll of the rod 12. As shown in FIG. 30, the rod 12 has a high degree of freedom, while being laterally constrained, as desired. In particular, the rod 12 is also able to be selectively locked against sliding, pitch, yaw, and roll at each of the anchors 16B, 18B, 20B, 22B as desired. Once again, selective locking at any of the anchors is optionally employed for a variety of reasons, including for performing partial or total fusion, to facilitate a correction, or adjustment process using the tensioners 32, 34, or to facilitate assembly of the system 10 prior to a correction operation. From the foregoing, it should be understood that a variety of numbers and configurations of the anchors is contemplated. Though not specifically shown, it should also be understood that any of the foregoing anchors are employed with the second rod 14 on the second side of the spine.

While the spinal correction system configurations discussed above include one or more adjustment assemblies for lateral coupling, in various alternative embodiments discussed in greater detail below, the spinal correction system may additionally/alternatively include one or more transverse couplers for lateral coupling.

Figure 31:
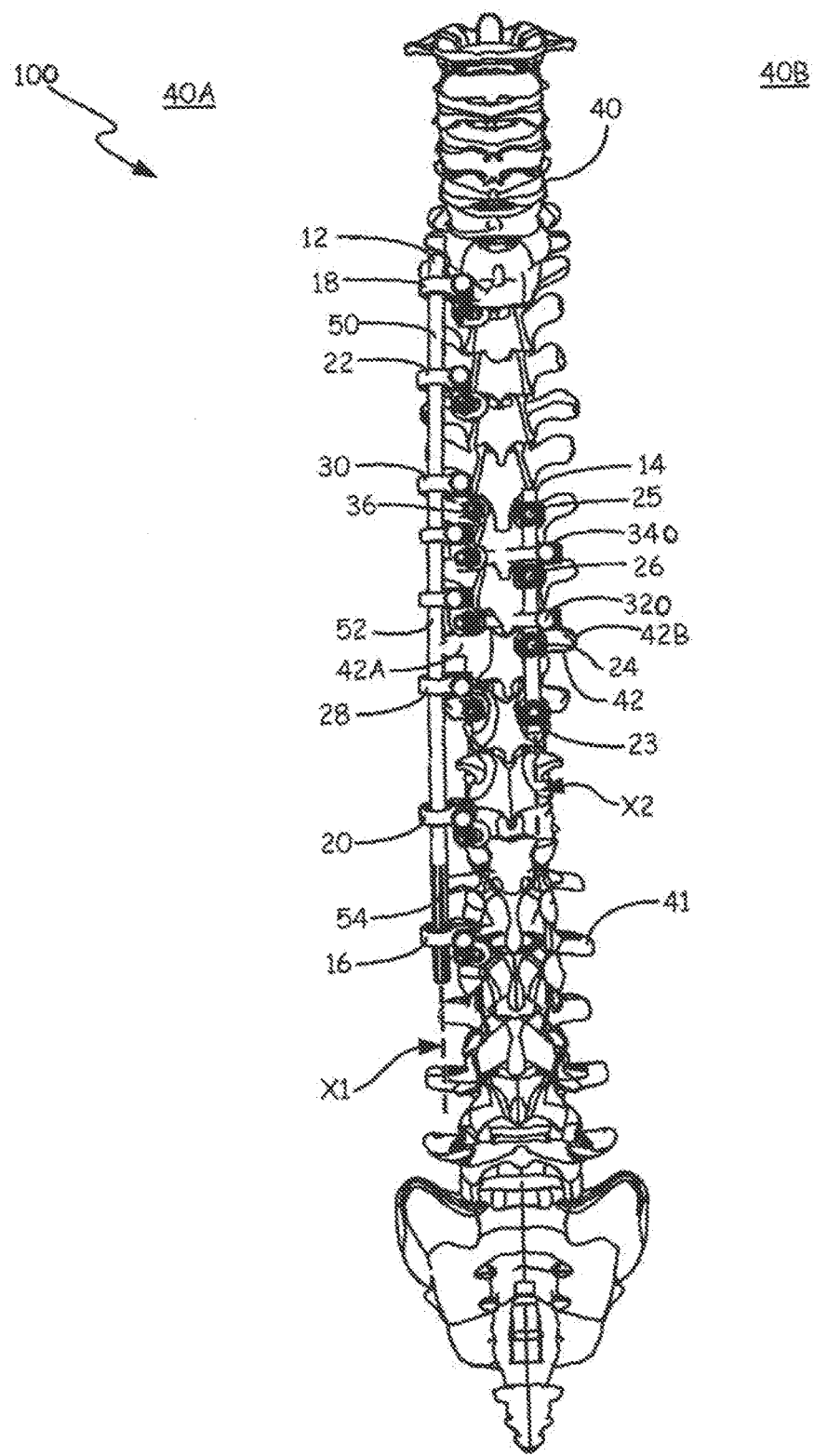
FIG. 31 is a schematic illustration of an implantable spinal correction and fusion system, according to some embodiments.

Similar to those embodiments discussed above, the spinal correction system 100 discussed below includes a first rod 12 (as described above), a second rod 14 (as described above), and plurality of stabilizing anchors. However, in some embodiments, the spinal correction system 100 additionally/alternatively includes one or more transverse couplers. For example, as shown in FIG. 31, in lieu of the above-discussed adjustment assemblies 32, the spinal correction system 100 includes transverse couplers (such as transverse couplers 320 and 340). While the subsequent embodiments utilize transverse couplers in lieu of the above-discussed adjustment assemblies 32 it should be appreciated that one or more of the below discussed transverse couplers 320 may be implemented or otherwise utilized in combination with one or more of the above-discussed adjustment assemblies 32.

The system 100 is optionally used to bring the spine 40 to a more natural curvature (e.g., prior to or as a part of a single adjustment or multiple adjustments). In some embodiments, an abnormal curvature in the spinal column 40 has been adjusted to a more natural curvature using other instrumentation, prior to or in conjunction with securing portions of the system 100 to the spinal column 40. In some embodiments, the system 100 is adapted to provide means for leveraged correction, with translation and derotation of the spine 40. If desired, the system 100 is adapted to provide means for selective fusion of the spine 40 following correction. In other embodiments, the system 100 provides means for maintaining a correction to facilitate spinal remodeling in the absence of substantial vertebral fusion (e.g., without permanent vertebral fusion or without any vertebral fusion).

Although the system 100 is shown in FIG. 31 with a selected number of components, such as six stabilizing anchors 16, 18, 20, 22, 23, 25, four anchors 24, 26, 28, 30, two transverse couplers 320, 340, more or fewer components are implemented as appropriate. For example, in some embodiments, the system 100 includes the first rod 12, the second rod 14, a single transverse coupler, such as the first transverse coupler 320, and a first anchor, such as the first anchor 24, with the first rod 12 secured by the first transverse coupler 320 and the second rod 14 secured between the first transverse coupler 320 and the first anchor 24. A variety of other configurations are also contemplated.

As shown in FIG. 31, the first rod 12 has a longitudinal axis X1—where the rod 12 is substantially straight, the longitudinal axis X1 is substantially straight and, where the rod 12 is substantially curved or angled, the longitudinal axis X1 is similarly curved or angled.

Figure 32:
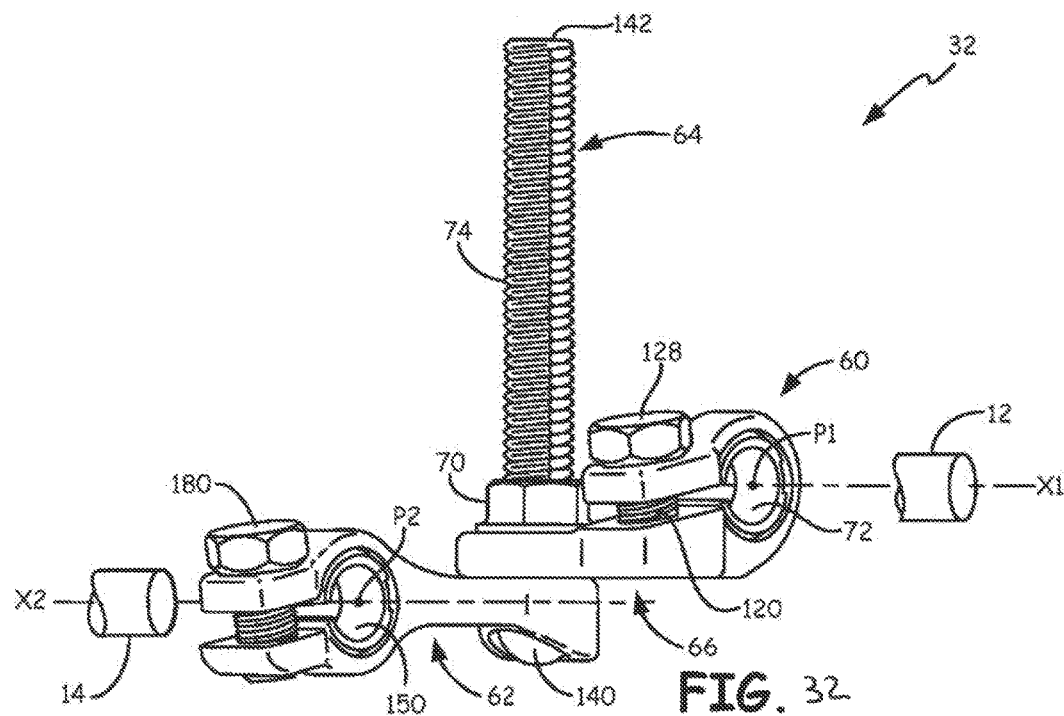
FIG. 32 is an isometric view of a transverse coupler of the system of FIG. 31, according to some embodiments.
Figure 33:
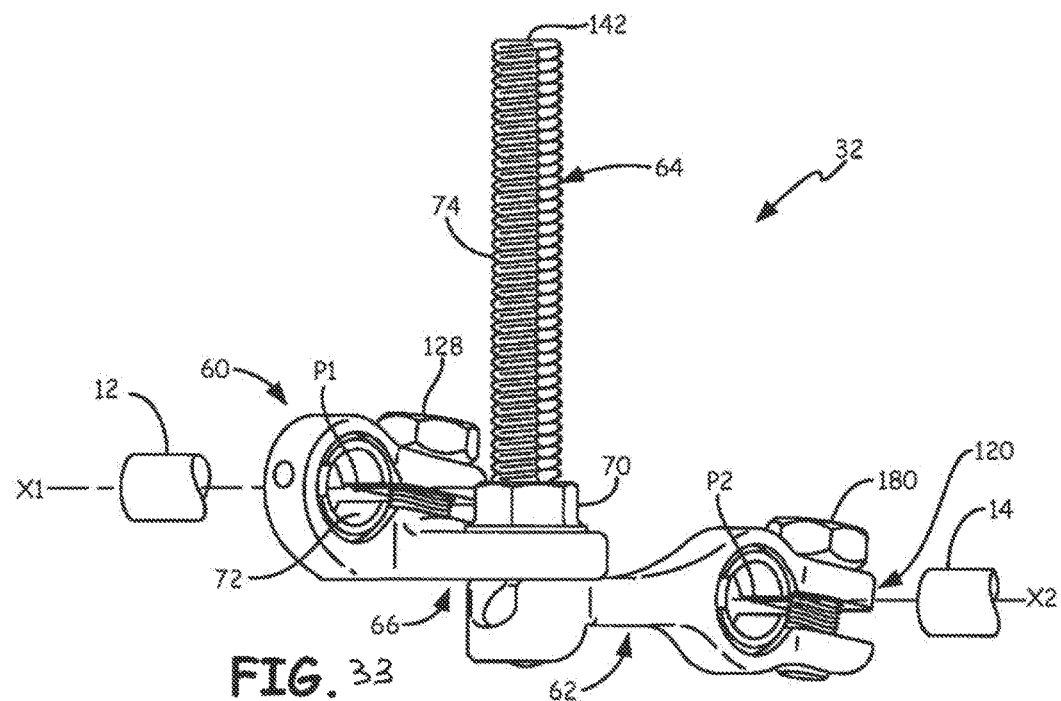
FIG. 33 is an isometric view of the transverse coupler of FIG. 32, according to some embodiments.
Figure 34:
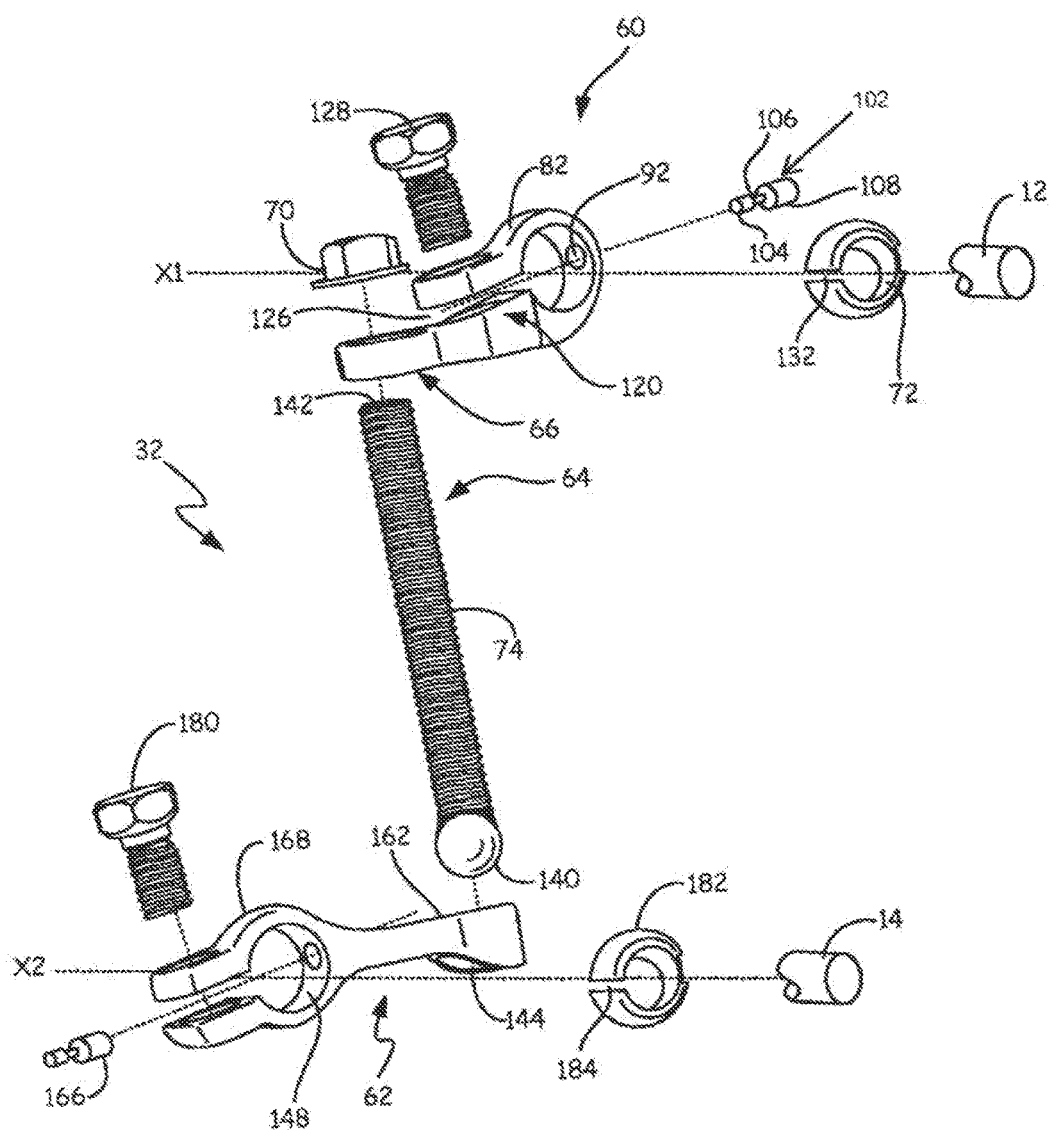
FIG. 34 is an exploded view of the transverse coupler of FIG. 32, according to some embodiments.

FIGS. 32 to 34 show the first transverse coupler 320 (also described as an anchor or connector) of the system 100, according to some embodiments. As shown in FIG. 32, the first transverse coupler 320 is adapted, or otherwise structured, to be positioned laterally across a vertebra, such as the first apical vertebra 42 (FIG. 31) located at or near the apex of the defective curvature along the spine 40. As shown, the first transverse coupler 320 is designed to extend, either partially or fully, from the first side 40A of the spine 40 to the second side 40B of the spine 40.

FIGS. 32 and 33 provide isometric views of the first transverse coupler 320, according to some embodiments. As shown, the first transverse coupler 320 is adapted, or otherwise structured, to receive the first rod 12, such that the first rod 12 is secured laterally relative to a portion of the first transverse coupler 320. In some embodiments, the first rod 12 is substantially prevented from translating in a direction generally perpendicular to the longitudinal axis X1 at a first pivot point P1 while the rod 12 is able to slide axially, or translate axially, along the longitudinal axis X1 through the first pivot point P1 and also to change in pitch and yaw about the first pivot point P1.

In some embodiments, the first transverse coupler 320 is adapted, or otherwise structured, to substantially limit rotation, or roll, of the first rod 12 about the longitudinal axis X1 of the first rod 12. According to some embodiments, the first transverse coupler 320 provides a means for allowing the rod 12 to angulate without substantial lateral translation relative to the portion of the first transverse coupler 320 and without substantial rotation about the longitudinal axis X1.

In some embodiments, the first transverse coupler 320 provides a means for selectively locking the first rod 12 to substantially prevent changes in axial translation, pitch, yaw, and/or roll. The selective locking feature is optionally suitable for constraining movement of the rod 12 under conditions associated with implantation of the system 100 and/or under conditions associated with spinal loading of the system 100 following implantation and securement of the system to the spine 40.

The first transverse coupler 320 is optionally adapted secured to an anchor point on the second side of the spine. In some embodiments, the transverse coupler 320 is secured to an anchor point on the second side 40B of the spine 40 where the anchor point is a spinal anchor directly secured to a vertebral body (not shown). For example, the spinal anchor is optionally a pedicle screw, hook or clamp. In some embodiments, the transverse coupler 320 is secured to an anchor point on the second side 40B of the spine 40 where the anchor point includes a rod coupler configured to be secured to a second rod 14 extending longitudinally along a second side 40B of a spine 40.

In some embodiments, the first transverse coupler 320 is adapted to receive the second rod 14 such that the second rod 14 is secured laterally against lateral translation relative to a portion of the first transverse coupler 320. In some embodiments, the second rod 14 is substantially prevented from translating in a direction substantially perpendicular to the longitudinal axis X2 at a second pivot point P2. In turn, in some embodiments, the second rod 14 is able to slide axially, or translate axially, along a second longitudinal axis X2, relative to the first transverse coupler 320 through a second pivot point P2. The second rod 14 is optionally able to change in pitch and yaw about the second pivot point P2.

The first transverse coupler 320 is optionally adapted, or otherwise structured, to substantially limit rotation, or roll, of the second rod 14 about the second longitudinal axis X2 of the second rod 14. The first transverse coupler 320 provides means for allowing the second rod 14 to angulate without substantial lateral translation relative to the portion of the first transverse coupler 320 and without substantial rotation about the second longitudinal axis X2, according to some embodiments.

In some embodiments, the first transverse coupler 320 provides a means for selectively locking the second rod 14 to substantially prevent changes in axial translation, pitch, yaw, and/or roll. The selective locking feature is optionally suitable for constraining movement of the rod 14 under conditions associated with implantation of the system 100 and/or under conditions associated with spinal loading of the system 100 following implantation and securement of the system to the spine 40.

The first transverse coupler 320 is optionally formed of suitable biocompatible metallic materials, such as titanium, titanium alloy ASTM F136, stainless steel, cobalt chromium alloy ASTM F1537, and/or suitable biocompatible polymeric materials, such as PEEK and/or composite materials.

FIG. 34 is an exploded view of the first transverse coupler 320. As shown, the first transverse coupler 320 includes an adjustment assembly 60 (also described as an adapter or adjustor) adapted to be secured to a first rod 12 extending longitudinally along a first side 40A of the spine 40. According to some embodiments, the adjustment assembly 60 includes a rider 66, an adjustment retainer 70, and a first rod coupler 72 to receive the first rod 12. As shown, the first transverse coupler 320 also includes an adjustment arm 62 adapted to be secured to the second rod 14 and extends from the first side 40A of the spine 40 to a second side 40B of the spine 40, as well as a force directing member 64 having an elongate body 74 adapted to extend between the adjustment assembly 60 and the adjustment arm 62.

Figure 55:
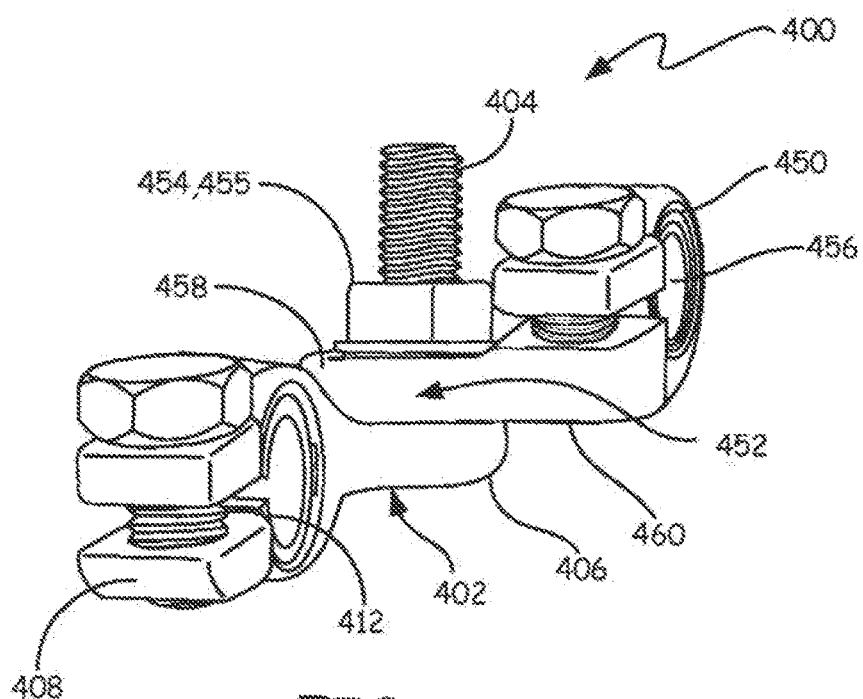
FIG. 55 is an isometric view of an alternative embodiment of a transverse coupler of the system of FIG. 31, according to some embodiments.
Figure 56:
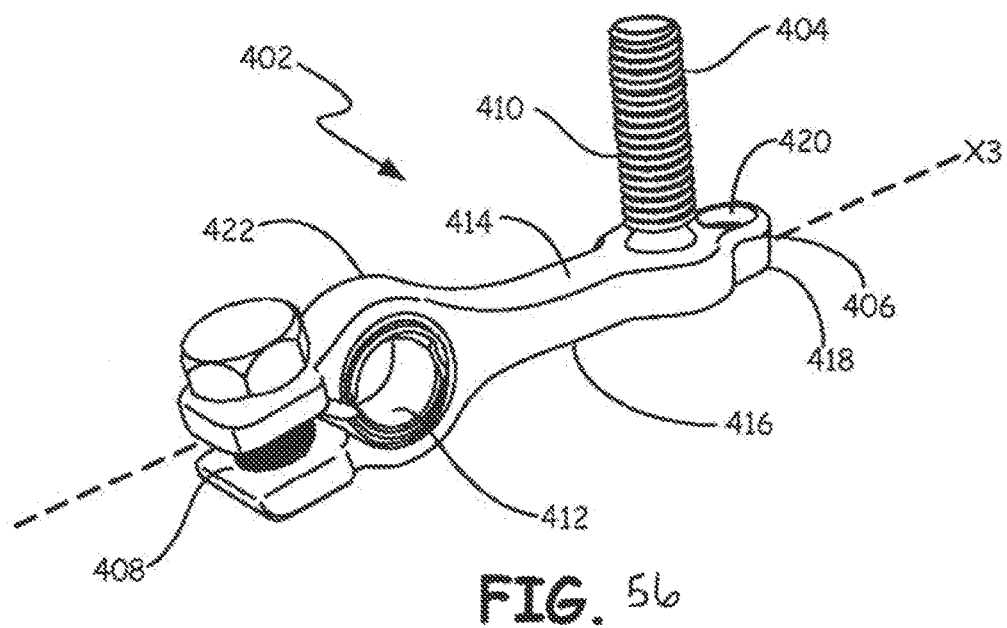
FIG. 56 is a perspective view of the transverse coupler of FIG. 55 with some features not shown to facilitate understanding, according to some embodiments.

As subsequently described, in some embodiments, the first rod coupler 72 is a multi-piece design (e.g. as shown in FIGS. 32-38). In other embodiments, the first rod coupler 72 is a single-piece design adapted, or otherwise structured, for receiving the first rod 12 (FIGS. 55-56).

As shown in FIG. 34, the adjustment assembly 60 connects to the force directing member 64 and the first rod 12, which extends along the first side 40A of the spine 40. As shown in FIG. 31 and FIGS. 43-46, the adjustment assembly 60 and force directing member 64 are optionally adapted to be positioned on the first side 40A of the spine 40. In some embodiments, the adjustment arm 62 is adapted to span across a portion of the first apical vertebra 42 (e.g., lamina-to-lamina or pedicle-to-pedicle on a single vertebra).

FIGS. 35-38 show features of the adjustment assembly 60. As shown, the adjustment assembly 60 has a first rod coupler 72, a rider 66 (also described as a slider or adjuster), and an adjustment retainer 70, also described as a fastener or tightener (see FIGS. 37 and 38).

Figure 35:
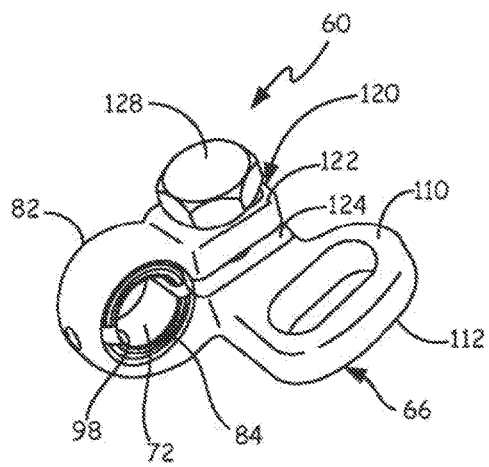
FIG. 35 is a perspective view of a rider of the transverse coupler of FIG. 32, according to some embodiments.
Figure 36:
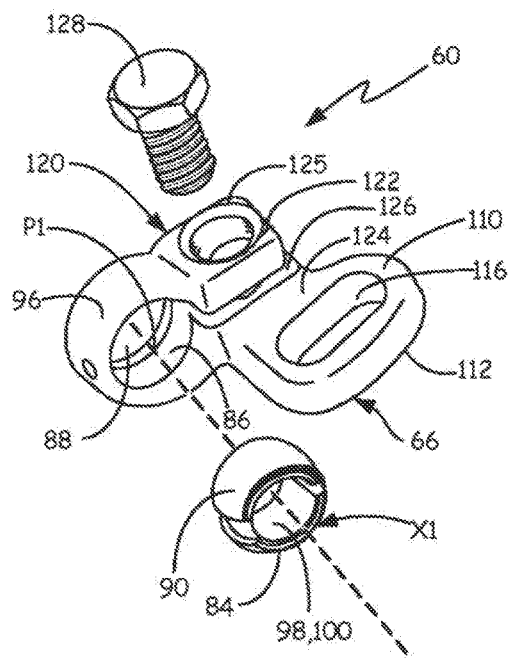
FIG. 36 is an exploded view of the rider of FIG. 35, according to some embodiments.

As shown in FIGS. 34-36, the first rod coupler 72 of the adjustment assembly 60 includes a body 82 and a sleeve insert 84. In some embodiments, the body 82 defines a sleeve aperture 88 extending through a first side 93 of the body 82 to a second side 94 of the body 82. The sleeve aperture 88 is configured for receiving the sleeve insert 84, according to some embodiments. In some embodiments, the sleeve aperture 88 is adapted to mate with the sleeve insert 84, the sleeve insert 84 forming a revolute, substantially concave articulation surface 86. In some embodiments, the sleeve insert 84 forms a revolute, substantially convex articulation surface 90 that complements the sleeve aperture 88. The body 82 has also optionally has a pin chase 92 (e.g. a cylindrical through hole) that extends from the outer surface 96 of the body 82 to the articulation surface 86.

Figure 37:
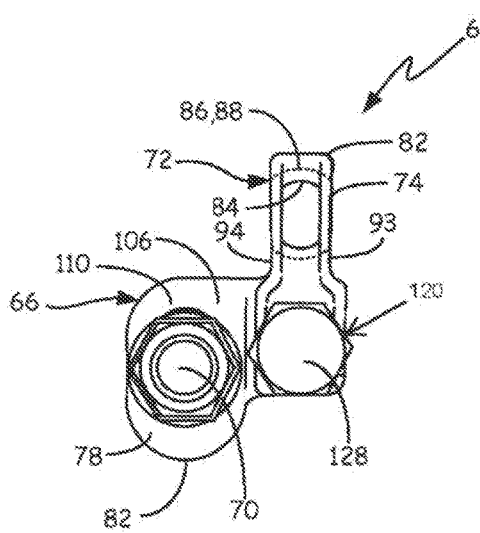
FIG. 37 is a top view of the rider of FIG. 35, according to some embodiments.

FIG. 37 is a top plan view of the adjustment assembly 60 showing some of the internal features of the body 82. As shown, the concave articulation surface 86 of the aperture 88 is adapted, or otherwise structured, to form a substantially complementary fit with the sleeve insert 84. In some embodiments, the sleeve insert 84 is able to be captured by the body 82 within the aperture 88 and have relative angular movement with respect to the body 82.

In some embodiments, the sleeve insert 84 has a passage 98 defining a pivot point P1 through which a portion of the first rod 12 is able to be received. As shown, the pivot point P1 is defined in the passage, where, upon assembly, the first rod 12 passes through the first pivot point P1 such that the longitudinal axis X1 of the rod 12 at the first pivot point P1 is generally concentric with the center of the passage.

As shown, the sleeve insert 84 has a smooth bore 100 for receiving the first rod 12. In some embodiments, the sleeve insert 84 is adapted to help allow the first rod 12 to pass through the passage 98 at the first pivot point P1, where the passage 98 helps allow the rod 12 to angulate about the longitudinal axis X1 at the first pivot point P1 (shown in FIGS. 32, 33, 36, and 38) while rotation and lateral translation of the first rod 12 with respect to the first rod coupler 72 is substantially limited in all planes. In alternative terms, the first rod coupler 72 of the adjustment assembly 60 is configured to be substantially laterally constrained by a first rod 12 when the first rod coupler 72 receives the first rod 12. The first rod coupler 72 selectively locks rotation of the first rod 12 while helping to allow the first rod 12 to axially translate through the first rod coupler 72 and to pivot in pitch and yaw at the first pivot point P1, according to some embodiments.

Figure 38:
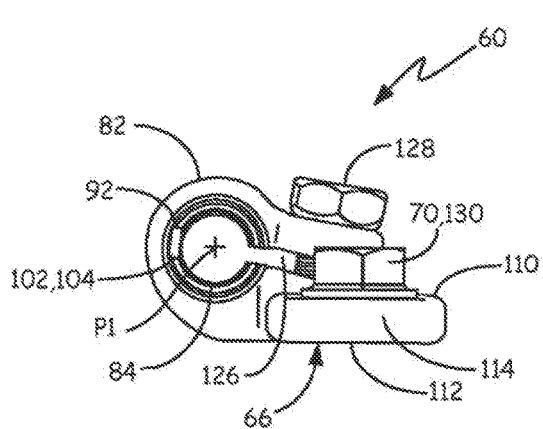
FIG. 38 is a side view of the rider of FIG. 35, according to some embodiments.

As shown in FIGS. 34, 36, and 38, in some embodiments, the body 82 also includes a first protrusion 102 (e.g., a pin) or protrusions (not shown) that extend inwardly into the aperture 88 from the articulation surface 86. The first protrusion 102 is optionally a pin with a head 104, a neck 106, and a body 108, the neck 106 being located between the head 104 and the body 108 (see FIG. 34). The head 104, the neck 106, and the body 108 are optionally substantially cylindrical with the head 104 having a greater diameter than the body 108 and the body 108 having a greater diameter than the neck 106. The first protrusion 102 is optionally received in the pin chase 92 such that the head 104 projects into the aperture 88. In some embodiments the first protrusion 102 and/or body 108 is press fit into the pin chase 92 and/or welded, adhered, or otherwise secured within the pin chase 92. In some embodiments, the first protrusion is temporary and is removable in association with an implantation procedure, providing temporary prevention of roll of the sleeve insert 84 within the body 82 before, during, and/or after securing the system 100 to the spine 40, for example.

As shown, the body of the first rod coupler 72 also includes a locking portion 120. In some embodiments, the locking portion 120 has an upper portion 122 and a lower portion 124 separated by a gap 126 (FIG. 36). In some embodiments, the upper portion 122 has a through slot 125 (FIG. 36) that helps allow a locking member 128 (e.g., a male threaded bolt) to slidably pass through the upper portion 122. The lower portion 124 optionally has a bore (e.g., a female threaded bore), at least partially extending through the lower portion 124. The upper portion 122 and the lower portion 124 can optionally be locked, or clamped, together with the locking member 128 secured across the gap 126. In some embodiments, the locking portion 120 of the first rod coupler 72 is adapted to lock the sleeve insert 84 within the body 82 of the first rod coupler 72.

In some embodiments, the locking portion 120 is adapted to lock the first rod 12 to the first rod coupler 72. As shown in FIG. 34, the sleeve insert 84 has a gap 132 that facilitates locking of the sleeve insert 84 onto the first rod 12. For example, in some implementations, upon sufficiently tightening the locking member 128, the sleeve insert 84 is locked onto rod 12 to arrest axial translation of the rod 12 through the sleeve insert 84. In some implementations, the locking action of the body 82 on the sleeve insert 84 arrests changes in pitch and yaw. In different terms, the rod 12 is able to be selectively locked relative to the first transverse coupler 320 to substantially prevent changes in axial translation, pitch, yaw, and/or roll as desired.

The first rod coupler 72 defines a rod pivot point P1 and is optionally configured to be transitioned from an unlocked state in which a first rod 12 received by the first rod coupler 72 is able to axially translate and change in pitch and yaw about the first rod pivot point P1 to a locked state in which the first rod 12 received by the first rod coupler 72 is locked against axial translation and changes in pitch and yaw about the rod pivot point. When the first rod coupler 72 receives the first rod 12, the first rod coupler 72 is substantially laterally constrained by the first rod, according to some embodiments.

As shown in FIGS. 35-38, the rider 66 (also described as slider or adjuster) includes a first surface 110 and a second surface 112 connected by a lateral wall 114. In some embodiments, the rider 66 is substantially oval-shaped and extends from the lower portion 124 of the locking portion 120. As shown, the first surface 110 of the rider 66 faces generally away from the adjustment arm 62. During operation, the adjustment retainer 70 abuts the first surface 110 of the rider 66 and moves the rider 66 along the force directing member 64, according to some embodiments. Although the adjustment retainer 70 is shown on the rider 66, it should be understood that the adjustment retainer 70 and the rider 66 are not a single unit, but are separate, relatively movable components, according to some embodiments. As shown, the second surface 112 of the rider 66 faces generally toward the adjustment arm 62. During operation, the second surface 112 of the rider 66 engages with the adjustment arm 62 when the adjustment assembly 60 is moved along the force directing member 64 and brought in contact with the adjustment arm 62, according to some embodiments.

As shown in FIG. 36, the rider 66 also includes a slot 116 extending through the rider 66 from the first surface 110 to the second surface 112. As shown, the slot 116, also described as an articulation aperture, has an elongate transverse cross-section. In some embodiments, the slot 116 is configured to receive the elongate body 74 of the force directing member 64 such that the elongate body 74 of the force directing member 64 is adjustable within the slot 116 in the direction in which the slot 116 is elongated. In operation, the rider 66 is optionally movable along the force directing member 64 by, for example, moving the rider along the force directing member. The slot 116 is optionally configured to help allow the force directing member 64 extend through the rider 66 at a substantially orthogonal angle relative to the second surface of the rider 66, as well as a variety of additional angles as desired. For example, the slot 116 is optionally configured to help allow the force directing member 64 to angulate, or pivot, within the slot 116 such that the force directing member extends through a plurality of angles (e.g., orthogonal and non-orthogonal) relative to the second surface 112 of the rider 66. In some embodiments, the slot 116 is configured to allow the force directing member 64, but not the adjustment retainer 70 to extend through the slot 116 of the rider 66. Consequently, the adjustment retainer 70 abuts the first surface 110 of the rider 66 adjacent the slot 116 and does not extend through the slot 116 of the rider 66, according to some embodiments.

As shown in FIGS. 37 and 38, the adjustment retainer 70 is configured to couple to the force directing member 64. The adjustment retainer 70 is configured to travel along the force directing member 64 in a direction of a central axis defined by the elongate body 74 of the force directing member 64 as desired. In some embodiments, the adjustment retainer 70 is a threaded cap 130 (e.g., a female threaded nut) configured to mate with and be screwed down the length of the force directing member 64, pressing against the rider 66, and thereby helping to move the rider 66 along the force directing member 64 as the adjustment retainer 70 is actuated along the force directing member 64.

FIGS. 32-34 show features of the force directing member 64 (also described as a connector), according to some embodiments. In some embodiments, the force directing member 64 includes the elongate body 74 and extends from a first end 140 and a second end 142. In other embodiments, the elongate body includes a head portion with a pocket configured to receive a rod, for example, a rod-shaped portion of the rider and/or adjustment arm (not shown). In some embodiments, the force directing member 64 includes a threaded, elongate body 74 adapted to mate with the threaded cap 130 of the adjustment retainer 70. Alternatively, in some embodiments, the elongate body 74 has teeth, barbs or stepped features along the elongate body 74 adapted to mate with teeth, barbs, or complementary features of the adjustment retainer 70. Some examples of the force directing member 64 optionally include, but are not limited to, a threaded screw, a standard bolt, a toggle bolt, a female threaded partial tube, a cable tie, a zip tie, a peg fastener or other type of selectively adjustable mechanism.

The first end 140 of the force directing member 64 is optionally adapted to be received within an aperture 144, also described as an articulation aperture or a socket, of the adjustment arm 62. In some embodiments, the first end 140 of the force directing member 64 is adapted to allow the force directing member 64 to change in pitch, yaw and roll from within the aperture 144. As shown in FIG. 32, the first end 140 is generally spherically shaped and is adapted to fit within the aperture 144. In some embodiments, the first end 140 of the force directing member 64 is adapted to substantially limit the force directing member 64 from substantially changing in pitch, yaw and roll from within the aperture 144. The first end 140 of the force directing member 64 is optionally a generally polygon-shaped end. For example, a force directing member 64 with a square-end, when fit into a complementary polygon-shaped aperture of the adjustment arm 62, is substantially prevented from changing in pitch, yaw, and roll from within the aperture. Alternatively, a force directing member can optionally include a cylinder-end, e.g. a T-shaped first end, which when fit into a complementary shaped aperture of the adjustment arm 62, is substantially prevented from changing in pitch, but allows changes in yaw and roll from within the aperture.

The force directing member 64 is adapted to be secured to the adjustment assembly 60 and the adjustment arm 62 such that the elongate body 74 of the force directing member 64 extends between the rider 66 of the adjustment assembly 60 and the adjustment arm 62, according to some embodiments. The first force directing member 64 has the elongate body 74 optionally defining an effective length L (FIGS. 43 and 44) between the rider 66 of the adjustment assembly 60 and the adjustment arm 62. Alternatively, the elongate body 74 may optionally define the effective length L as the distance between a second surface 112 of the rider 66 and the first end 140 of the force directing member 64 (not shown). The effective length L is dependent on the position of the adjustment retainer 70 along the force directing member 64, according to some embodiments. An effective angle α (FIGS. 47 and 49) between the force directing member 64 and a first surface 160 (shown in FIG. 39) of the adjustment arm 62 is optionally dependent on the position of the first and second rods 12, 14. As the adjustment retainer 70 is engaged, or rotated clockwise (for right hand threaded components), along the force directing member 64, the effective length L is shortened and the angle α is increased as desired (for example, see α1 in FIG. 47). If the adjustment retainer 70 is disengaged, or rotated counter-clockwise (for right hand threaded components), the effective length L is lengthened and the angle α is decreased as desired (for example, see α2 in FIG. 49). Although a screw, or threaded, adjustment mechanism is shown, a variety of alternative adjustment mechanisms (e.g., a pawl and ratchet system) are contemplated.

FIGS. 39-42 show features of the adjustment arm 62 (also described as a transverse connector or arm), according to some embodiments. The adjustment arm 62 is optionally configured to extend from a first side 40A of the spine 40 to a second side 40B of the spine 40. As shown, the adjustment arm 62 includes a second rod coupler 150, a connecting portion 152, and a base portion 154, the adjustment arm having a first end 156, a second end 158, the first surface 160, a second surface 162, and a longitudinal axis X3 extending from the first end 156 to the second end 158.

As shown, the connecting portion 152 of the adjustment arm 62 has an elongate body 164 that extends from the base portion 154 to the second rod coupler 150. In some embodiments, the first surface 160 of the adjustment arm 62 faces generally toward the adjustment assembly 60 and the second surface 162 of the adjustment arm 62 faces generally away the adjustment assembly 60. In operation, the first surface 160 of the adjustment arm 62 also engages with the adjustment assembly 60 when the adjustment assembly 60 is moved along the force directing member 64 and brought in contact with the adjustment arm 62, according to some embodiments.

Figure 39:
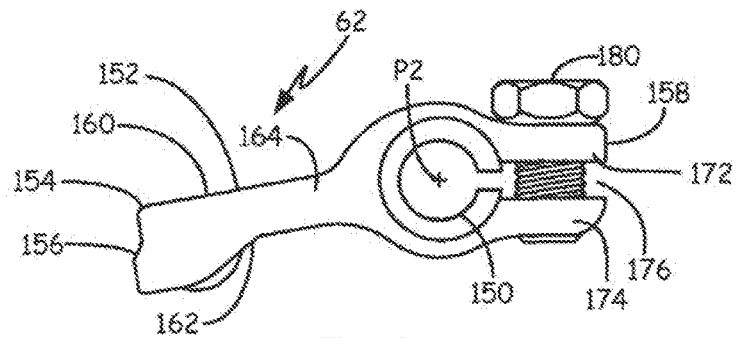
FIG. 39 is a side view of an adjustment arm of the transverse coupler of FIG. 32, according to some embodiments.

FIG. 39 is a side view of the adjustment arm 62, according to some embodiments. As shown, the second end 158 of the adjustment arm 62 includes the second rod coupler 150, which is configured to be secured to a second rod 14 extending longitudinally along a second side 40B of a spine 40. In some embodiments, the second rod coupler 150 of the adjustment arm 62 is substantially similar to the first rod coupler 72 of the adjustment assembly 60, with the exception that the second rod coupler 150 receives the second rod 14. The second rod coupler 150 of the adjustment arm 62 is optionally configured to substantially limit roll of the second rod 14 where the second rod 14 is received by the second rod coupler 150. As shown in FIG. 39, the second rod coupler 150 is adapted to be substantially laterally constrained by the second rod 14 with the second rod 14 being able to axially translate through the second rod coupler 150 and to pivot in pitch and yaw at the second rod coupler 150 at a second pivot point P2.

As shown in FIG. 34, a body 168 of the second rod coupler 150 also includes a second protrusion 166 (e.g., a pin) or protrusions (not shown) that extends inwardly into the aperture from the articulation surface 148. In some embodiments, the second protrusion 166 is substantially similar to the first protrusion 102 of the first rod coupler 72, discussed previously herein, and substantially prevents a sleeve insert 182 from rolling within the body 168 of the second rod coupler 150.

As shown in FIG. 39, the second rod coupler 150 of the adjustment arm 62 includes a locking mechanism similar to the first rod coupler 72. In some embodiments, the locking portion 170 has a first portion 172 and a second portion 174 separated by a gap 176. The first portion 172 and the second portion 174 can be locked, or clamped, together with the locking member 180 is secured into a through slot 178 and across the gap 176, according to some embodiments. As shown, the sleeve insert 182 also has a gap 184 (FIG. 34) that facilitates locking of the sleeve insert 182 onto the second rod 14. For example, upon sufficiently tightening the locking member 180, the sleeve insert 182 is optionally locked onto rod 14 to substantially arrest axial translation of the second rod 14 through the sleeve insert 182. In some embodiments, the locking action of the body 168 of the second rod coupler 150 on the sleeve insert 182 substantially arrests changes in pitch and yaw. In different terms, the second rod 14 is able to be selectively locked relative to the first transverse coupler 320, in accordance with some embodiments. The selective locking feature is optionally suitable for constraining movement of the rod 14 under conditions associated with implantation of the system 100 and/or under conditions associated with spinal loading of the system 100 following implantation and securement of the system to the spine 40.

Figure 40:
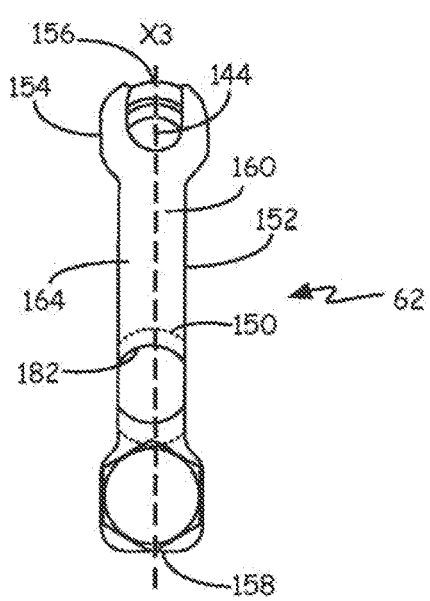
FIG. 40 is a top view of the adjustment arm of FIG. 39, according to some embodiments.
Figure 41:
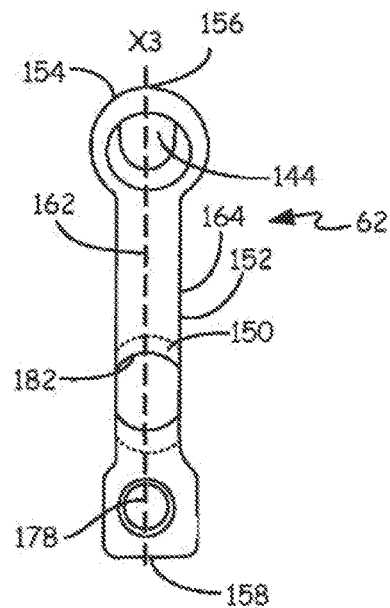
FIG. 41 is a bottom view of the adjustment arm of FIG. 39, according to some embodiments.
Figure 42:
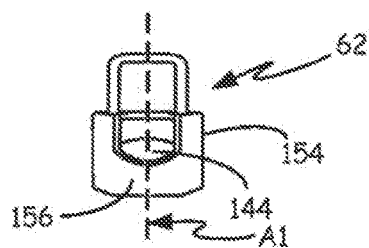
FIG. 42 is a rear view of the adjustment arm of FIG. 39, according to some embodiments.

As mentioned previously and as shown in FIGS. 40 and 41, the first end 156 of the adjustment arm 62 includes an articulation aperture 144 extending from the first surface 160 to the second surface 162. In some embodiments, the articulation aperture 144 is adapted to receive the force directing member. The articulate aperture 144 has a revolute, substantially concave inner surface with an elongate opening extending in the direction of the longitudinal axis X3 (FIGS. 40-42).

As shown in FIGS. 43-46, the elongate body 74 of the force directing member 64 extends from the first surface 160 of the adjustment arm 62 at an angle relative to the longitudinal axis X3. In some embodiments, the force directing member 64 extends from first surface 160 of the adjustment arm 62 at an adjustable angle relative to the longitudinal axis X3. The angle may be, for example, optionally adjusted to any angle between 0 to 90 degrees. In some embodiments, the force directing member 64 is rigidly secured to the first end 156 of the adjustment arm 62 and extends from the first surface 160 of the adjustment arm 62 at a substantially fixed angle relative to the longitudinal axis. In some embodiments, the elongate body 74 of the force directing member 64 extends from the first surface 160 of the adjustment arm 62 at a substantially orthogonal angle relative to the longitudinal axis X3.

In some embodiments, the spherically shaped first end 140 of the force directing member 64 fits within an articulation aperture 144. The first end 140 of the force directing member 64 is optionally received within the articulation aperture 144 (FIGS. 40 and 41) of the adjustment arm 62 such that the force directing member 64 is able to angulate. In some embodiments, the force directing member 64 is substantially free to angulate in a first plane of angulation A1 (FIGS. 43 and 45) to a greater degree than in other planes of angulation (e.g., a second plane of angulation A2 as shown in FIGS. 44 and 46). The first plane of angulation A1 is depicted as a line (FIGS. 44 and 46). The first plane A1 is defined by the longitudinal axis X3 and the normal axis X4 of the transverse coupler, both falling within the first plane A1. The first plane A1 is generally orthogonal to the second plane A2 while being generally parallel to the longitudinal axis X3 and the normal axis X4. The second plane of angulation A2 is depicted as a line (FIGS. 43 and 45), where the first plane A1 extends orthogonally from the second plane A2. The normal axis X4 falls within the second plane A2, the normal axis X4 being generally parallel the second plane A2. In some embodiments, the force directing member 64 is substantially free to angulate in a single plane of angulation (e.g., the first plane A1) or multiple planes of angulation (e.g., the first plane A1 and the second plane A2) as desired.

In some embodiments, the force directing member 64 is received within the articulation aperture of the adjustment arm 62 such that the force directing member 64 is able to angulate. The force directing member 64 is able to optionally articulate in a first plane of angulation A1 to a greater extent than the force directing member 64 is able to angulate in a second plane of angulation A2 that is substantially perpendicular to the first plane of angulation. In some embodiments, the force directing member 64 has an angulation range of 90 degree, wherein the force directing member 64 is able to articulate through an angle of about 45 degrees or more in the first plane of angulation A1. The force directing member 64 optionally articulates in the first plane of angulation A1 and is substantially prevented from articulating in the second plane of angulation A2. It is also contemplated that the force directing member 64 is able to articulate in a multiple planes of angulation, according to some embodiments.

FIGS. 47-49 show a view of the system 100 taken in a transverse plane to the spine 40 near the apex of the defective curvature, with some inferior and superior portions of the spine 40 and system 100 not shown to simplify illustration. As shown, the transverse coupler 320 is secured to the first apical vertebra 42 and to the first and the second rods 12, 14. In sequentially viewing the Figures, it can be seen that during operation, the vertebrae 42 is laterally translated and derotated while the transverse coupler 320 is being adjusted, according to some methods of using the system 10. After the adjustment, the first apical vertebra 42 is then locked against further rotation or lateral movement by locking the transverse coupler 320 to both the first and the second rods 12, 14, according to some embodiments. FIGS. 47 and 48 show the vertebra 42 in an uncorrected state, or a partially derotated and laterally offset state with the first and the second rods 12, 14 secured in first and the second rod couplers 72, 150 of the first transverse coupler 320.

In order to secure the first rod 12 onto the spine 40, the first and second stabilizing anchors 16, 18 are optionally secured at an inferior spinal position, or level, (e.g., to an inferior vertebrae) and a superior spinal position, or level (e.g., to a superior vertebrae), respectively. In some embodiments, the first rod 12 is substantially laterally constrained by the first and second stabilizing anchors 16, 18 such that the first rod 12 extends longitudinally on the first side 40A of the spine 40 and is laterally constrained relative to the inferior and superior vertebrae.

The second rod 14 is optionally secured on an opposite side of the spine at intermediate positions along the spine by a first intermediate anchor and a second intermediate anchor, for example. The first and second intermediate anchors are adapted to substantially constrain the second rod 14 against substantial lateral translation as desired. The first intermediate anchor (e.g., the fifth stabilizing anchor 23 as shown in FIG. 31) is optionally secured to a first, intermediate vertebrae and a second, intermediate vertebrae, each located between the superior and inferior vertebrae to which the first and second stabilizing anchors are secured. In some embodiments, the first and second intermediate anchors are secured to vertebral bodies located on or adjacent vertebral bodies that form an apex, or apical region of the deformity. As shown in FIG. 31, with the spine 40 in a generally corrected state, the first intermediate anchor is positioned at a lower vertebral position, or level than the adjustment assembly 60 and at a higher vertebral position, or level than the first stabilizing anchor 16. In turn, the second intermediate anchor (e.g., the sixth stabilizing anchor 25), is optionally positioned along the spine 40 at a higher vertebral position, or level along the second rod 14 between the adjustment assembly 60 and the second stabilizing anchor 18.

In order to assemble the transverse coupler 320 onto the system 100 (FIG. 31), a physician can optionally articulate components of the transverse coupler 320 (e.g. the force directing member 64 and the adjustment assembly 60), such that the rod couplers 72, 150 of the transverse coupler 320 are able to reach the first and the second rods 12, 14. Alternatively or additionally, a physician or other user can optionally employ a variety of tools and associated methods. For example, the user can optionally use a surgical tool, such as a wrench, clamp, or gripping tool, compressor, distractor adapted to couple to the first rod 12, the second rod 14, the first transverse coupler 320, and/or other spinal devices. The tool is used to assist the physician in derotating and/or translating the spinal column 40 during a correction as desired. The tool is optionally used to assist the physician in maintaining a desired configuration while assembling the system 100 onto the spine 40.

As shown in FIG. 47, the first transverse coupler 320 is assembled onto the first apical vertebra 42. During assembly, the first and the second rod couplers 72, 150 of the first transverse coupler 320 are optionally adjusted to an unlocked state when coupled to the first and the second rods 12, 14 respectively, such that the physician has free movement as desired, when assembling the transverse coupler 320 onto the spine 40. In some embodiments, the first and the second rod couplers 72, 150 are adjusted to an unlocked state to reduce binding of the rods 12, 14 and to provide more degrees of freedom to the first transverse coupler 320 during the lateral translation and derotation of the spine.

During or after assembly, the transverse coupler 320 is optionally adjusted to a locked state onto the rods 12, 14 of the system 100 to allow for lateral translation and derotation of the first apical vertebra 42. In some embodiments, the first and the second rods 12, 14 are generally locked against rotation roll within the corresponding couplers 72, 150 of the first transverse coupler 320, as previously discussed herein. The first rod 12 is optionally left unlocked within the first rod coupler 72 while the second rod 14 is locked against axial translation and changes in pitch and yaw within the second rod coupler 150. In some embodiments, the first rod 12 is able to change in pitch and yaw, while the second rod 14 is substantially constrained against changes in pitch, yaw, and roll during at least a portion of the correction.

In some embodiments, the first rod 12 is able to axially translate and change in pitch and yaw about the first pivot point P1 while the vertebra 42 is being laterally translated and derotated during the full duration of the correction. In other embodiments, the first rod 12 is locked against changes in pitch and yaw during a portion of the correction and/or after the correction. FIGS. 47-49 depict a use of the transverse coupler 320 such that the first rod 12 is able to change in pitch, yaw, and axial translation during a correction and is locked against changes in pitch, yaw, and axial translation after the correction, according to some embodiments.

FIG. 48 shows the first apical vertebra 42 in a partially derotated and a laterally offset state and FIG. 49 shows the first apical vertebra 42 in a maximally derotated and laterally translated state, according to some embodiments. The first transverse coupler 320 operates to laterally translate and rotate the second rod 14 towards the first rod 12 such that a portion of the spine 40 is moved into a more correct configuration, in accordance with some embodiments. For example, comparing FIG. 49 to FIG. 47, it can be seen that the distance between the first rod 12 and the second 14 has significantly shortened (identified as D1 and D2 in FIGS. 47 and 49, respectively) after the correction. Shown by an arrow in the Figures, the first transverse coupler 320 is optionally adapted to derotate the vertebra 42 and laterally translate the vertebra 42, either contemporaneously, sequentially, or combinations thereof.

FIG. 49 shows the first apical vertebra 42 maximally derotated and laterally translated. The transverse coupler 320 is optionally locked after the vertebra 42 has been laterally translated and derotated as desired (e.g., as shown in FIG. 49), to prevent relative translational and rotational movement between the first rod 12 and second rod 14 to stabilize and hold the vertebra 42 in the corrected position. Additional anchors 23, 25, 28, 30 are added to the spine 40 as desired to provide additional stability to the spine 40. In some embodiments, after the vertebra 42 has been laterally translated and/or partially derotated and the transverse coupler 320 has been locked to the rods, the adjustment retainer 70 is actuated along the force directing member 64 to derotate, or further derotate, the spine 40.

An illustrative but non-limiting example of correcting a spinal defect includes securing the first stabilizing anchor 16 at an inferior spinal position and the second stabilizing anchor 18 at a superior spinal position along the first side 40A of the spine 40. The first rod 12 is extended longitudinally on the first side 40A of the spine 40 and is substantially laterally constrained between the first and the second stabilizing anchors 16, 18, according to some embodiments.

The first anchor 24 is optionally secured at an inferior spinal position and the second anchor 26 is secured at the superior spinal position along the second side 40B of the spine 40. The second rod 14 extends longitudinally on the second side 40B of the spine 40 and is substantially laterally constrained between the first and the second anchors 24, 26, according to some embodiments.

The first transverse coupler 320 is optionally assembled onto the first and the second sides 40A, 40B of the spinal column 40, either at some time prior to, during, or after securing the stabilizing anchors 16, 18, 24, 26 to the spine 40. In some embodiments, the transverse coupler 320 is assembled onto the first side 40A of the spine 40 by coupling the first rod coupler 72 of the adjustment assembly 60 to the first rod 12. The first rod 12 is able to axially translate and change in pitch and yaw, but is substantially restricted from lateral translation at the first rod coupler 72, according to some embodiments.

The transverse coupler 320 is optionally assembled onto the second side 40B of the spine 40 by coupling the second rod coupler 150 of the adjustment arm 62 to the second rod 14. In some embodiments, the second rod 14 is locked from axial translation and changing in pitch, yaw and roll at the second rod coupler 150. The adjustment arm 62 of the first transverse coupler 320 is positioned across the first apical vertebra 42 such that a connecting portion 152 of an adjustment arm 62 extends from the first side 40A of the spine 40 to the second side 40B of the spine 40, according to some embodiments.

As previously discussed, the first transverse coupler 320 includes the force directing member 64 that is optionally the threaded toggle bolt. The force directing member 64 is optionally secured to the adjustment assembly 60 and the adjustment arm 62 with an initial effective length.

In some embodiments, an adjustment retainer 70 is actuated along the force directing member 64 by rotating the threaded cap 130 of the adjustment retainer 70 clockwise along a threaded portion of the force directing member 64. Actuating the retainer 70 decreases the effective length L as desired. In some embodiments, the effective length L becomes approximately zero when the adjustment arm 62 becomes seated flush against the adjustment assembly 60. The force directing member 64 is optionally cut or broken off to a shorter length, as desired, during the procedure as the effective length L decreases from the initial effective length.

As the adjustment retainer 70 is optionally actuated along the force directing member 64, the rider 66 provides a resistance force that transmits through the force directing member 64 to the adjustment arm 62. In some embodiments, the resistance force causes the second rod 14 to move towards the first rod 12, which laterally translates a portion of the spine 40 towards the first rod 12.

In some embodiments, the adjustment retainer 70 is actuated along the first force directing member 64 such that the first surface 160 of the adjustment arm 62 comes into contact with the adjustment assembly 60. The adjustment retainer 70 is then optionally further actuated to pivot the rider 66 and the adjustment arm 62 towards each other such that the first surface 160 of the adjustment arm 62 becomes seated flush against the second surface 112 of the rider 66. In some embodiments, the adjustment assembly 60 receives the force directing member 64 within an articulation aperture 144 having an elongate transverse cross-section, allowing the force directing member 64 to articulate in the first plane of angulation as the adjustment retainer 70 is driven along the first force directing member 64. As the adjustment assembly 60 and the adjustment arm 62 impinge and ultimately become seated together, the force directing member 64 articulates into a generally orthogonal angle relative to the longitudinal axis X3 defined by the adjustment arm 62, according to some embodiments. In some embodiments, as the force directing member 64 articulates, the first apical vertebra 42 derotates. Once the adjustment arm 62 and the adjustment assembly 60 are brought into the desired amount of contact or the desired effective length L of the force directing member 64 has been achieved.

Figure 50:
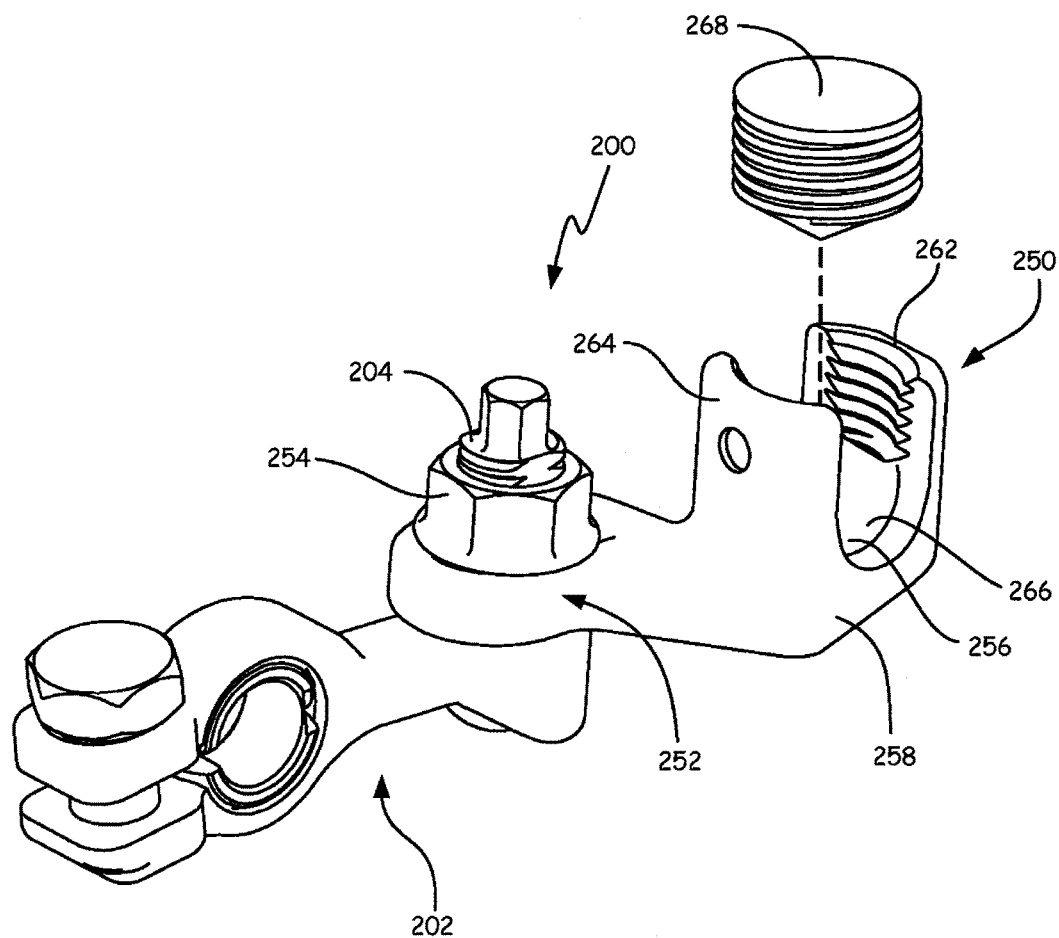
FIG. 50 is an isometric view of an alternative embodiment of a transverse coupler of the system of FIG. 31, according to some embodiments.

FIG. 50 shows an isometric view of an alternative embodiment of a first transverse coupler 200 of the system 100, also described as a transverse connector. The first transverse coupler 200 is optionally adapted, or otherwise structured, to be positioned laterally across one or more of the vertebrae, such as the first apical vertebra 42 (FIG. 31) located at or near an apical position along the spine 40. As shown, the first transverse coupler 200 is adapted to extend from the first side 40A of the spine 40 toward, and ultimately across to the second side 40B of the spine 40.

As shown, the first transverse coupler 200 includes features that are substantially similar to the first transverse coupler 320. In some embodiments, the adjustment arm 202 is substantially similar to the adjustment arm 62 of the first transverse coupler 320, and thus various features of the adjustment arm 62 of the first transverse coupler 320 also apply to the adjustment arm 202 of the first transverse coupler 200.

As shown in FIG. 50, the first transverse coupler 200 includes an adjustment assembly 250 adapted to be secured to a first rod 12. In some embodiments, the adjustment assembly 250 includes a rider 252, an adjustment retainer 254, and a first rod coupler 256 to receive the first rod 12.

Figure 51:
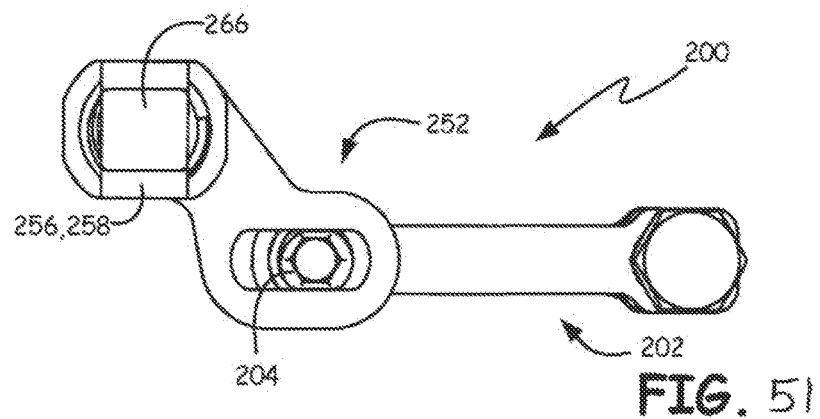
FIGS. 51-53 show top, side, and a rear views, respectively, of the transverse coupler of FIG. 50, according to some embodiments.
Figure 52:
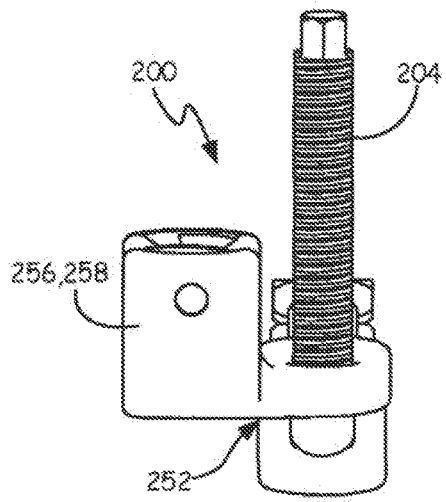
Figure 53:
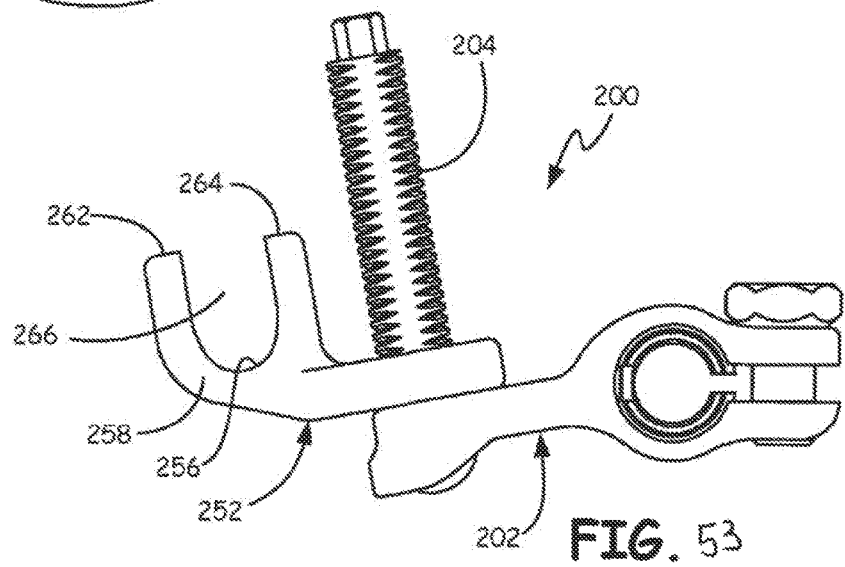

FIGS. 51-53 show a top, a side and a rear view of the first transverse coupler 200. In some embodiments, the rider 252 and the adjustment retainer 254 of the first transverse coupler 200 engage with an adjustment arm 202 and/or a force directing member 204 in a manner substantially similar to the rider 66 and adjustment retainer 70 of the first transverse coupler 320. The various features of the rider 66 and the adjustment retainer 70 of the first transverse coupler 320 also apply to the rider 252 and the adjustment retainer 254 of the first transverse coupler 200. The main difference between the first transverse coupler 200 and the first transverse coupler 320 is the first rod coupler 256, according to some embodiments.

As shown in FIGS. 50 and 53, the first rod coupler 256 includes a head portion 258 is substantially U-shaped (similar to the U-shaped head 142 of the first anchor 20 discussed above with respect to FIG. 1) having a first prong 262 and a second prong 264 defining a pocket 266 for receiving the first rod 12. The head portion 258 of the adjustment assembly 250 serves to couple the first transverse coupler 200 to the first rod 12. As shown, the prongs 262, 264 are threaded for receiving a clamping screw 268 adapted to engage and secure the first rod 12 immobilized within the pocket 266. The first rod coupler 256 of the adjustment assembly 250 is optionally configured to receive the first rod 12 such that the first rod 12 is free to change in at least roll within the first rod coupler 256. In some embodiments, first rod coupler 256 is configured to receive the first rod 12 such that the first rod 12 is free to change in pitch and roll, but is substantially limited from changes in yaw within the first rod coupler 256. In some embodiments, the first rod coupler 256 is configured to be transitioned from an unlocked state in which the first rod 12 is free to move in at least one of slide, pitch, yaw or roll with respect to the first rod coupler 256 to a locked state. In some embodiments, the first rod 12 is received by the first rod coupler 256 such that the first rod coupler 256 becomes substantially laterally constrained by the first rod 12. The first rod coupler 256 optionally locks the first rod 12 against axial translation, changes in pitch, yaw and roll about a rod pivot point with respect to the first rod coupler 256.

Figure 54:
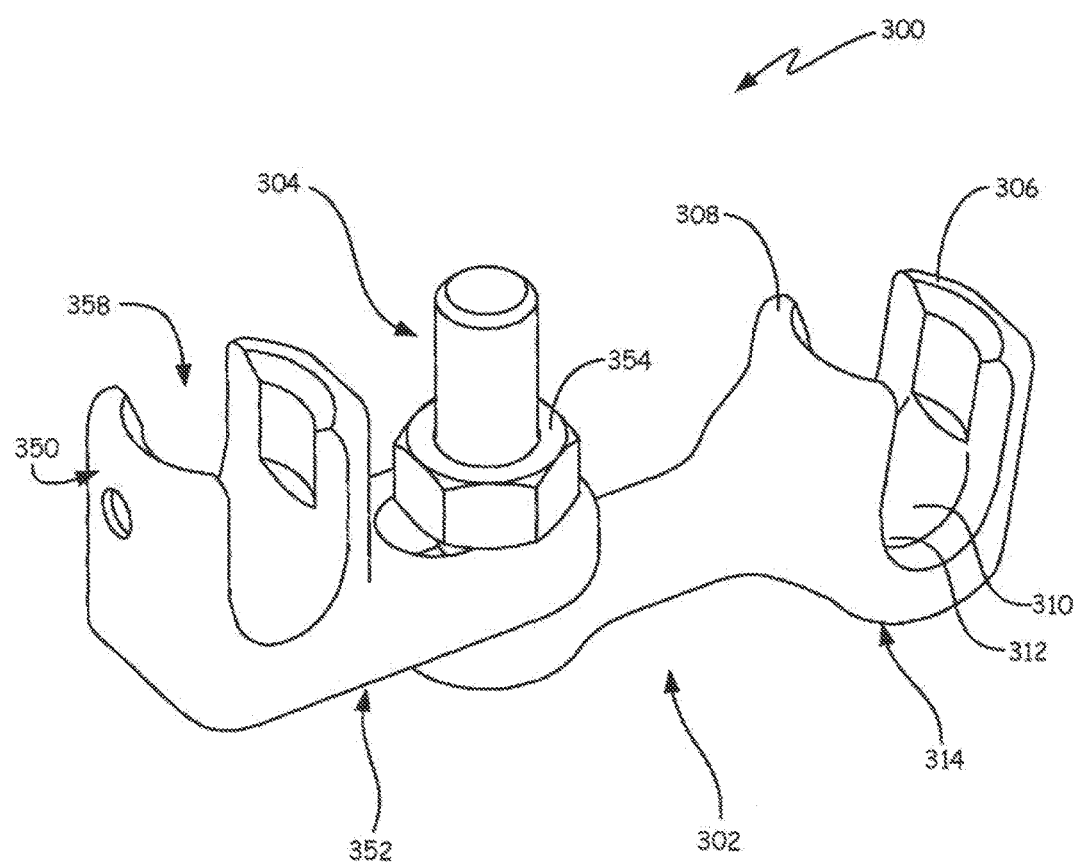
FIG. 54 is an isometric view of an alternative embodiment of a transverse coupler of the system of FIG. 31, according to some embodiments.

FIG. 54 provides another alternative embodiment of the first transverse coupler 300, which includes an adjustment assembly 350 adapted to be secured to a first rod 12. In some embodiments, the adjustment assembly 350 includes a rider 352, an adjustment retainer 354, and a first rod coupler 358 to receive the first rod 12. The first rod coupler 358 optionally receives the first rod 12 in a substantially similar manner to the adjustment assembly 250 of the first transverse coupler 200, and therefore various features of the adjustment assembly 250 of the first transverse coupler 200 also apply to the adjustment assembly 350 of the first transverse coupler 300. The primary difference between the first transverse coupler 300 and the first transverse coupler 200 is the design of the second rod coupler 312 of the adjustment arm 302, according to some embodiments.

As shown in FIG. 54, the adjustment arm 302 is substantially similar to the adjustment arm 62 of the first transverse coupler 320 with a difference of having a second rod coupler 312 that includes a U-shaped head portion 314. The head portion 314 is substantially U-shaped and includes a first prong 306 and a second prong 308 that defines a pocket 310 for receiving the second rod 14. The head portion 314 of the adjustment arm 302 serves to couple the first transverse coupler 300 to the second rod 14. As shown, the prongs 306, 308 are optionally threaded for receiving a clamping screw (not shown) adapted to engage and secure the second rod 14 immobilized within the pocket 310. The second rod coupler 312 receives the second rod 14 similar to how the first coupler 356 receives the second rod 14, and therefore those various features of the first rod coupler 256 are also applicable to the second rod coupler 312 with respect to the second rod 14.

FIG. 55 shows an isometric view of another first transverse coupler 400 of the system 10, also described as a fixed transverse coupler. The first transverse coupler 400 is optionally adapted, or otherwise structured, to be positioned laterally across one or more of the vertebrae, such as the first apical vertebra 42 (FIG. 31) located at or near an apical position along the spine 40. As shown, the first transverse coupler 200 is adapted to extend from the first side 40A of the spine 40 toward, and ultimately across to the second side 40B of the spine 40.

As shown, the first transverse coupler 400 includes features that are substantially similar to the first transverse coupler 320. In some embodiments, the first transverse coupler 400 includes an adjustment assembly 450 adapted to be secured to a first rod 12. In some embodiments, the adjustment assembly 450 includes a rider 452, an adjustment retainer 454, and a first rod coupler 456 to receive the first rod 12. In some embodiments, the adjustment assembly 450 is substantially similar to the adjustment assembly 60 of the first transverse coupler 320.

The first transverse coupler 400 optionally includes an adjustment arm 402 with a second rod coupler 412 adapted to be secured to the second rod 14 and extends from the first side 40A of the spine 40 to the second side 40B of the spine 40. In some embodiments, the adjustment arm 402 has a first end 406 and a second end 408 and a longitudinal axis X3 extending between the first and the second ends 406, 408. The adjustment arm 402 optionally has a first surface 414 and a second opposite surface 416 (FIG. 56).

FIG. 56 shows a view of the adjustment arm 402, with some features not shown to facilitate understanding, which is substantially similar to the adjustment arm 62 of the first transverse coupler 320 with a difference of having a force directing member 404 rigidly secured to the first end 406 of the adjustment arm 402. In some embodiments, the force directing member 404 extends from the first surface 414 of the adjustment arm 402 at a generally orthogonal angle relative to the longitudinal axis X3. In other embodiments, the force directing member 404 extends from the first surface 414 of the adjustment arm 402 at a non-orthogonal angle relative to the longitudinal axis X3. The force directing member 404 has an elongate body 410 extending between the adjustment assembly 450 and the adjustment arm 402, according to some embodiments.

The adjustment arm 402 optionally includes an elongated portion 418 with an aperture 420 at the first end 406 of the adjustment arm 402. The aperture 420 is optionally adapted to receive at least a portion of a surgical tool that may be used during the implant procedure to obtain and hold a spinal correction.

FIGS. 57-59 show a view of the system 100 taken in a transverse plane to the spine 40 near the apex of the defective curvature, with some inferior and superior portions of the spine 40 and system 100 not shown to simplify illustration. As shown, the transverse coupler 400 is secured to the first apical vertebra 42 and to the first and the second rods 12, 14. In sequentially viewing the Figures, it can be seen that during operation, the first apical vertebra 42 is laterally translated and derotated while the transverse coupler 400 is being adjusted, according to some methods of using the system 10. FIGS. 57 and 58 show the first apical vertebra 42 in a partially derotated and a laterally offset state and FIG. 59 shows the first apical vertebra 42 maximally derotated and laterally translated.

In order to assemble the transverse coupler 400 onto the system 100 (FIG. 31), a physician can optionally angulate the adjustment assembly 450 of the transverse coupler 200 (e.g.) such that the rod couplers 456, 412 of the transverse coupler 400 are able to reach the first and the second rods 12, 14. Alternatively or additionally, a physician or other user can optionally employ a variety of tools and associated methods. For example, the user can use a surgical tool, such as a wrench, clamp, or gripping tool, adapted to couple to the first rod 12, the second rod 14, the first transverse coupler 400, and/or other spinal devices as desired. In some embodiments, the surgical tool optionally assists the physician in derotating and/or translating a spinal column 40 during a correction. The surgical tool optionally assists the physician in maintaining a desired configuration while assembling the system 100 onto the spine 40.

A spinal correction using the first transverse coupler 200 as shown in FIGS. 57-59 optionally proceeds similarly to the spinal correction using the transverse coupler 320 as shown in FIGS. 43-46.

An illustrative but non-limiting example of correcting a spinal defect using the first transverse coupler 400 is provided herein. Stabilizing anchors 16, 18, anchors 24, 26, and rods 12, 14 are optionally secured to the spine 40 using the operation as discussed previously.

The first transverse coupler 200 is assembled onto the first and the second sides 40A, 40B of the spinal column 40, either at some time prior to, during, or after securing the stabilizing anchors 16, 18, 24, 26 to the spine 40. In some embodiments, the transverse coupler 400 is assembled onto the first side 40A of the spine 40 by coupling the first rod coupler 456 of the adjustment assembly 250 to the first rod 12. The first rod 12 is able to axially translate and change in pitch and yaw, but is substantially restricted from translating laterally at the first rod coupler 456, according to some embodiments.

The transverse coupler 400 is optionally assembled onto the second side 40B of the spine 40 by coupling the second rod coupler 412 of the adjustment arm 402 to the second rod 14. In some embodiments, the second rod 14 is locked from axial translation and changing in pitch, yaw and roll at the second rod coupler 412. The adjustment arm 402 of the first transverse coupler 400 is be positioned across the first apical vertebra 42 such that a connecting portion 422 of an adjustment arm 402 extends from the first side 40A of the spine 40 to the second side 40B of the spine 40, according to some embodiments.

As previously discussed, the first transverse coupler 400 optionally has the force directing member 404 rigidly coupled to the adjustment arm 402. In some embodiments, the adjustment retainer 454 is actuated along the force directing member 404 by rotating a threaded cap 455 of the adjustment retainer 454 clockwise along a threaded portion of the force directing member 404. Actuating the adjustment retainer 454 decreases an effective length L (FIG. 57) of the force directing member 404 as desired. In some embodiments, the effective length L becomes approximately zero when the adjustment arm 402 becomes seated flush against the adjustment assembly 450. In other words, actuating the retainer 454 optionally changes the distance and orientation of the rider 452 with respect to the adjustment arm 402. In some embodiments, actuating the retainer 454 optionally couples the rider 452 to the adjustment arm 402. The force directing member 404 is optionally cut or broken off to a shorter length, as desired, during the procedure as the effective length L decreases from the initial effective length.

As the adjustment retainer 454 is optionally actuated along the force directing member 404, the rider 452 provides a resistance force that transmits through the force directing member 404 to the adjustment arm 402. In some embodiments, the resistance force causes the second rod 14 to move towards the first rod 12, which laterally translates a portion of the spine 40 towards the first rod 12.

In some embodiments, the adjustment retainer 454 is actuated along the first force directing member 404 such that the first surface 414 of the adjustment arm 402 comes into contact with the adjustment assembly 450. The adjustment retainer 454 is then optionally further actuated to pivot the rider 452 and the adjustment arm 402 towards each other such that the first surface 414 of the adjustment arm 402 becomes seated flush against a second surface 460 of the rider 452. As the adjustment assembly 450 and the adjustment arm 402 impinge and ultimately become seated together, according to some embodiments. Once the adjustment arm 402 and the adjustment assembly 450 are brought into the desired amount of contact or the desired effective length L of the force directing member 404 has been achieved.

As discussed above, if desired, the secondary stabilization rod can be fastened to promote a fusion process at one or more designated spinal segments, and thereby prohibit any freedom of motion at any of the one or more designated spinal segments. However, spinal fusion of segments at various levels may not be desirable in certain spinal deformity scenarios. For example, Early Onset Scoliosis (EOS) is a progressive spinal deformity in young children. In various situations, such as some forms of EOS, correcting the deformity with definitive fusion of vertebrae may not be desirable, including where vertebral fusion can stunt, or otherwise inhibit patient growth, for example.

Accordingly, some embodiments relate to spinal correction systems that provide means for maintaining a correction to facilitate spinal remodeling while minimizing or in the absence of substantial vertebral fusion. In some embodiments, the spine retains freedom of motion (in one or more degrees of freedom) above (superior to) and below (inferior to) the spinal segment undergoing correction (such as a target region or apical region), and additionally retains freedom of motion (in one or more degrees of freedom) along the spinal segment undergoing correction.

Figure 60:
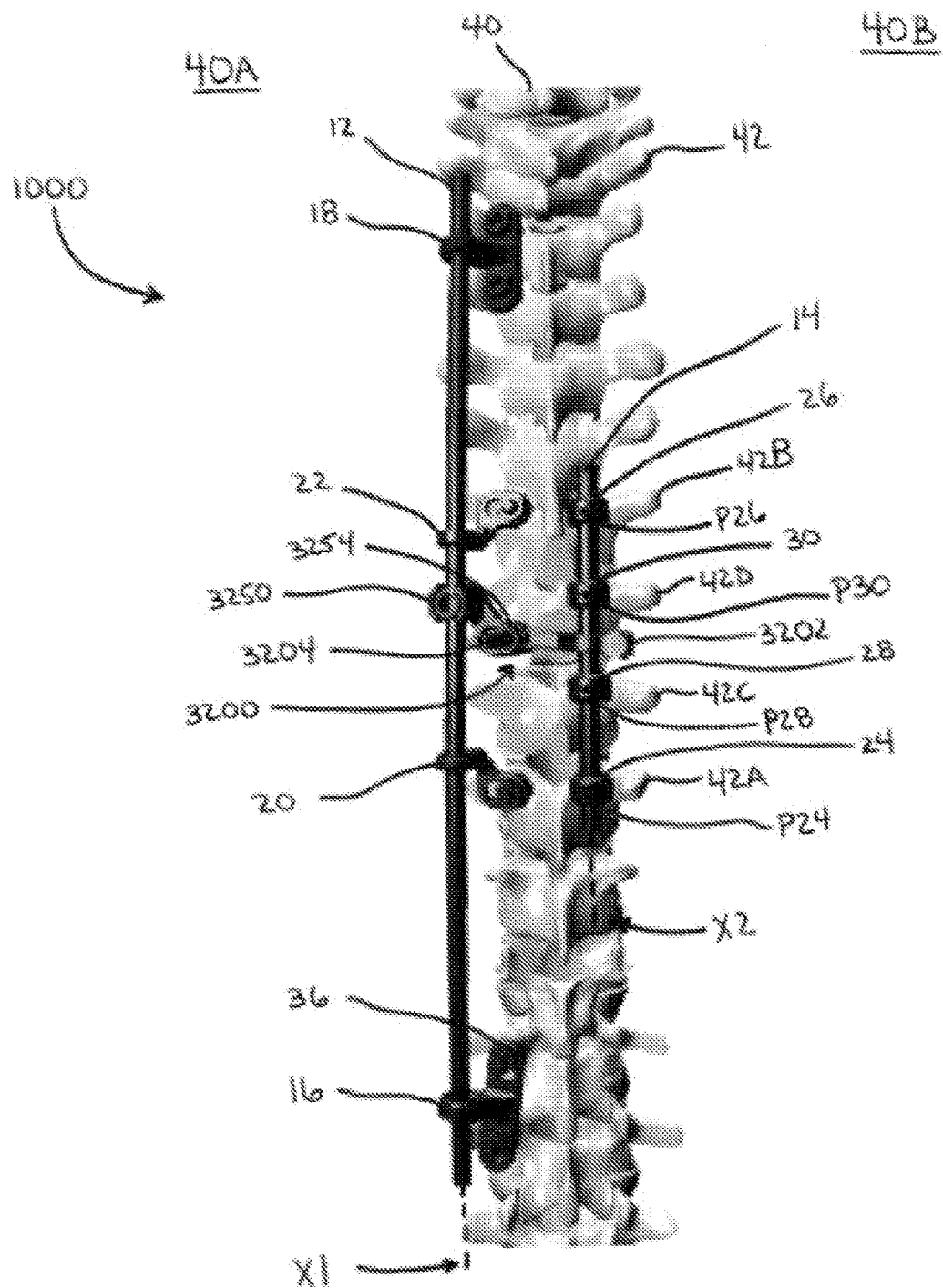
FIG. 60 is a schematic illustration of an implantable spinal correction system, according to some embodiments.

FIG. 60 illustrates a spinal correction system 1000 that provides spinal stability and correction of a target apical region in the presence of minimal or no vertebral fusion. Similar to various above-discussed embodiments, the spinal stabilization system 1000 illustrated in FIG. 60 includes a plurality of rod anchors, also described as stabilizing anchors (16, 18, 20, 22, 24, 26, 28, and 30), which are optionally substantially similar to the above-discussed stabilizing anchors, and a plurality of fasteners 36, such as bone screws or pedicle screws, for securing components of the system 1000 to a spine 40 having a first side 40A and a second side 40B. In some embodiments, one or more of the stabilizing anchors (e.g., 16, 18, 20, 22, 24, 26, 28, and 30) provide means for allowing first rod 12 and/or second rod 14 to angulate without substantial lateral translation relative to the stabilizing anchor and without substantial rotation about the longitudinal axis X. As indicated, depending upon implementation, the stabilizing anchors 16, 18, 20, 22, 24, 26, 28, and 30 are optionally any of previously-discussed anchors, or stabilizing anchors that, in turn, allow the first rod 12 and second rod 14 to slide axially, or otherwise translate axially, along the longitudinal axis relative to the stabilizing anchors (16, 18, 20, 22, 24, 26, 28, and 30) through pivot points associated with each of the stabilizing anchors. In some embodiments, rod 12 and/or rod 14 are able to change in pitch, yaw, and roll about each of the pivot points associated with each of the stabilizing anchors. In other embodiments, rod 12 and/or rod 14 are able to change in pitch, yaw, and roll about some of the various pivot points. In yet other embodiments, one or more of the stabilizing anchors (e.g., 16, 18, 20, 22, 24, 26, 28, and 30) are additionally or alternatively adapted, or otherwise structured, to limit rotation, or roll, of the first rod 12 and/or second rod 14 about the longitudinal axis X (e.g., X1 or X2) of the respective rod.

As is illustrated in FIG. 60, stabilizing anchors 16, 18, 20, and 22 are positioned along the first side 40A of the spinal column 40 and are optionally secured to the spine 40 using one or more of the methods or configurations discussed herein. Stabilization 16, 18, 20, and 22 each have a pivot point associated therewith (such as pivot point P1 disclosed herein). Moreover, stabilizing anchors 16, 18, 20, and 22, are coupled to the first rod 12 (such as according to the embodiments described herein). In some embodiments, rod 12 is free to change position axially, rotationally, or angularly (e.g., pitch, yaw, and/or roll) relative to stabilizing anchors 16, 18, 20, and 22 at one or more of the pivot points associated with the individual anchors. However, in this illustrated example, rod 12 is constrained from any substantial lateral translation (medial-lateral and/or anterior-posterior translation) as previously described.

As is further illustrated in FIG. 60, a plurality of stabilizing anchors 24, 26, 28, and 30, are additionally positioned along the second side 40B of the spinal column 40 and are adapted to interface with second rod 14. Similar to stabilizing anchors 16, 18, 20, and 22, stabilizing anchors 24, 26, 28, and 30 each have a pivot point associated therewith and include any of the previously described anchor designs or stabilizing anchor designs and are optionally secured to the spine 40 using one or more of the methods or configurations described herein. In some embodiments, rod 14 is free to change position axially, rotationally, or angularly (e.g., pitch, yaw, and/or roll) relative to one or more of the stabilizing anchors 24, 26, 28, and 30. However, in this illustrated example, rod 14 is constrained from any substantial lateral translation (medial-lateral or anterior-posterior translation) as previously described.

Spinal correction system 1000 additionally includes a transverse coupler 3200 positioned along, and secured to each of rods 12 and 14. In some embodiments, the transverse coupler 3200 is optionally adapted, or otherwise structured, to be positioned laterally across one or more of the vertebrae 42 and located at or near an apical position along the spine 40 (thereby linking a concave and a convex side of the spine). For example, as is illustrated in FIG. 60, the transverse coupler 3200 is adapted to extend from the first side 40A of the spine 40 toward, and ultimately across to the second side 40B of the spinal column 40, thereby establishing a link between the first rod 12 and the second rod 14. In some embodiments, the transverse coupler 3200 is configured to substantially prevent changes in pitch, yaw, roll, and axial sliding by one or both of the rods 12, 14 with respect to the transverse coupler 3200 to effectively constrain all relative degrees of freedom of the first rod 12 and the second rod 14 at or around the targeted apical region of the spinal column 40. For example, as discussed further below, the transverse coupler 3200 is operable to stabilize deformities against progression in each of the coronal, sagittal, and axial planes, thereby prohibiting apical translation, kyphotic changes and axial rotations while allowing the vertebrae to have at least one degree of freedom that allows movement, change in alignment, and/or growth, according to some embodiments.

As shown, the transverse coupler 3200 includes features that are substantially similar to those discussed above with respect to transverse coupler 200. For example, in some embodiments, transverse coupler 3200 includes an adjustment arm 3202 adapted to be coupled to the second rod 14, the adjustment arm 3202 being similar to the above-discussed adjustment arm 202 of the transverse coupler 200. Thus, various features of the adjustment arm 202 of the transverse coupler 200 also apply to the adjustment arm 3202 of the transverse coupler 3200.

Additionally, as shown in FIG. 60, the transverse coupler 3200 includes an adjustment assembly 3250 adapted to be secured to the first rod 12, the adjustment assembly being similar to the above-discussed adjustment assembly 250 of the transverse coupler 200. Thus, various features of the adjustment assembly 250 of the transverse coupler 200 also apply to the adjustment assembly 3250 of the transverse coupler 3200. While not illustrated, it should be appreciated that, in some embodiments, adjustment assembly 3250 of transverse coupler 3200 includes the same or similar features discussed above with respect to adjustment assembly 250 of transverse coupler 200 (such as, for example, a rider and a head portion having a pocket and one or more prongs).

As shown in FIG. 60, the transverse coupler 3200 additionally includes a force directing member 3204 and an adjustment retainer 3254. As discussed above with respect to transverse coupler 200, the force directing member 3204 (which is similar to force directing member 204 of transverse coupler 200) and the adjustment retainer 3254 (which is similar to adjustment retainer 254 of transverse coupler 200) are adapted to rigidly couple the adjustment assembly 3250 to the adjustment arm 3200.

Specifically, in some embodiments, the adjustment retainer 3254 engages with adjustment arm 3202 and/or force directing member 3204 in a manner substantially similar to that discussed above with respect to transverse coupler 200 (such as via a rider). In some embodiments, various additional features of the transverse coupler 200 also apply to transverse coupler 3200.

In some embodiments similar to those discussed above with respect to transverse coupler 200, transverse coupler 3200 (as specifically adjustment assembly 3250) optionally receives the first rod 12 in a substantially similar manner to the adjustment assembly 250. Therefore, various features of the adjustment assembly 250 of the first transverse coupler 200 also apply to the adjustment assembly 3250. Similarly, in some embodiments, adjustment arm 3202 additionally receives the second rod 14 similar to how the transverse coupler 200 receives the second rod 14. Therefore, various features of the transverse coupler 200 (or transverse coupler 400) are also applicable to adjustment arm 3202.

During operation of the spinal correction system 1000, apical vertebrae are laterally translated and/or derotated while the transverse coupler 3200 is being adjusted (see, e.g., the methods and configurations discussed above). For example, in order to assemble the transverse coupler 3200 onto the spinal correction system 1000 (FIG. 60), a physician can optionally angulate the adjustment assembly 3250 of the transverse coupler 3200 such that the transverse coupler 3200 extends to reach (or otherwise interface with) the first and the second rods 12, 14. Alternatively or additionally, a physician or other user can employ a variety of tools and associated methods. For example, the user can employ a surgical tool, such as a wrench, clamp, or gripping tool, adapted to couple to the first rod 12, the second rod 14, the transverse coupler 3200, and/or other spinal devices as desired. In some embodiments, the surgical tool optionally assists the physician in derotating and/or translating a spinal column 40 during a correction. The surgical tool optionally assists the physician in maintaining a desired configuration while assembling the spinal correction system 1000 onto the spine 40.

In some embodiments, the first transverse coupler 3200 is assembled onto the first and the second sides 40A, 40B of the spinal column 40, either at some time prior to, during, or after securing the stabilizing anchors 16, 18, 20, 22, 24, 26, 28, and 30. In some embodiments, the first rod 12 may axially translate and change in pitch, yaw, and/or roll relative to stabilizing anchors 16, 18, 20, and 22, but is substantially restricted from changing position (axial and/or lateral translation, pitch, yaw, and/or roll) relative to the transverse coupler 3200.

In some embodiments, the transverse coupler 3200 is additionally or alternatively assembled onto the second side 40B of the spine 40 by coupling the adjustment arm 3202 to the second rod 14. The adjustment arm 3202 is positioned across one or more apical vertebra and interfaces with adjustment assembly 3250 (e.g., via a force directing member and a retainer, as discussed above) such that the transverse coupler 3200 extends from the first side 40A of the spine 40 to the second side 40B of the spine 40. In some embodiments, the second rod 14 is substantially restricted from changing position (axial and/or lateral translation, pitch, yaw, and/or roll) relative to the adjustment arm 3202.

Once assembled, the transverse coupler 3200 rigidly links first rod 12 to second rod 14. Put differently, in some embodiments, because first rod 12 is rigidly coupled to adjustment assembly 3250 and adjustment arm 3202 is rigidly coupled to second rod 14, and because adjustment assembly 3250 and adjustment arm 3202 are rigidly connected together, first rod 12 is rigidly fixed with respect to second rod 14. It should be appreciated, however, that in various alternative embodiments, rods 12 and 14 are operable to change position (axially, rotationally, or angularly) relative to one another.

As discussed above and as illustrated in FIG. 60, the spinal correction system 1000 includes a plurality of stabilizing anchors 16, 18, 20, and 22, positioned along the first side 40A of the spinal column 40, and a plurality of stabilizing anchors 24, 26, 28, and 30 positioned along the second side 40B of the spinal column 40. While each of stabilizing anchors 16 and 18, as illustrated, are adapted, or otherwise structured, to be mounted or secured to a plurality of the vertebrae, it should be appreciated that each of stabilizing anchors 16 and 18 may be alternatively adapted, or otherwise structured, to be mounted or secured to a single vertebra. Similarly, while each of stabilizing anchors 20, 22, 24, 26, 28, and 30, as illustrated, are adapted, or otherwise structured, to be mounted or secured to a single vertebra, it should be appreciated that each of stabilizing anchors 20, 22, 24, 26, 28, and 30, may be alternatively adapted, or otherwise structured, to be mounted or secured to a plurality of vertebrae. In some embodiments, one or more of stabilizing anchors 20, 22, 24, 26, 28, and 30 are adapted to anchor to the vertebrae with a vertebral anchor coupling. However, it should be appreciated that one or more of the stabilizing anchors 20, 22, 24, 26, 28, and 30 may be alternatively adapted to attach directly to the vertebra as depicted by stabilizing anchors 24, 26, 28, 30. In other words, any suitable method for securing the stabilizing anchors to the spinal column is envisioned.

As is illustrated in FIG. 60, stabilizing anchors 24 and 28 are positioned along second rod 14 below (or inferior to) transverse coupler 3200. In some embodiments, stabilizing anchors 24 and 28 are coupled to one or more of the patient's vertebrae. For example, stabilizing anchor 24 is adapted, or otherwise structured, to be mounted, or fixed to one or more of the vertebrae 42, such as a first vertebra 42A (FIG. 60) located along the spine 40. Similarly, stabilizing anchor 28 is adapted to be fixed, and provides means for fixation to a second vertebra, such as a second vertebra 42C (FIG. 60). In some embodiments, stabilizing anchor 28 is substantially similar to the stabilizing anchor 24, including any desired combination of previously-described features. In some embodiments, stabilizing anchors 24 and 28 are further adapted to receive, and provide means for receiving the second rod 14 such that translational movement of the second rod 14 is limited except along the longitudinal axis X2. The second rod 14, in some embodiments, may also change in at least pitch, yaw, and/or roll about pivot points P24 and P28 (FIG. 60).

Additionally, as is illustrated in FIG. 60, stabilizing anchors 26 and 30 are positioned along second rod 14 above (or superior to) transverse coupler 3200. In some embodiments, stabilizing anchors 26 and 30 are coupled to one or more of the patient's vertebrae. For example, stabilizing anchor 26 is adapted, or otherwise structured, to be mounted, or fixed to one or more of the vertebrae 42 (or vertebral body), such as a third vertebra 42B (FIG. 60) located along the spine 40. Similarly, stabilizing anchor 30 is adapted to be fixed, and provides means for fixation to a fourth vertebra, such as a fourth vertebra 42D (FIG. 60). In some embodiments, stabilizing anchors 26 and 30 are each further adapted to receive, and provide means for receiving the second rod 14 such that the stabilizing anchors 26 and 30 limit translational movement of the second rod 14 except along the longitudinal axis X2. The second rod 14, in some embodiments, may also change in at least pitch, yaw, and/or roll about pivot points P26 and P30.

In some embodiments, stabilizing anchors 24, 26, 28, and 30 are operable to independently change axial, rotational, and/or angular position along/about second rod 14, relative to one another. For example, stabilizing anchor 24 (positioned along second rod 14) is operable to change positions from a first position along rod 14 relative to stabilizing anchors 26, 28, and 30 to a second, different position along rod 14 relative to stabilizing anchors 26, 28, and 30. Thus, because stabilizing anchors 24, 26, 28, and 30 are coupled to vertebrae 42A, 42B, 42C, and 42D, respectively, according to the example above, the spinal correction system 1000 provides that vertebra 42A can change its position along the longitudinal axis of the spinal column 40 and/or alignment (e.g., axial, angular, and/or rotational) relative to one or more of vertebrae 42B, 42C, and 42D.

By providing a spinal correction system 1000 that allows each vertebrae to change axial position along the longitudinal axis of the spinal column 40 and/or alignment relative to one or more other vertebra, the spinal column system 40 helps allow the spinal column 40 to grow (or otherwise expand) along its longitudinal axis, and thereby helps avoid overly restricting a patient's growth (i.e., spinal column growth). In some embodiments, the patient's spinal column grows according to a curvature defined by each of rods 12 and 14. Put differently, because each of rods 12 and 14 act as guides along which stabilizing anchors are permitted to axially translate, the patient's spinal column growth is governed, at least in part, by rods 12 and 14.

By permitting certain of the components of spinal correction system 1000 to change position (axially, rotationally, and/or angularly), the spinal correction system 1000 provides for various degrees of freedom. Enhancing the degrees of freedom of the system helps maximize motion of the spinal column 40 while minimizing system constraint. In some embodiments, the system 1000 permits flexion, extension, and axial rotation, as well as left side and right side bending, where left bending is facilitated by axial shortening on the left side and axial lengthening on the right side.

It should be appreciated that while the constrained vertebrae (such as vertebrae 42A, 42B, 42C, and 42D) are free to change axial position relative to one another, constrained vertebrae are also free, in some embodiments, to change in at least axial position relative to other vertebrae in the spinal column 40.

In some alternative embodiments, the spinal correction system 1000 maintains certain of the above-discussed vertebral degrees of freedom while providing the spinal column system 1000 with certain additional constraints. For example, in some embodiments, although not illustrated, the transverse coupler 3200 is coupled to (or otherwise fixed to) a vertebra of the spinal column 40. Accordingly, the transverse coupler 3200 and the vertebrae to which it is fixed are constrained from changing axial position relative to one another (although in various embodiments, certain additional degrees of freedom remain unconstrained). In addition to the first and second rods 12 and 14 being constrained relative to one another and constrained relative to the transverse coupler 3200 (as discussed above), the first and second rods 12 and 14 are optionally also constrained from changing at least axial position relative to the vertebrae to which the transverse coupler 3200 is fixed.

Although not illustrated in the accompanying figures, the transverse coupler 3200, in some embodiments, is fixed to a fifth vertebra 42E that is positioned axially along the longitudinal axis of the spinal column 40 between vertebrae 42C and 42D such that fifth vertebra 42E is constrained from changing position (axially, laterally, rotationally, or angularly) relative to the transverse coupler 3200. Under such a configuration, although vertebra 42E is fully constrained relative to the transverse coupler 3200, the other vertebrae constrained by the spinal correction system 1000 (e.g., 42A, 42B, 42C, and 42D) are free to change axial position relative to the fully constrained vertebra 42E. Put differently, each and every vertebrae located above (superior to) the fully constrained vertebra 42E (including vertebrae 42B and 42D) are free to change in at least their axial position (and additionally in various embodiments, their rotational and angular positions) relative to fully constrained vertebra 42E. Similarly, each and every vertebrae located below (inferior to) the fully constrained vertebra 42E (including vertebrae 42A and 42C) are free to change in at least their axial position (and additionally in various embodiments, their rotational and angular positions) relative to fully constrained vertebra 42E. Moreover, each of the vertebrae located above (superior to) and below (inferior to) the fully constrained vertebrae 42E is free to change at least their axial position along the longitudinal axis of the spinal column relative to one another. Thus, this alternative spinal correction system 1000 helps allow the spinal column 40 to grow (or otherwise expand) along its longitudinal axis yet constrains each of rods 12 and 14 from changing axial positioning relative to at least one designated vertebrae of the spinal column 40. This alternative spinal correction system similarly helps avoid artificially restricting a patient's growth (i.e., spinal column expansion). It should be appreciated that, in various embodiments, the transverse coupler 3200 is operable to be fixed to a plurality of vertebrae.

In other embodiments, the spinal correction system 1000 includes a plurality of stabilizing anchors, also described as rod anchors that are configured to permit axial translation on one side of the spinal column while restricting, or otherwise preventing, axial translation on another side of the spinal column. For example, referring again to FIG. 60, though not shown, in some embodiments, each of the stabilizing anchors 16, 18, 20, and 22 (positioned along the first side 40A of the spinal column 40), are operable to allow for at least axial translation along first rod 12 (as is discussed above). However, in these embodiments, one or more of the stabilizing anchors 24, 26, 28, and 30 (positioned along the second side 40B of the spinal column 40), such as stabilizing anchors 28 and 30, are restricted from axial translation along second rod 14. Although the first side 40A of the spinal column 40 at vertebrae 42C and 42D is free to expand (or alternatively contract), the second side 40B of the spine at vertebrae 42C and 42D is constrained by stabilizing anchors 28 and 30 from expanding (or alternatively contracting). Accordingly, in this embodiment, as the first side 40A of the spinal column 40 at vertebrae 42C and 42D expands relative to the second side 40B of the spinal column 40 at vertebrae 42C and 42D, a concave curvature otherwise existing on the first side 40A of the spinal column 40 at vertebrae 42C and 42D is reduced (or is otherwise eliminated). Similarly, as first side 40A of the spinal column 40 at vertebrae 42C and 42D expands relative to the second side 40B of the spinal column 40 at vertebrae 42C and 42D, a convex curvature otherwise existing on the second side 40B of the spinal column 40 at vertebrae 42C and 42D is reduced (or is otherwise eliminated).

It should be generally understood that, in some embodiments, the spinal correction system 1000 can be configured (or implemented) such that the first rod 12 longitudinal axis X1 and the second rod 14 longitudinal axis X2 converge at one end and diverge at another. Put differently, under this configuration, a longitudinal axis X2 along which the second rod 14 extends is not parallel to a longitudinal axis X1 along which the first rod 12 extends. It should be appreciated that, in these embodiments, alteration of the alignment between axes X1 and X2 provides for correction of a spinal deformity as would be understood by one of ordinary skill.

While certain of the above discussed embodiments provide for a spinal correction system 1000 that allows a first side 40A and a second side 40B of a spinal column 40 to expand (or alternatively contract) relative to one another, various alternative embodiments provide additional configurations for a spinal correction system 1000 that permits the spinal column 40 to grow on the first side 40A while restricting or minimizing growth on the second side 40B. In such embodiments, a spinal correction system 1000 includes stabilization anchors 16, 18, 20 and 22 that allow the first rod 12 to slide axially on the first side 40A while stabilization anchors 24, 26, 28 and 30 to restrict the second rod 14 to slide axially on the second side 40B.

In some embodiments, such a spinal correction system 1000 includes a plurality of transverse couplers 3200. For example, the spinal correction system 1000 illustrated in FIG. 61 includes a plurality of transverse couplers 3200A and 3200B. In some embodiments, each transverse coupler (3200A and 3200B) extends across the spinal column 40 from the first side 40A to the second side 40B. Additionally, each transverse coupler (3200A and 3200B) is coupled to rods 12 and 14. In the illustrated example, transverse coupler 3200B is located at a superior position relative to transverse coupler 3200A, such that an apical region 5200 of the spinal column 40 is situated between transverse coupler 3200A and 3200B. Accordingly, rods 12 and 14 are constrained laterally, axially, rotationally, and angularly relative to one another. It should be appreciated that stabilizing anchors depicted in these illustrative embodiments are not meant to be limiting in that any suitable anchor disclosed herein, including rod anchors (also described as stabilizing anchors) can be utilized.

Figure 61:
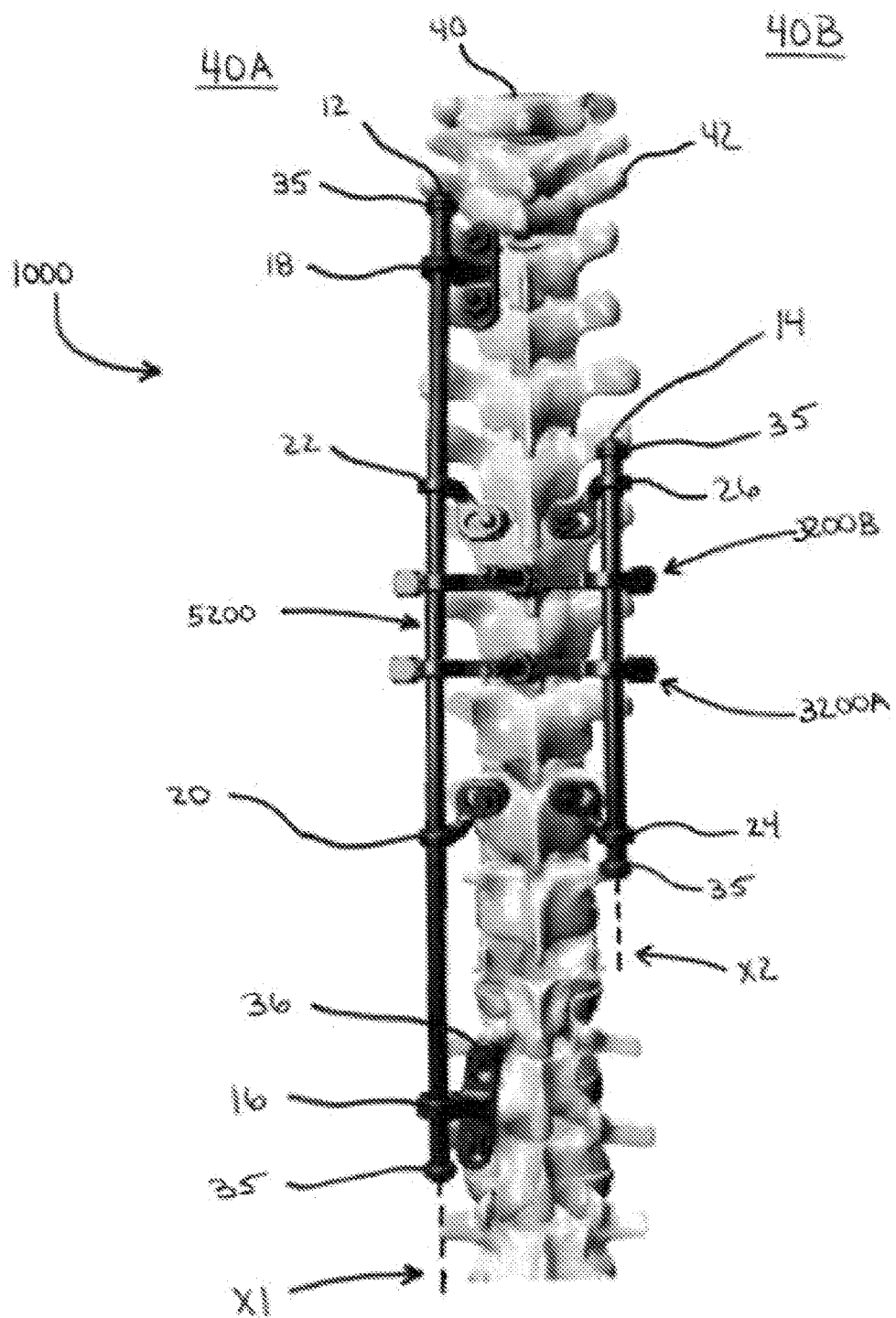
FIG. 61 is a schematic illustration of an implantable spinal correction system, according to some embodiments.

For example, while the stabilizing anchors 24 and 26 depicted in FIG. 61 provide for a configuration where rod 14 is in a different lateral position relative to rod 14 as depicted in the configuration of FIG. 60, the transverse coupler configuration depicted in FIG. 61 may be implemented in accordance with any stabilizing anchor (i.e., anchor) disclosed herein to achieve any desired configuration having any desired lateral offset relative to a longitudinal axis of the patient's spinal column. In other words, the spinal corrective systems and corresponding components disclosed herein provide for both offset (FIG. 61) and non-offset (FIG. 60) configurations. Moreover, in some embodiments, by implementing a plurality of transverse couplers 3200, the spinal correction system 1000 is operable to control a larger apical region or deformity. Further, in some embodiments, by implementing a plurality of transverse couplers 3200, the spinal correction system 1000 can be configured to span multiple motion segments (such as multiple vertebra) while maintaining a desired degree of stability and control. While these embodiments are described in association with the utilization of two transverse couplers, it should be appreciated that one or more (such as more than two) transverse couplers may be utilized to stabilize and control one or more motion segments of a patient's spinal column.

Moreover, one or more rod stops may be implemented in accordance with any of the spinal correction systems disclosed herein. For example, FIG. 61 illustrates a plurality of rod stops 35 positioned along each of rods 12 and 14. In some embodiments, rod stops are integrated into the spinal correction system to prevent one or more rods from disengaging from one or more stabilizing anchors. In some other embodiments, one or more rod stops are positioned along one or more rods to prevent undesirable movement (e.g., a specified type of movement or degree of movement such as excessive flexion or extension, twist, rotation, or excessive bending in one or more directions). In yet some other embodiments, one or more rod stops are positioned along one or more rods to selectively allow movement (or a specified degree of movement) along certain regions of the rods, while preventing movement (or a specified degree of movement) along certain other regions of the rods. Thus, while the illustrated example of FIG. 61 includes rod stops 35 positioned at each respective end of each of rods 12 and 14, it should be appreciated that rod stops 35 may be positioned along each of rods 12 and 14 at any desirable location.

It should be appreciated that any number or quantity of transverse couplers 3200 may be implemented into the spinal correction system 1000. Therefore, a spinal correction system 1000 including a plurality of transverse couplers 3200 may be tailored to the specific deformity or apical region of a patient's spinal column and thus may thus be applied to a variety of patients in need of a variety of different spinal corrections/de-rotations. Accordingly, the spinal correction system 1000 is versatile in that it can be adapted or otherwise implemented to correct spinal column deformities of any encountered size or shape.

Figure 62:
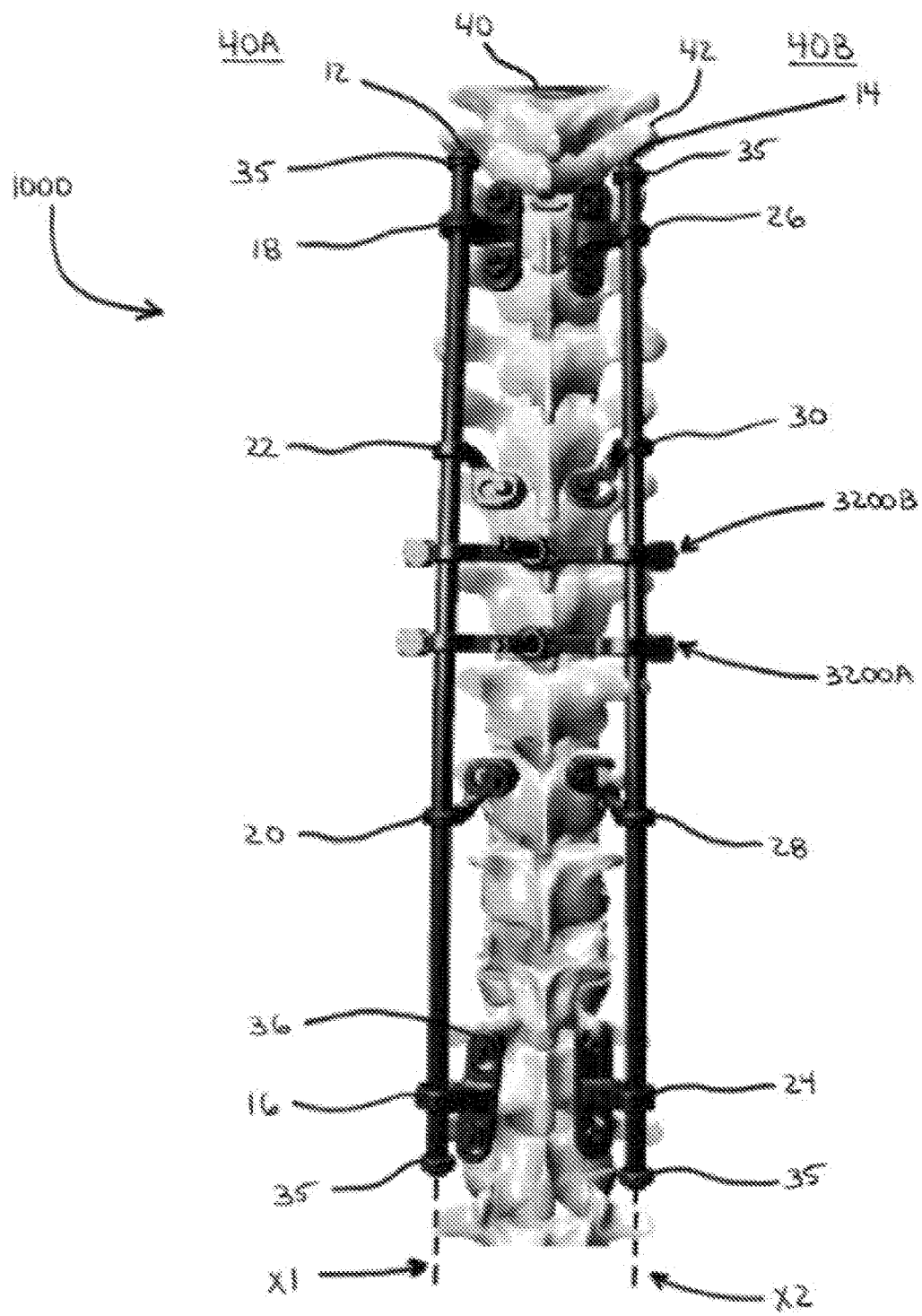
FIG. 62 is a schematic illustration of an implantable spinal correction system, according to some embodiments.

Moreover, while the above discussed spinal correction system embodiments include a first rod having a first length, and a second, different rod having a second, different length (such as a shorter relative length), it should be appreciated that the above discussed features and systems can be implemented in a spinal correction system which utilizes two rods of substantially equal length. In some such embodiments, the two rods extend along an entire length, or substantially along an entire length, of a spinal column 40. For example, the spinal correction system 1000 is illustrated in FIG. 62 includes a first rod 12 and second rod 14, wherein the second rod 14 is of a length similar to that of rod 12, and each of the first rod 12 and the second rod 14 extend along an entire length, or substantially along an entire length, of spinal column 40. In these embodiments, the spinal correction system provides for added constraints along the entire length (or substantially along the entire length) of the spinal column 40. For example, the spinal correction system 1000 illustrated in FIG. 62 provides that lateral translation of the vertebrae can be constrained at any (and potentially every) position along the spinal column. In fact, the spinal correction system 1000 illustrated in FIG. 62 provides for a system that permits the vertebrae of the spinal column to change alignment and/or grow relative to each and every other vertebra, while additionally providing for a system that can constrain laterally (medial-lateral, anterior-posterior), rotationally, and/or angularly zero, one, or more of the plurality of vertebra 42 in the spinal column 40. Thus, such embodiments provide for added stability and control of apical regions and deformities, as well as for the spinal column as a whole.

In some embodiments, mobilization of the spinal column, in part or in whole, can be effectuated while maintaining sufficient stabilization through the use of one or more stabilization members. For example, FIG. 63 illustrates a motion segment of a patient's spine (comprised of one or more vertebra) in which stabilization members 5000A and 5000B each span the motion segment and allow for axial relative translation (and additionally or alternatively in various embodiments, rotational and/or angular change) while providing stability, without fusing any vertebra of the motion segment to any other vertebra. In this illustrated example of FIG. 63, stabilization member 5000A is positioned along the second side 40B of a patient's spinal column 40 and stabilization member 5000B is positioned opposite to stabilization member 5000A along the first side 40A of the patient's spinal column 40. While FIG. 63 illustrates the use of a plurality of stabilization members (i.e., 5000A and 5000B), it should be appreciated that, in some embodiments, a single stabilization member is utilized to provide stability. It should also be appreciated that, while the above-discussed stabilization members span a single motion segment, in some embodiments, the above-discussed stabilization members are configured to span a plurality of motion segments (such as any number of vertebrae in the patient's spinal column).

In some embodiments, a stabilization member 5000 is coupled to at least a first and a second stabilizing anchor (e.g., rod anchor). In some embodiments, at least one of the stabilizing anchors is configured to prevent substantial axial and lateral (lateral-medial and anterior-posterior) translation, as well as angular (pitch and yaw) and rotational (roll) change. However, it should be appreciated that the first and second stabilizing anchors may take the form of (and thus operate according to) any of the stabilizing anchors disclosed herein. In the illustrated example of FIG. 63, stabilization member 5000A is coupled to stabilizing anchors 524 and 534 such that the stabilization member can change axial, angular, and rotational position relative to the first stabilizing anchor 524, while being prevented from substantial axial, lateral, angular, and rotational change relative to the second stabilizing anchor 534.

Specifically, arm portion 5076A of stabilization member 5000A passes through a pivot point P1A defined by the first stabilizing anchor 524 (see pivot point P1 and stabilizing anchor 18 discussed above), such that the stabilization member 5000A is prevented from substantial lateral translation (medial-lateral and/or anterior-posterior) at the pivot point P1A while maintaining freedom to slide axially (or translate axially) through the pivot point P1A and change position angularly (e.g., pitch and yaw) and/or rotationally (e.g., roll) about the pivot point P1A. It should be appreciated that the first stabilization member 524 may be mounted to (or otherwise secured to) a vertebra of the patient's spine according to any of the embodiments disclosed herein.

As discussed above, in some embodiments, the stabilization member is additionally constrained from substantially changing position axially, laterally, angularly, and rotationally relative to the second stabilization member (see the discussion of stabilization member 20 disclosed herein). For example, as is illustrated in FIG. 63, arm portion 5076B of stabilization member 5000A is coupled to stabilization member 534 such that stabilization member 5000A is constrained from substantially changing position axially, laterally, angularly, and rotationally relative to the stabilization member 534. It should be appreciated that the second stabilization member 534 may be mounted to (or otherwise secured to) a vertebra (e.g., vertebral body) of the patient's spine according to any of the embodiments disclosed herein.

By coupling a stabilization member with a plurality of stabilizing anchors such that the stabilization member maintains certain degrees of freedom (such as axial, angular, and/or rotational) with respect to one of the stabilization members while being substantially fully constrained relative to the other stabilization member, the motion segment of the spinal column under correction can be stabilized while maintaining the ability to grow. That is, the spinal correction system can stabilize a deformed segment of the spinal column in need of correction, while permitting that segment to appropriately expand, contract, flex, extend, and bend.

As discussed above, in some embodiments, a plurality of stabilization members are utilized in association with a motion segment of a patient's spine. In some embodiments (not shown), the second stabilization member takes a form similar to the first stabilization member 5000A. In some other embodiments, the second stabilization member is dissimilar to the first stabilization member (e.g., the second stabilization member is further configured to be coupled with one or more additional components of a spinal correction system relative to the first stabilization member). For example, referring again to FIG. 63, stabilization member 5000B is coupled to a first stabilizing anchor 516 and a second stabilizing anchor 532 such that the stabilization member 5000B can change axial, angular, and rotational position relative to the first stabilizing anchor 516, while being prevented from substantial axial, lateral, angular, and rotational change relative to the second stabilizing anchor 532. Accordingly, it should be appreciated that, in this illustrated example, stabilization member 5000B is coupled to first stabilizing anchor 516 and second stabilizing anchor 532 in substantially the same manner as discussed above regarding stabilization member 5000A and stabilizing anchors 524 and 534. Moreover, the stabilization member 5000B is further configured to be coupled with a first rod 120 (which is substantially similar to rod 12 disclosed herein).

Specifically, as is illustrated in FIG. 64, the stabilization member 5000B includes a housing portion 5072. In some embodiments, the housing portion 5072 is substantially similar to housing portion 72 of the first stabilizing anchor 16 (discussed above). For example, among various other features, the housing portion 5072 includes a body 5080 and a sleeve insert 5082, the sleeve insert 5082 defining a pivot point P1B. In some embodiments, the sleeve insert 5082 is substantially spherical in shape and the body 5080 forms a substantially spherical mating race for receiving the sleeve insert 5082 (as is similarly discussed above with respect to body 80 and sleeve insert 82 of the first stabilizing anchor 16).

In some embodiments, the stabilization member 5000B is configured to slidably receive the rod 120 by way of the sleeve insert 5082 (as is similarly discussed above with respect to stabilization member 16, or alternatively with respect to stabilization member 18). Specifically, upon assembly, the first rod 120 passes through the pivot point P1B such that the longitudinal axis of rod 120 at the pivot point P1B is generally concentric with the center of sleeve insert 5082. In some embodiments, the first rod 120 is operable to change angular positioning (pitch and yaw) about pivot point P1B. In some embodiments, similar to those discussed above with respect to stabilizing anchor 16, first rod 120 is substantially limited from rotational change about pivot point P1B. Conversely, in some alternative embodiments, similar to those discussed above with respect to stabilizing anchor 18, the first rod 120 is free to rotate about pivot point P1B. In any event, the first rod 120 remains free to slide axially within the sleeve insert 5082, according to some embodiments.

Thus, in some embodiments, the spinal correction system 1000 provides that the rod 120 may adopt multi-level positional changes about a plurality of pivot points relative to one or more vertebrae 42 of the spinal column 40, while constricting (either significantly or completely) any lateral movement. The inclusion of such additional levels of movement provide for a spinal correction system that allows for more natural movement of the spinal column while still maintaining control of apical regions and deformations under correction by preventing substantial lateral (medial-lateral and/or anterior-posterior) translation.

It should also be appreciated that a plurality of different spinal correction system configurations including a plurality of stabilization members are envisioned. The various configurations discussed below are for illustrative purposes only and are not intended to be limiting. Thus, it should be appreciated that any suitable spinal correction system configuration is envisioned.

In various embodiments, a spinal correction system configuration includes a plurality of stabilization members, and at least a first, second, third, and fourth stabilizing anchor. In these embodiments, a first one of the plurality of stabilization members is constrained from substantial lateral (medial-lateral and anterior-posterior) movement relative to the first stabilizing anchor, but is free to change axial, angular (pitch and yaw), and/or rotational (roll) position relative to the first stabilizing anchor. The first stabilization member is further substantially fully constrained relative to the second stabilizing anchor (i.e., constrained from substantial axial, lateral, angular, and rotational positional changes).

Similarly, in these embodiments, a second one of the plurality of stabilization members is constrained from substantial lateral (medial-lateral and anterior-posterior) movement relative to the third stabilizing anchor, but is free to change axial, angular (pitch and yaw), and/or rotational (roll) position relative to the third stabilizing anchor. The second stabilization member is further substantially fully constrained relative to the fourth stabilizing anchor (i.e., constrained from substantial axial, lateral, angular, and rotational positional changes).

In some embodiments, the first and second stabilizing anchors are mounted or secured to a first vertebra and a second vertebra (inferior or superior to the first vertebra), respectively, of a patient's spine. Additionally, in this embodiment, the third and fourth stabilizing anchors are mounted or secured to a third vertebra and a fourth vertebra (inferior or superior to the third vertebra), respectively, of the patient's spine. In one embodiment, the first vertebra and the third vertebra are the same vertebra and the second vertebra and the fourth vertebra are the same vertebra. In another embodiment, the first vertebra and the third vertebra are different. In another embodiment, the second vertebra and the fourth vertebra are different. In another embodiment, the first vertebra and the fourth vertebra are different. In another embodiment, the second vertebra and the third vertebra are different. In yet another embodiment, the first vertebra, the second vertebra, the third vertebra, and the fourth vertebra are each different. It should be appreciated that any suitable combination is envisioned. It should also be appreciated that the stabilization member is not limited to coupling to two stabilizing anchors, but may rather be coupled to any suitable number of anchors in any suitable configuration. Likewise, any suitable number of stabilization members may be utilized in the spinal correction system.

It should also be appreciated that the spinal correction systems disclosed herein may be assembled according to any suitable method. For example, a stabilizing anchor (such as any anchor disclosed herein) may be coupled to a rod prior to being secured to a vertebra of a patient's spine. Conversely, a stabilizing anchor (such as any anchor disclosed herein) may be secured to a patient's spine prior to being coupled to a rod. Likewise, a transverse coupler may be coupled to a rod at some point in time before, during, or after stabilizing anchors are coupled to the rod and/or secured to one or more of the patient's vertebrae. In some embodiments, during assembly of a spinal correction disclosed herein, one or more components of the system (such as a stabilizing anchor) are coupled to a rod through end loading (e.g., by sliding the component onto the rod, or alternatively sliding the rod through an opening, such as a sleeve, of the component) and subsequently positioning the component and rod at desired positions relative to one another. Conversely, as discussed above, a rod and component may be coupled together by top loading the rod onto the component (e.g., by positioning the rod within a receiving surface of the component), as is discussed above with respect to FIGS. 20 and 21.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A spinal correction system comprising:
   a first rod configured to extend along a first side of a spine;
   a first stabilization member including an arm and a housing unitarily formed with one another, the arm configured to extend along the first side of the spine, the arm having a first arm portion extending in a first direction from the housing and a second arm portion extending in a second opposite direction from the housing, the first stabilization member configured to laterally constrain the first rod while allowing the first rod to slide axially and to change in pitch, yaw, and roll about a first pivot point;
   a first rod anchor configured to be secured to a vertebra of the spine and to laterally constrain the first arm portion of the first stabilization member while allowing the first stabilization member to slide axially and to change in pitch, yaw, and roll about a second pivot point;
   a second rod anchor configured to be secured to a vertebra of the spine and to laterally constrain the second arm portion of the first stabilization member while preventing the first stabilization member from sliding axially and from changing in pitch, yaw, and roll;
   a second stabilization member configured to extend along a second side of the spine;
   a third rod anchor configured to be secured to a vertebra of the spine and to laterally constrain the second stabilization member while allowing the second stabilization member to slide axially and to change in pitch, yaw, and roll about a third pivot point; and
   a fourth rod anchor configured to be secured to a vertebra of the spine and to laterally constrain the second stabilization member while preventing the second stabilization member from sliding axially and from changing in pitch, yaw, and roll.

2. The system according to claim 1, wherein the second stabilization member is configured to laterally constrain a second rod while allowing the second rod to slide axially and to change in pitch, yaw, and roll about a fourth pivot point.

3. The system according to claim 2, further comprising a transverse coupler extending laterally between the first and second rods, the transverse coupler laterally constraining the first and second rods and preventing the first and second rods from changing in pitch, yaw, and roll relative to the transverse coupler.

4. The system according to claim 2, wherein the first rod is longer than the second rod.

5. The system according to claim 2, wherein the first and second rods are similar in length.

6. The system according to claim 1, wherein each of the first and third rod anchors includes a housing and a sleeve rotatably received in the housing.

7. The system according to claim 6, wherein the housing defines a concave surface and the sleeve defines a convex surface slidably received with the concave surface of the housing in a complementary fit.

8. The system according to claim 1, wherein the housing extends in a direction transverse to the first and second arm portions.

9. A spinal correction system comprising:
   a first rod configured to extend along a first side of a spine;
   a second rod;
   a first stabilization member configured to extend along the first side of the spine, the first stabilization member configured to laterally constrain the first rod while allowing the first rod to slide axially and to change in pitch, yaw, and roll about a first pivot point;
   a first rod anchor configured to be secured to a vertebra of the spine and to laterally constrain the first stabilization member while allowing the first stabilization member to slide axially and to change in pitch, yaw, and roll about a second pivot point;
   a second rod anchor configured to be secured to a vertebra of the spine and to laterally constrain the first stabilization member while preventing the first stabilization member from sliding axially and from changing in pitch, yaw, and roll;
   a second stabilization member configured to extend along a second side of the spine;
   a third rod anchor configured to be secured to a vertebra of the spine and to laterally constrain the second stabilization member while allowing the second stabilization member to slide axially and to change in pitch, yaw, and roll about a third pivot point;
   a fourth rod anchor configured to be secured to a vertebra of the spine and to laterally constrain the second stabilization member while preventing the second stabilization member from sliding axially and from changing in pitch, yaw, and roll; and
   a transverse coupler extending laterally between the first and second rods, the transverse coupler laterally constraining the first and second rods and preventing the first and second rods from changing in pitch, yaw, and roll relative to the transverse coupler, the transverse coupler includes including:
     a force directing member defining a length and having an elongate rigid body;
     an adjustment arm; and
     an adjustment assembly
       a first rod coupler;
       an adjustment retainer; and
       a rider adapted to couple to the body of the force directing member such that the rider is moveable along the body.

10. The system according to claim 9, wherein the adjustment retainer or the body of the force directing member is threaded.

11. The system according to claim 9, wherein the rider slidably receives the force directing member.

12. The system according to claim 9, wherein the adjustment retainer is actuable along the force directing member to adjust a length along the force directing member between the adjustment arm and the adjustment assembly.

13. The system according to claim 9, wherein the adjustment retainer is actuable along the force directing member such that the second rod moves relative to the first rod for laterally translating a portion of the spine relative to the first rod.

14. The system according to claim 9, wherein the adjustment arm has a first end, a second end, and a longitudinal axis extending between the first and second ends, and wherein an angle between a longitudinal axis of the force directing member and the longitudinal axis is adjustable.

15. The system according to claim 14, wherein the adjustment retainer is actuable along the force directing member such that the angle is adjusted.

16. The system according to claim 9, wherein the second stabilization member is configured to laterally constrain the second rod while allowing the second rod to slide axially and to change in pitch, yaw, and roll about a fourth pivot point.

17. A spinal correction system comprising:
   a first rod configured to extend along a first side of a spine;

a second rod;

a first stabilization member configured to extend along the first side of the spine, the first stabilization member configured to laterally constrain the first rod while allowing the first rod to slide axially and to change in pitch, yaw, and roll about a first pivot point;

a first rod anchor configured to be secured to a vertebra of the spine and to laterally constrain the first stabilization member while allowing the first stabilization member to slide axially and to change in pitch, yaw, and roll about a second pivot point;

a second rod anchor configured to be secured to a vertebra of the spine and to laterally constrain the first stabilization member while preventing the first stabilization member from sliding axially and from changing in pitch, yaw, and roll;

a second stabilization member configured to extend along a second side of the spine;

a third rod anchor configured to be secured to a vertebra of the spine and to laterally constrain the second stabilization member while allowing the second stabilization member to slide axially and to change in pitch, yaw, and roll about a third pivot point;

a fourth rod anchor configured to be secured to a vertebra of the spine and to laterally constrain the second stabilization member while preventing the second stabilization member from sliding axially and from changing in pitch, yaw, and roll; and a transverse coupler extending laterally between the first and second rods, the transverse coupler laterally constraining the first and second rods and preventing the first and second rods from changing in pitch, yaw, and roll relative to the transverse coupler, the transverse coupler operable to laterally translate and rotate the second rod towards the first rod such that a portion of the spine is moved into a more correct configuration.

18. The system according to claim 17, wherein the second stabilization member is configured to laterally constrain the second rod while allowing the second rod to slide axially and to change in pitch, yaw, and roll about a fourth pivot point.

* * * * *